US012766202B2

(12) United States Patent
Malek et al.

(10) Patent No.: US 12,766,202 B2
(45) Date of Patent: Oct. 20, 2026

(54) RADIONUCLIDE AND NEAR-INFRARED DYE CONJUGATED ANTIBODY FOR DETECTION OF GD2-POSITIVE CANCER

(71) Applicants: University of Pittsburgh—Of the Commonwealth System of Higher Education, Pittsburgh, PA (US); The Curators of the University of Missouri, Columbia, MO (US)

(72) Inventors: Marcus Malek, Pittsburgh, PA (US); Gary Kohanbash, Pittsburgh, PA (US); Wilson Barry Edwards, Columbia, MO (US); Lauren Rosenblum, Pittsburgh, PA (US)

(73) Assignees: University of Pittsburgh—Of the Commonwealth System of Higher Education, Pittsburgh, PA (US); The Curators of the University of Missouri, Columbia, MO (US)

( * ) Notice: Subject to any disclaimer, the term of this patent is extended or adjusted under 35 U.S.C. 154(b) by 0 days.

(21) Appl. No.: 19/126,979

(22) PCT Filed: Nov. 3, 2023

(86) PCT No.: PCT/US2023/078622

§ 371 (c)(1),
(2) Date: May 2, 2025

(87) PCT Pub. No.: WO2024/097950

PCT Pub. Date: May 10, 2024

(65) Prior Publication Data

US 2026/0166186 A1 Jun. 18, 2026

Related U.S. Application Data

(60) Provisional application No. 63/382,434, filed on Nov. 4, 2022.

(51) Int. Cl.
*A61K 51/10* (2006.01)
*A61B 5/00* (2006.01)
*A61P 35/00* (2006.01)

(52) U.S. Cl.
CPC ........ *A61K 51/1093* (2013.01); *A61B 5/0071* (2013.01); *A61K 51/1045* (2013.01);
(Continued)

(58) Field of Classification Search
CPC ............ A61K 51/1093; A61K 51/1045; A61K 2121/00; A61K 2123/00; A61P 35/00; A61B 5/0071
See application file for complete search history.

(56) References Cited

FOREIGN PATENT DOCUMENTS

WO WO2019/059771 A2 3/2019

OTHER PUBLICATIONS

Barker et al., "Effect of a chimeric anti-ganglioside $G_{D2}$ antibody on cell-mediated lysis of human neuroblastoma cells," Cancer Research 51: 144-149, Jan. 1991.

(Continued)

*Primary Examiner* — Michael T Rozanski
(74) *Attorney, Agent, or Firm* — Klarquist Sparkman, LLP

(57) ABSTRACT

Disclosed herein is an antibody-conjugate comprising a monoclonal antibody that specifically binds to GD2 and comprises a heavy chain and a light chain comprising heavy and light chain variable regions set forth as SEQ ID NOs: 3 and 4, respectively. The monoclonal antibody can be conjugated to a near-infrared fluorescent dye and diethylenetriaminepentaacetic acid (DTPA). In several aspects, the antibody-conjugate further comprising Indium-111 ($^{111}In$) chelated by the DTPA. The antibody-conjugate specifically binds to GD2, and is useful, for example, in radio-guided (Continued)

and fluorescent-guided surgical techniques for intraoperative detection of GD2-positive cancer tissue.

22 Claims, 26 Drawing Sheets

Specification includes a Sequence Listing.

(52) U.S. Cl.
CPC .......... *A61P 35/00* (2018.01); *A61K 2121/00* (2013.01); *A61K 2123/00* (2013.01)

(56) References Cited

OTHER PUBLICATIONS

Bou-Samra et al., "Intraoperative molecular imaging: 3rd biennial clinical trials update," Journal of Biomedical Optics 28.5: 1-33, May 2023.
Butch et al., "Positron Emission Tomography Detects In Vivo Expression of Disialoganglioside GD2 in Mouse Models of Primary and Metastatic Osteosarcoma," Cancer Res. 79.12: 3112-3124, Jun. 2019.
Canete et al., "Surgical Treatment for Neuroblastoma: Complications During 15 Years' Experience," Journal of Pediatric Surgery 33.10: 1526-1530, Oct. 1998.
Cheever et al., "The Prioritization of Cancer Antigens: A National Cancer Institute Pilot Project for the Acceleration of Translational Research," Clin Cancer Res. 15.17: 5323-5337, Sep. 2009.
Chopra, "$^{111}$In-(Diethylenetriamine pentaacretic acid)$_n$-trastuzumab-(IRDye 800CW)$_m$," Molecular Imaging and Contrast Agent Database (MICAD), Jan. 2009, retrieved electronically at <<https://www.ncbi.nlm.nih.gov/sites/books/NBK23496/>> on Mar. 12, 2025 (4 pages).
ClinicalTrials.gov ID NCT02736578, "Cetuximab-IRDye 800CW and Intraoperative Imaging in Finding Pancreatic Cancer in Patients Undergoing Surgery," Sponsor Eben Rosenthal, Study completed on May 22, 2017, retrieved electronically at <<https://clinicaltrials.gov/study/NCT02736578>> on Mar. 13, 2025 (14 pages).
ClinicalTrials.gov ID NCT01972373, "Visualization of Rectal Cancer During Endoscopy, Using a Fluorescent Tracer (Rapido-Tract)," Sponsor University Medical Center Groningen, Study completed on Jan. 2017, retrieved electronically at <<https://clinicaltrials.gov/study/NCT01972373?term=NCT01972373&rank=1>> on Mar. 13, 2025 (12 pages).
ClinicalTrials.gov ID NCT01508572, "VEGF-targeted Fluorescent Tracer Imaging in Breast Cancer," Sponsor University Medical Center Groningen, Study completed on Jan. 2015, retrieved electronically at <<https://clinicaltrials.gov/study/NCT01508572?term=NCT01508572&rank=1>> on Mar. 13, 2025 (11 pages).
ClinicalTrials.gov ID NCT04511078, "Phase II Panitumumab-IRDye800 in Head & Neck Cancer," Sponsor University of Alabama at Birmingham, Study to be completed on Dec. 31, 2027 (estimate), retrieved electronically at <<https://clinicaltrials.gov/study/NCT04511078?term=NCT04511078&rank=1>> on Mar. 13, 2025 (9 pages).
Cohn et al., "The International Neuroblastoma Risk Group (INRG) Classification System: An INRG Task Force Report," Journal of Clinical Oncology 27.2: 289-297, 2008.
Dhillon, "Dinutuximab: First Global Approval," Drugs 75: 923-927, 2015.
Gangadharan et al., "Multiinstitutional Phase 2 Clinical Trial of Intraoperative Molecular Imaging of Lung Cancer," Ann Thorac Surg. 112: 1150-1159, 2021.
Gatta et al., "Childhood cancer survival in Europe 1999-2007: results of Eurocare-5—a population-based study," Lancet Oncol. 15: 35-47, 2014.
Gillies et al., "High-level expression of chimeric antibodies using adapted cDNA variable region cassettes," Journal of Immunological Methods 125: 191-202, 1989.
Gilman et al., "Phase I Study of ch14.18 With Granulocyte-Macrophage Colony—Stimulating Factor and Interleukin-2 in Children With Neuroblastoma After Autologous Bone Marrow Transplantation or Stem-Cell Rescue: A Report From the Children's Oncology Group," Journal of Clinical Oncology 27.1: 85-91, 2008.
Handgretinger et al., "A Phase I Study of Human/Mouse Chimeric Anti-ganglioside GD2 Antibody ch14.18 in Patients with Neuroblastoma," Eur J Cancer 31A.2: 261-267, 1997.
Hekman et al., "Tumor-targeted Dual-modality Imaging to Improve Intraoperative Visualization of Clear Cell Renal Cell Carcinoma: A First in Man Study," Theranostics 8.8: 2161-2170, 2018.
Hernot et al., "Latest developments in molecular tracers for fluorescence image-guided cancer surgery," Lancet Oncol. 20: e354-367, 2019.
Holmes et al., "Influence of Surgical Excision on the Survival of Patients With Stage 4 High-Risk Neuroblastoma: A Report From the HR-NBL1/SIOPEN Study," J Clin Oncol. 38: 2902-2915, 2020.
"International Nonproprietary Names for Pharmaceutical Substances (INN)," WHO Drug Information 27.2: 135-209, 2013 (75 pages).
International Search Report and Written Opinion mailed in International Application No. PCT/US2023/078622 by the Australian Patent Office as International Search Authority on Jan. 30, 2024 (16 pages).
Jani et al., "The Role of Indium-I I I Radioimmunoscintigraphy in Post-Radical Retropubic Prostatectomy Management of Prostate Cancer Patients," Clinical Medicine & Research 5.2: 121-131. 2007.
Kovar et al., "A systematic approach to the development of fluorescent contrast agents for optical imaging of mouse cancer models," Analytical Biochemistry 367.1: 1-12, Aug. 2007.
Ladenstein et al., "Ch14.18 antibody produced in CHO cells in relapsed or refractory Stage 4 neuroblastoma patients," mAbs 5.5: 801-809, 2013.
Ladenstein et al., "Interleukin 2 with anti-GD2 antibody ch14.18/CHO (dinutuximab beta) in patients with high-risk neuroblastoma (HR-NBL1/SIOPEN): a multicentre, randomised, phase 3 trial," Lancet Oncol. 19: 1617-1629, 2018.
Lammie et al., "Ganglioside $GD_2$ expression in the human nervous system and in neuroblastomas—An immunohistochemical study," International Journal of Oncology 3: 909-915, 1993.
Lutje et al., "Dual-Modality Image-Guided Surgery of Prostate Cancer with a Radiolabeled Fluorescent Anti-PSMA Monoclonal Antibody," J Nucl Med. 55: 995-1001, 2014.
Maczynska et al., "Immunomodulatory activity of IR700-labelled affibody targeting HER2," Cell Death and Disease 11: 886, 2020 (13 pages).
Marshall et al., "Single-Dose Intravenous Toxicity Study IRDye 800CW in Sprague-Dawley Rats," Mol Imaging Biol. 12:583-594, 2010.
Mitsunaga et al., "Cancer Cell-Selective In Vivo Near Infrared Photoimmunotherapy Targeting Specific Membrane Molecules," Nat Med. 17.12: 1685-1691, 2012.
Morton et al., "Technical Details of Intraoperative Lymphatic Mapping for Early Stage Melanoma," Arch Surg. 127: 392-399, Apr. 1992.
Mujoo et al., "Disialoganglioside $G_{D2}$ on human neuroblastoma cells: target antigen for monoclonal antibody-mediated cytolysis and suppression of tumor growth," Cancer Research 47: 1098-1104, Feb. 1987.
Mujoo et al., "Functional properties and effect on growth suppression of human neuroblastoma tumors by isotype switch variants of monoclonal antiganglioside $G_{D2}$ antibody 14.18," Cancer Research 49: 2857-2861, Jun. 1989.
Nalla et al., "Easy and Efficient $^{111}$Indium Labeling of Long-Term Stored DTPA-Conjugated Protein," Current Radiopharmaceuticals 4: 1-4, 2011.
Nazha et al., "Disialoganglioside GD2 Expression in Solid Tumors and Role as a Target for Cancer Therapy," Frontiers in Oncology 10: 1000, Jul. 2020 (15 pages).
Okusanya et al., "Intraoperative molecular imaging can identify lung adenocarcinomas during pulmonary resection," The Journal of Thoracic and Cardiovascular Surgery 150.1: 28-35, Jul. 2015.

(56) References Cited

OTHER PUBLICATIONS

Ovacik and Lin, "Tutorial on Monoclonal Antibody Pharmacokinetics and Its Considerations in Early Development," Clin Transl Sci. 11: 540-552, 2018.
Ozkaynak et al., "Phase I Study of Chimeric Human/Maurine Anti-Ganglioside GD2 Monoclonal Antibody (ch14.18) With Granulocyte-Macrophage Colony—Stimulating Factor in Children With Neuroblastoma Immediately After Hematopoietic Stem-Cell Transplantation: A Children's Cancer Group Study," Journal of Clinical Oncology 18.24: 4077-4085, Dec. 2000.
Predina et al., "A Phase I Clinical Trial of Targeted Intraoperative Molecular Imaging for Pulmonary Adenocarcinomas," Ann Thorac Surg. 105: 901-908, 2018.
Qarziba 4.5 mg/mL concentrate for solution for infusion product information, Rentschler Biopharma SE (30 pages).
Qiu and Matthay, "Advancing therapy for neuroblastoma," Nature Reviews 19: 515-533, Aug. 2022.
Randall et al., "A Phase II, multicenter, open-label trial of OTL38 injection for the intra-operative imaging of folate receptor-alpha positive ovarian cancer," Gynecologic Oncology 155: 63-68, 2019.
Rijpkema et al., "Optimization of Dual-Labeled Antibodies for Targeted Intraoperative Imaging of Tumors," Molecular Imaging 14: 348-355, Jul. 2015.
Rijpkema et al., "SPECT- and Fluorescence Image-Guided Surgery Using a Dual-Labeled Carcinoembryonic Antigen-Targeting Antibody," J Nucl Med. 55: 1519-1524, 2014.
Rosenblum et al., "Dual-labeled anti-GD2 targeted probe for intraoperative molecular imaging of neuroblastoma," Journal of Translational Medicine 22: 940, 2024 (12 pages).
Rosenblum et al., "Intraoperative Molecular Imaging of a Mouse Model of Neuroblastoma with $^{111}$In-dinutuximab-IR800," Poster Presentation at the American Academy of Pediatrics: Section on Surgery Conference, Sep. 2023 (2 pages).
Rudnick et al., "Influence of Affinity and Antigen Internalization on the Uptake and Penetration of Anti-HER2 Antibodies in Solid Tumors," Cancer Res. 71.6: 2250-2259, Mar. 2011.
Sait and Modak, "Anti-GD2 immunotherapy for neuroblastomas," Expert Rev Anticancer Ther. 17.10: 889-904, Oct. 2017.
Sampath et al., "Dual-Labeled Trastuzumab-Based Imaging Agent for the Detection of Human Epidermal Growth Factor Receptor 2 Overexpression in Breast Cancer," J Nucl Med 48: 1501-1510, 2007.
Sampath et al., "Near infrared fluorescent optical imaging for nodal," Journal of Biomedical Optics 13.4: 041312, 2008 (10 pages).
Sever et al., "Dual Labeled Anti-GD2 Intraoperative Molecular Imaging Probe for Neuroblastoma," Journal of Nuclear Medicine 64(Suppl. 1): P209, Jun. 2023 (4 pages).
Siegel et al., "Cancer Statistics, 2021," CA Cancer J Clin 2021 71.1: 7-33, 2021.
Spreckelmeyer et al., "A Novel Tracer for GD2-Positive Neuroblastoma," Nuklearmedizin 58.2: 136, 2019 (2 pages).
Straathof et al., "Antitumor activity without on-target off-tumor toxicity of GD2-chimeric antigen receptor T cells in patients with neuroblastoma," Sci Transl Med. 12: eabd6169, 2020 (12 pages).
Tas et al., "Neuroblastoma between 1990 and 2014 in the Netherlands: Increased incidence and improved survival of high-risk neuroblastoma," European Journal of Cancer 124: 47-55, 2020.
"Technical Data Sheet: In VivoMAb anti-human Ganglioside GD2," Bio X Cell, Inc., 2020 (2 pages).
Unituxin™ (dinutuximab) injection, Highlights of Prescribing Information, United Therapeutics Corp., 2015 (19 pages).
Vahrmeijer et al., "Image-guided cancer surgery using near-infrared fluorescence," Nat Rev Clin Oncol. 10.9: 507-518, Sep. 2013.
Vieira and Rajewsky, "The bulk of endogenously produced $IgG_{2a}$ is eliminated from the serum of adult C57BL/6 mice with a half-life of 6-8 days," Eur J Immunol. 16: 871-874, 1986.
Von Allmen et al., "Impact of Extent of Resection on Local Control and Survival in Patients From the COG A3973 Study With High-Risk Neuroblastoma," Journal of Clinical Oncology 35.2: 208-216, 2016 (w/Appendix, 1 pg).
Wang et al., "Sentinel lymph node biopsy compared with axillary lymph node dissection in early breast cancer: a meta-analysis," Breast Cancer Res Treat. 129: 675-689, 2011.
Wellens et al., "Anti-GD2-IRDye800CW as a targeted probe for fluorescence-guided surgery in neuroblastoma," Scientific Reports 10: 17667, 2020 (12 pages).
Yu et al., "Long-term follow-up of a Phase III Study of ch14.18 (Dinutuximab) + Cytokine Immunotherapy in Children with High-risk Neuroblastoma: Childern's Oncology Group Study ANBL0032," Clin Cancer Res. 27.8: 2179-2189, Apr. 2021.
Yu et al., "Phase I Trail of a Human-Mouse Chimeric Anti-Disialoganglioside Monoclonal Antibody ch14.18 in Patients With Refractory Neuroblastoma and Osteosarcoma," Journal of Clinical Oncology 16.6: 2169-2180, Jun. 1998.

| Cell Line | Avg. PE Molecules/Cells |
|---|---|
| NMB6 | 906838 |
| SK-N-AS | 151749 |
| SK-N-BE(2) | 146509 |
| SH-SY55 | 47237 |
| CHP212 | 1720 |
| SK-N-SH | 1243 |

Pre-surgery

Post surgery

Residual Disease

Post-guided tracer
second attempt

RADIONUCLIDE AND NEAR-INFRARED DYE CONJUGATED ANTIBODY FOR DETECTION OF GD2-POSITIVE CANCER

CROSS REFERENCE TO RELATED APPLICATIONS

This is the U.S. National Stage of International Application No. PCT/US2023/078622, filed Nov. 3, 2023, which was published in English under PCT Article 21(2), which in turn claims priority to U.S. Provisional Application No. 63/382,434, filed Nov. 4, 2022. The provisional application is herein incorporated by reference in its entirety.

FIELD

This relates to antibody-conjugates that specifically bind to Ganglioside G2 (GD2) and their use, for example in methods of identifying cancer in a subject.

INCORPORATION OF ELECTRONIC SEQUENCE LISTING

The Sequence Listing is submitted as an XML file in the form of the file named "8123-108160-05_ST26.xml" (5,263 bytes), which was created on Apr. 14, 2025 which is incorporated by reference herein.

BACKGROUND

Cancer surgery is associated with a wide range of challenges and complications, as the primary tumor forms an intimate relationship with the surrounding vital structures and tissue while tumor deposits can be difficult to detect. During surgical tumor resection, delineation of tumor borders and detection of occult lesions would allow the surgeon to minimize complications and perform more complete resections. Unfortunately, methods to enable intraoperative tumor-specific guidance are lacking.

SUMMARY

Disclosed herein is an antibody-conjugate including a monoclonal antibody or antigen binding fragment thereof-conjugated to a near-infrared fluorescent dye and a chelator. In some examples, the chelator chelates a radioisotope. In some examples the monoclonal antibody or antigen binding fragment specifically binds to Ganglioside G2 (GD2) and includes a heavy chain and a light chain including heavy and light chain variable regions set forth as SEQ ID NOs: 3 and 4, respectively. In some examples the monoclonal antibody or antigen binding fragment includes aspects of SEQ ID NOs: 3 and 4 with linking sequences. In further examples, the antibody-conjugate specifically binds to GD2. In a specific example, the composition includes a monoclonal antibody, and the monoclonal antibody is conjugated to a near-infrared fluorescent dye and diethylenetriaminepentaacetic acid (DTPA). In several aspects, the antibody-conjugate further comprising Indium-111 ($^{111}$In) chelated by the DTPA.

In some aspects, the antibody-conjugate is used in methods for the detection of GD2-positive cancer tissue in a subject. In some aspects, the antibody-conjugate is used in methods for treatment of GD2-positive cancer tissue in a subject. In some aspects, the antibody-conjugate is used for radio-guided and fluorescent-guided surgical techniques to improve intraoperative detection of GD2-positive cancer in a subject, such as GD2-positive neuroblastoma tissue. In other aspects the GD2-positive cancer is GD2-positive osteosarcoma, melanoma, retinoblastoma, Ewing sarcoma, small cell lung cancer, glioma, soft tissue sarcoma, or breast cancer tissue. In some aspects, the antibody-conjugate is detected with the use of handheld gamma probe or handheld near infrared fluorescent camera. In some aspects, the tumor cells are surgically removed after being detected using the disclosed antibody-conjugates. In several aspects monoclonal antibodies binding to GD2 permits the detection of GD2 expressing cells in vivo or in vitro, including but not limited to the detection of GD2 positive tumor cells, delineation of tumor borders, visual mapping of the primary tumor bed, or the detection of occult tumor lesions.

Also disclosed herein is a method of producing an antibody conjugate including incubating a monoclonal antibody or antigen binding fragment with diethylenetriaminepentaacetic acid (DTPA) (such as p-SCN-Bn-CHX-A"-DTPA) under conditions sufficient to conjugate the DTPA to the monoclonal antibody or antigen binding fragment, thereby producing a monoclonal antibody or antigen binding fragment conjugated to DTPA. In some examples, the method includes incubating the monoclonal antibody or antigen binding fragment conjugated to DTPA with an 800CW dye (such as IRDye800CW-NHS) under conditions sufficient to conjugate the 800CW dye to the monoclonal antibody or antigen binding fragment conjugated to DTPA, thereby producing a monoclonal antibody or antigen binding fragment conjugated to DTPA and 800CW dye. In further examples the method includes incubating the monoclonal antibody or antigen binding fragment conjugated to DTPA and the 800CW dye with a radioisotope under conditions sufficient to conjugate the radioisotope to the monoclonal antibody or antigen binding fragment conjugated to DTPA and 800CW dye, thereby producing the antibody-conjugate.

The foregoing and other features and advantages of this disclosure will become more apparent from the following detailed description of several aspects which proceeds with reference to the accompanying figures.

BRIEF DESCRIPTION OF THE FIGURES

(FIG. 1C) Gamma signal detection from tumors labeled with antibody-conjugate at various depths of intervening processed tissue.

(FIG. 2A) FACS histogram SK-N-BE(2) cells unstained or stained with PE anti-human ganglioside GD2. (FIG. 2B) Quantification of GD2 molecules per cell on selected NB cell lines, using PE Quantibrite™ assay. (FIG. 2C) Absorbance of DTPA-αGD2-IRDye800CW (25 μg) in PBS at 280 nm (protein absorbance) and 700 nm (IRDye800CW absorbance) through a BioSep-SEC-S 2000 300×7.8 mm column at 1 mL/min (on Akta Pure instrument). No aggregation was seen (single peak with no shouldering at 280 nm) with 4-fold molar excess of IRDye800CW for conjugation (700 nm peak).

(FIG. 3A) MRI imaging (coronal views) of neuroblastoma xenografts in nu/j mice, five weeks after SK-N-BE(2) cell injection. Tumors were injected into the left adrenal gland and are outlined in a white-dashed line. (FIGS. 3L-3N) White light and SPY-PHI whole body images of tumors in situ from animals treated with $^{111}$In-αGD2-IRDye800CW, tumors indicated with T. In each animal, fluorescence in the tumor area is clearly distinct from the surrounding organs.

(FIG. 4A) Schematic overview of handheld gamma probe analysis via murine body regions and xenograft tumor in processed tissue cube. (FIG. 4B) External gamma decay measurements of regions of the mice (n=3); left flank is the region of the tumor. ***$p<0.001$. (FIG. 4C) Gamma counts from excised tumor embedded in increasing thicknesses of processed tissue (0.072 MBq), Neoprobe detection of IMI tracer in excised neuroblastoma xenograft (2 mCi) embedded within processed tissue blocks. Gamma signal detection dropped sharply when moving the probe off-axis or laterally. (FIG. 4D) Comparison of gamma decay of In-111 from different regions of the mouse body externally measured in situ with the handheld Neoprobe (n=4) on Days 3 and 4 post-tracer injections where the left flank contains the neuroblastoma tumor (left flank significantly different from all other regions on both days; $p<0.0001$) (two-way ANOVA with Sidak post-hoc multiple comparisons). (FIGS. 4E and 4F) Representative images of two neuroblastoma xenografts taken with SPY-PHI camera in white light (left) and NIR (right), four days after $^{111}$In-αGD2-IRDye800CW injection (not quantified). Under NIR light, tumor is visibly distinct from surrounding tissues. Liver in FIG. 4E and spleen in FIG. 4F have some fluorescence, but tumor is visibly brighter.

(FIGS. 5A-5D) illustrate detection of residual disease after surgery by fluorescence using the SPY-PHI. (FIG. 5A) shows left adrenal tumor (T) in situ. (FIG. 5B) shows white light image following white light tumor resection. (FIG. 5C) shows fluorescent image following white light tumor resection. Arrow shows fluorescent identification of residual disease in the tumor bed. Fluorescence marked by arrow is clearly distinct from surrounding tissue. (FIG. 5D) shows after fluorescent-guided resection of residual disease with inset showing fluorescent view of resected residual disease. No fluorescence is apparent after fluorescent-guided resection.

(FIG. 6A) Comparison of gamma decay of In-111 from different regions of the mouse body externally measured in situ with the handheld Neoprobe on Days 3 and 4 post $^{111}$In-Dinutuximab-IRDye800CW injection where the left flank contains the neuroblastoma tumor. (FIG. 6B) Gamma decay from tumor, right adrenal, and right kidney ex vivo on days 3 and 4 post $^{111}$In-Dinutuximab-IRDye800CW injection. (FIG. 6C) Gamma count biodistribution of $^{111}$In-Dinutuximab-IRDye800CW as percent injected dose per gram of tissue (% ID/g) in orthotopic xenograft neuroblastoma 3 and 4 days after probe injection. (FIG. 6D) White light and SPY-PHI images of tumors in situ from animals treated with $^{111}$In-Dinutuximab-IRDye800CW, tumors indicated with an arrow. (FIG. 6E) SPY-PHI images of ex vivo organs after $^{111}$In-Dinutuximab-IRDye800CW injection, tumor indicated with an arrow. Clockwise from the upper left are right adrenal, tumor with encased left kidney, and right kidney.

(FIG. 7C) Clockwise from the upper left are adrenal, tumor, kidney, tumor nodules, tumor nodule, tumor nodule, and kidney. (FIG. 7D) Clockwise from upper left are adrenal, tumor, kidney, tumor nodule, tumor nodule, kidney. (FIG. 7E) Gamma decay from resected tumors, and tail (control) at time of surgery in the rat model. (FIG. 7F) White light (left) and fluorescence (right) SPY-PHI images taken during surgery. Tumors indicated with T. Using near-IR camera, tumor tissue is visibly distinct from surrounding tissues.

(FIG. 8A) Gamma decay of In-111 in tumor-like inclusions (TLI) In-111 measured with the Neoprobe in counts per second (CPS) when covered by various depths of assorted porcine tissues tissue (liver, muscle, fat, or lung), or no tissue (air). (FIG. 8B) Gamma decay of ex vivo tumors following probe accumulation when covered by various depths of assorted porcine tissues tissue (liver, muscle, fat, or lung) measured with the Neoprobe in counts per second (CPS). (FIGS. 8C, 8D) White light (top) and fluorescence (bottom) SPY-PHI images of IRDye800CW of various concentrations in TLI covered by various depths of porcine organs, fluorescence is indicated with arrows. (FIG. 8C) From left to right, porcine adipose and no porcine tissue control. (FIG. 8D) Clockwise from upper left are no porcine tissue standards (of ICG), muscle, skin/muscle, lung, and liver. (FIGS. 8E-8I) A simulation of surgical use. (FIG. 8E) Tumors (arrows) were buried on the underside of porcine body wall prior to turning over. (FIG. 8F) Blinded investigator identified locations of buried tumors with Neoprobe (19 cps seen on monitor). (FIG. 8G) Gamma decay from tumor increased as investigator removed overlying tissue (88 cps seen on monitor). (FIG. 8H) Once close to surface (upper white light), the tumor can be seen with clear margins on fluorescence with the SPY-PHI (lower). (FIG. 8I) No fluorescence by SPY-PHI after resection. (FIG. 8J) Shows three incisions were made for resection of tumors using $^{111}$In-αGD2-IRDye800CW & SPY-PHI.

SEQUENCES

Figure 1A:
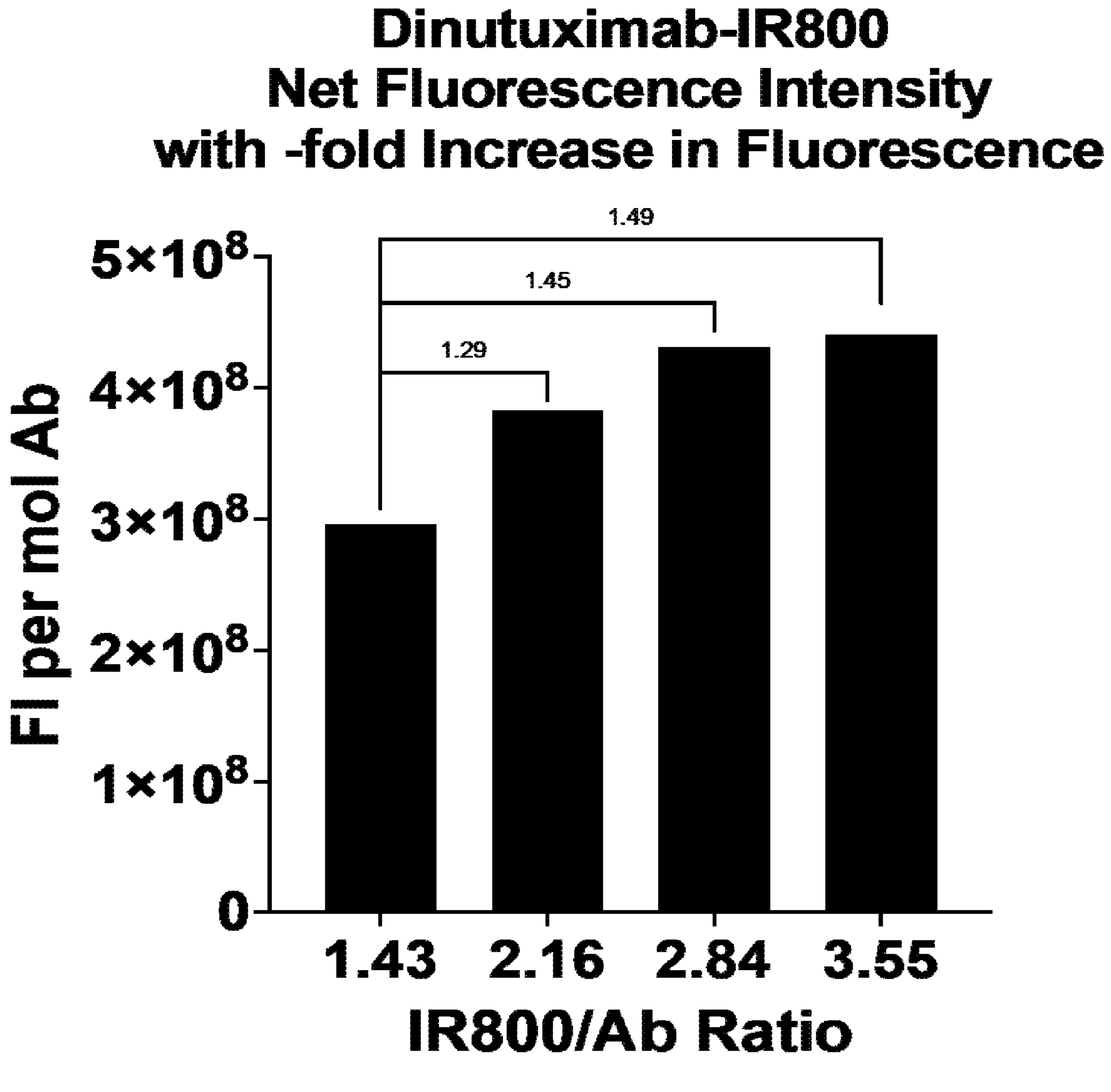
FIGS. 1A-1C. Optimization of antibody-conjugate and detection of tumors. Optimization of IRDye800CW- (FIG. 1A) and DTPA- (FIG. 1B) to antibody ratios for fluorescence intensity.

The nucleic and amino acid sequences listed in the accompanying sequence listing are shown using standard letter abbreviations for nucleotide bases, and single letter code for amino acids, as defined in 37 C.F.R. 1.822. Only one strand of each nucleic acid sequence is shown, but the complementary strand is understood as included by any reference to the displayed strand.

```
SEQ ID NO: 1 is the amino acid sequence of the dinutuximab heavy chain.
EVQLLQSGPELEKPGASVMISCKASGSSFTGYNMNWVRQNIGKSLEWIGAIDPYYGGTSYNQKFKGRATLTV

DKSSSTAYMHLKSLTSEDSAVYYCVSGMEYWGQGTSVTVSSASTKGPSVFPLAPSSKSTSGGTAALGCLVKD

YFPEPVTVSWNSGALTSGVHTFPAVLQSSGLYSLSSVVTVPSSSLGTQTYICNVNHKPSNTKVDKRVEPKSC

DKTHTCPPCPAPELLGGPSVFLFPPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKGQPREPQVYTLPPSREEMTKNQVS

LTCLVKGFYPSDIAVEWESNGQPENNYKTTPPVLDSDGSFFLYSKLTVDKSRWQQGNVFSCSVMHEALHNHY

TQKSLSLSPGK

SEQ ID NO: 2 is the amino acid sequence of the dinutuximab light chain.
EIVMTQSPATLSVSPGERATLSCRSSQSLVHRNGNTYLHWYLQKPGQSPKLLIHKVSNRFSGVPDRESGSGS

GTDFTLKISRVEAEDLGVYFCSQSTHVPPLTFGAGTKLELKRTVAAPSVFIFPPSDEQLKSGTASVVCLLNN

FYPREAKVQWKVDNALQSGNSQESVTEQDSKDSTYSLSSTLTLSKADYEKHKVYACEVTHQGLSSPVTKSEN

RGEC

SEQ ID NO: 3 is the amino acid sequence of the VH of the dinutuximab
heavy chain.
EVQLLQSGPELEKPGASVMISCKASGSSFTGYNMNWVRQNIGKSLEWIGAIDPYYGGTSYNQKFKGRATLTV

DKSSSTAYMHLKSLTSEDSAVYYCVSGMEYWGQGTSVTVSS

SEQ ID NO: 4 is the amino acid sequence of the VL of the dinutuximab
light chain.
EIVMTQSPATLSVSPGERATLSCRSSQSLVHRNGNTYLHWYLQKPGQSPKLLIHKVSNRFSGVPDRFSGSGS

GTDFTLKISRVEAEDLGVYFCSQSTHVPPLTFGAGTKLELKRT
```

DETAILED DESCRIPTION

I. Introduction

Surgical resection can be used as a component of treatment of neuroblastoma and other GD2+ cancers. However, finding and completely resecting the tumor can be a significant challenge. Provided are antibody-conjugates that specifically bind to GD2 and methods of use. In some aspects, the antibody-conjugate is $^{111}$In-dinutuximab-IRDye800CW. In some aspects, the antibody-conjugate is $^{111}$In-αGD2-IRDye800CW. $^{111}$In-dinutuximab-IRDye800CW can be detected by gamma or fluorescence emission. In some aspects, detection of antibody-conjugates assists with surgical resection of a tumor. For example, detection of antibody-conjugates may assist with detection of GD2 expressing tumor cells, delineation of tumor borders, visual mapping of the primary tumor bed, or the detection of occult tumor lesions. In some aspects, the antibody conjugate that specifically binds to GD2 is administered to treat a GD2 positive cancer.

Provided herein is an intraoperative imaging agent which permits safer and more complete operative resection by enhancing the targeted detection of tumor. As disclosed herein, dual-labeled anti-GD2 tracer, $^{111}$In-αGD2-IRDye800CW, demonstrated antigen specificity and allowed detection and visualization of neuroblastoma. This IMI tracer can increase the completeness of resection and minimize and potentially prevent surgical complications, thereby improving patient outcomes. The methods and compositions disclosed herein enable tumor resection by delineating tumor margins from surrounding vital structures and localizing occult, metastatic lesions.

II. Summary of Terms

Unless otherwise noted, technical terms are used according to conventional usage. Definitions of many common terms in molecular biology may be found in Krebs et al. (eds.), *Lewin's genes XII*, published by Jones & Bartlett Learning, 2017. As used herein, the singular forms "a," "an,"

and "the," refer to both the singular as well as plural, unless the context clearly indicates otherwise. For example, the term "an antigen" includes singular or plural antigens and can be considered equivalent to the phrase "at least one antigen." As used herein, the term "comprises" means "includes." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described herein. In case of conflict, the present specification, including explanations of terms, will control. In addition, the materials, methods, and examples are illustrative only and not intended to be limiting. To facilitate review of the various aspects, the following explanations of terms are provided:

800CW Dye: A near infrared dye with excitation/emission of about 780/800 nm. Commercial sources of 800CW dye are available for example, Li-Cor® IRDye® 800CW, available as IRDye® 800CW NHS Ester (P/N: 929-70020) or IRDye® 800CW Maleimide (P/N: 929-80020) or IRDye® 800CW Carboxylate (P/N: 929-08972). Another example commercial source of 800CW dye is BroadPharm® 800CW, available as 800CW acid (Cat #BP-25131) or 800CW NHS ester (Cat #BP-25130) or 800CW maleimide (Cat #Cyanine Hydrazide).

In one example 800CW dye is conjugated to dinutuximab to produce an antibody-conjugate that binds to cells with GD2 on their cell surface and the presence of said antibody-conjugate can be detected by fluorescence. In another example IRDye® 800CW NHS Ester is used to conjugate IRDye® 800CW to dinutuximab.

About: Unless context indicated otherwise, "about" refers to plus or minus 5% of a reference value. For example, "about" 100 refers to 95 to 105.

Administration: The introduction of a composition into a subject by a chosen route. Administration can be local or systemic. For example, if the chosen route is intravenous, the composition is administered by introducing the composition into a vein of the subject. Exemplary routes of administration include, but are not limited to, oral, injection (such as subcutaneous, intramuscular, intradermal, intraperitoneal, and intravenous), sublingual, rectal, transdermal (for example, topical), intranasal, vaginal, and inhalation routes.

Antibody: An immunoglobulin, antigen-binding fragment, or derivative thereof, that specifically binds and recognizes an analyte (antigen), such as GD2. The term "antibody" is used herein in the broadest sense and encompasses various antibody structures, including but not limited to monoclonal antibodies, polyclonal antibodies, multispecific antibodies (e.g., bispecific antibodies), and antigen binding fragments, so long as they exhibit the desired antigen-binding activity. Non-limiting examples of antibodies include, for example, intact immunoglobulins and variants and fragments thereof that retain binding affinity for the antigen. Examples of antigen binding fragments include but are not limited to Fv, Fab, Fab', Fab'-SH, $F(ab')_2$; diabodies; minibodies; linear antibodies; single-chain antibody molecules (e.g. scFv); and multispecific antibodies formed from antigen binding fragments. Antigen binding fragments my be produced by the modification of whole antibodies or synthesized de novo using recombinant DNA methodologies (see, e.g., Kontermann and Dubel (Ed), Antibody Engineering, Vols. 1-2, $2^{nd}$ Ed., Springer Press, 2010). Light and heavy chain variable regions contain a "framework" region interrupted by three hypervariable regions, also called "complementarity-determining regions" or "CDRs" (see, e.g., Kabat et al., *Sequences of Proteins of Immunological Interest*, U.S. Department of Health and Human Services, 1991). The framework region of an antibody, that is the combined framework regions of the constituent light and heavy chains, serves to position and align the CDRs in three-dimensional space. The CDRs are primarily responsible for binding to an epitope of an antigen. A "monoclonal antibody" is an antibody produced by a single clone of lymphocytes or by a cell into which the coding sequence of a single antibody has been transfected. Monoclonal antibodies include humanized and chimeric monoclonal antibodies.

Antibody-Conjugate: A complex between an antibody and at least one other molecule. In one example the antibody and at least one other molecule are linked together by a covalent bond. In one aspect, an antibody is linked to a detectable molecule; for example an antibody that specifically binds to GD2 covalently linked to 800CW dye. In another aspect, an antibody is linked to multiple detectable molecules; for example an antibody that binds to GD2 covalently liked to DTPA chelating 111 In and also covalently linked to 800CW dye. The linkage can be by chemical or recombinant means. In one aspect, the linkage is chemical, wherein a reaction between the antibody moiety and the detectable molecule has produced a covalent bond formed between the two molecules to form one molecule. A peptide linker (short peptide sequence) can optionally be included between the antibody and the detectable molecule. Because conjugates can be prepared from two molecules with separate functionalities, such as an antibody and a detectable molecule, they are also sometimes referred to as "chimeric molecules."

In an example, the antibody-conjugate is selected from $^{111}$In-dinutuximab-IRDye800CW, $^{111}$In-αGD2 (14G2a)-IRDye800CW, $^{111}$In-dinutuximab-800CW dye, $^{64}$Cu-dinutuximab-IRDye800CW, 89Zr-dinutuximab-IRDye800CW, $^{99m}$Tc-αGD2 (14G2a)-IRDye800CW.

Bifunctional Chelating Agent: A molecule that has at least two functional groups, one of which is a reactive group which can form a bond, such as a covalent bond, with another molecule, and one of which is a metal binding group. Bifunctional chelating agents may be reacted with antibodies to provide an antibody-conjugate. Conjugation between an antibody-conjugate and a metal chelate typically refers to formation of a covalent bond between the antibody chelate and the metal chelate(s). However, in some instances ion-ion bonds, ion-dipole bonds, dipole-dipole bonds and hydrophobic interactions may be used to conjugate a dendrimer and a metal chelate. One example bifunctional chelator is p-SCN-Bn-CHX-A"-DTPA (Macrocyclics, P/N B-355). Other exemplary bifunctional chelators include Maleimido-mono-amide-DTPA (Macrocyclics, P/N B-372) and p-SCN-Bn-DTPA (Macrocyclics, P/N B-305). One example of a chelating agent is DTPA. Other examples include DOTA, NOTA, and DFO.

Breast cancer: A neoplastic tumor of breast tissue that is or has potential to be malignant. The most common type of breast cancer is breast carcinoma, such as ductal carcinoma. Ductal carcinoma in situ is a non-invasive neoplastic condition of the ducts. Lobular carcinoma is not an invasive disease but is an indicator that a carcinoma may develop. Infiltrating (malignant) carcinoma of the breast can be divided into stages (I, IIA, IIB, IIIA, IIIB, and IV). See, for example, Bonadonna et al., (eds), Textbook of Breast Cancer: A clinical Guide the Therapy, $3^{rd}$; London, Tayloy & Francis, 2006.

Cancer, Tumor, and Neoplasia: A neoplasm is an abnormal growth of tissue or cells that results from excessive cell division. Neoplastic growth can produce a tumor. The amount of a tumor in an individual is the "tumor burden" which can be measured as the number, volume, or weight of the tumor. A tumor that does not metastasize is referred to as "benign." A tumor that invades the surrounding tissue or can metastasize (or both) is referred to as "malignant." Cancer is a malignant neoplasm that has undergone characteristic anaplasia with loss of differentiation, increased rate of growth, invasion of surrounding tissue, and is capable of metastasis.

Tumors of the same tissue type are primary tumors originating in a particular organ (such as colon, skin, breast, prostate, bladder or lung). Tumors of the same tissue type may be divided into tumors of different sub-types. For examples, lung carcinomas can be divided into an adenocarcinoma, small cell, squamous cell, or non-small cell tumors.

Examples of solid tumors, such as sarcomas (connective tissue cancer) and carcinomas (epithelial cell cancer), include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colorectal carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma).

Carcinoma: A malignant tumor including transformed epithelial cells. Non-limiting examples of carcinomas include adenocarcinoma, squamous cell carcinoma, anaplastic carcinoma and large and small cell carcinoma. In some examples, a carcinoma is a breast carcinoma, colorectal carcinoma, lung carcinoma or melanoma.

Colorectal cancer: A neoplastic tumor of colon, rectum or anus tissue that is or has the potential to be malignant. The main types of colorectal cancer include colorectal carcinomas such as adenocarcinoma and squamous cell carcinoma. Infiltrating (malignant) carcinoma of the colon can be divided into stages (I, II, III and IV). See, for example, Blake et al. (eds.), Gastrointestinal Oncology: A practical Guide, Berlin: Springer-Verlag, 2011.

Conditions sufficient to form an immune complex: Conditions which allow an antibody to bind to its cognate epitope to a detectably greater degree than, and/or to the substantial exclusion of, binding to substantially all other epitopes. Conditions sufficient to form an immune complex are dependent upon the format of the binding reaction and typically are those utilized in immunoassay protocols or those conditions encountered in vivo. See Greenfield (Ed.), *Antibodies: A Laboratory Manual,* $2^{nd}$ ed. New York: Cold Spring Harbor Laboratory Press, 2014, for a description of immunoassay formats and conditions. The conditions employed in the methods are "physiological conditions" which include reference to conditions (e.g., temperature, osmolarity, pH) that are typical inside a living mammal or a mammalian cell. While it is recognized that some organs are subject to extreme conditions, the intra-organismal and intracellular environment normally lies around pH 7 (e.g., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

The formation of an immune complex can be detected through conventional methods, for instance immunohistochemistry (IHC), immunoprecipitation (IP), flow cytometry, immunofluorescence microscopy, ELISA, immunoblotting (for example, Western blot), magnetic resonance imaging (MRI), computed tomography (CT) scans, radiography, and affinity chromatography.

Contacting: Placement in direct physical association; includes both in solid and liquid form.

Control: A reference standard. In some aspects, the control is a negative control, such as sample obtained from a subject that does not have cancer or a tissue sample from a tissue that is non-cancerous. In other aspects, the control is a positive control, such as a tissue sample obtained from a patient diagnosed with cancer or a tissue sample from a cancerous tissue. In still other aspects, the control is a historical control or standard reference value or range of values (such as a previously tested control sample, such as a group of cancer patients with known prognosis or outcome, or group of samples that represent baseline or normal values).

A difference between a test sample and a control can be an increase or conversely a decrease. The difference can be a qualitative difference or a quantitative difference, for example a statistically significant difference. In some examples, a difference is an increase or decrease, relative to a control, of at least about 5%, such as at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, or at least about 500%.

Copper-64 ($^{64}Cu$): A radioisotope of copper with a half-life of 12.7 hours. PubChem CID: 105141.

Deferoxamine (DFO): A chelator with chemical formula $C_{25}H_{48}N_6O_8$. Also known as Desferrioxamine. CAS RN: 70-51-9. PubChem CID: 2973. IUPAC name: N-[5-[[4-[5-[acetyl(hydroxy)amino]pentylamino]-4-oxobutanoyl]-hydroxyamino]pentyl]-N'-(5-aminopentyl)-N'-hydroxybutanediamide. In one example DFO chelates $^{89}Zr$. In another example DFO is conjugated to a monoclonal antibody by incubating the monoclonal antibody with p-SCN-Bn-Deferoxamine.

Detectable marker: A detectable molecule (also known as a label) that is conjugated directly or indirectly to a second molecule, such as an antibody, to facilitate detection of the second molecule. For example, the detectable marker can be capable of detection by ELISA, spectrophotometry, flow cytometry, gamma detection, near-infrared imaging, microscopy or diagnostic imaging techniques (such as CT scans, MRIs, ultrasound, fluorescence imaging, fiberoptic examination, and laparoscopic examination). Specific, non-limiting examples of detectable markers include fluorophores, chemiluminescent agents, enzymatic linkages, radioactive isotopes (for example $^{111}In$) and heavy metals or compounds (for example super paramagnetic iron oxide nanocrystals for detection by MRI). Other examples of detectable markers include, but are not limited to, the following: radioisotopes (radioactive isotopes) (such as $^3H$, $^{35}S$, $^{32}P$, $^{14}C$, $^{125}I$, $^{11}C$, $^{15}O$, $^{13}N$, $^{76}Br$, $^{123}I$, $^{124}I$, $^{131}I$, $^{89}Zr$, $^{64}Cu$, $^{99m}Tc$ or $^{111}In$), radionucleotides, fluorescent labels (such as fluorescein isothiocyanate (FITC), rhodamine, lanthanide phosphors, or 800CW dye), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some aspects, labels are attached by spacer arms of various lengths to reduce potential steric hindrance. Methods for using detectable markers and guidance in the choice of detectable markers appropriate for various purposes are discussed for example in Green and Sambrook (*Molecular Cloning: A Laboratory Manual,* 4$^{th}$ ed., New York: Cold Spring Harbor Laboratory Press, 2012) and Ausubel et al. (Eds.) (*Current Protocols in Molecular Biology*, New York: John Wiley and Sons, including supplements, 2017).

Detecting: To identify the existence, presence, or fact of something. Included herein are methods of detecting a GD2 expressing cancer.

Diethylenetriaminepentaacetic acid (DTPA): A chelating agent with molecular formula $C_{14}H_{23}N_3O_{10}$. Also commonly known as Pentetic acid. CAS RN: 67-43-6. PubChem CID: 3053. IUPAC name: 2-[bis [2-[bis(carboxymethyl) amino]ethyl]amino]acetic acid. DTPA can chelate a variety of metals, including but not limited to radioisotopes. In one example DTPA can chelate the radioisotope 111 In. In an additional example DTPA can be conjugated to an antibody by incubating p-SCN-Bn-CHX-A"-DTPA and that antibody. p-SCN-Bn-CHX-A"-DTPA has the chemical formula $C_{26}H_{34}N_4O_{10}S\cdot 3HCl$. CAS RN: 157380-45-5. PubChem CID: 15045032. IUPAC name: 2-[[(1R,2R)-2-[bis(carboxymethyl)amino]cyclohexyl]-[(2S)-2-[bis(carboxymethyl)amino]-3-(4-isothiocyanatophenyl) propyl]amino] acetic acid.

Dinutuximab: A chimeric monoclonal antibody that specifically binds to GD2. Dinutuximab has human IgG1 heavy and light chain constant regions (γ1 heavy chain and κ light chain) with variable regions of the GD2-specific murine antibody 14.18. The dinutuximab heavy and light chain sequences are provided herein as SEQ ID NOs: 1 and 2, respectively. As used herein, the term 'dinutuximab' is inclusive of monoclonal antibody produced in SP2/0 cells (dinutuximab) as well as monoclonal antibody produced by the same plasmid but in CHO cells (dinutuximab-beta).

Dodecane tetraacetic acid (DOTA): A chelating agent with molecular formula $C_{16}H_{28}N_4O_8$. Also known as tetraxetan, dota acid, and 1,4,7,10-Tetraazacyclododecane-1,4,7,10-tetraacetic acid. CAS RN: 60239-18-1. PubChem CID: 121841. IUPAC name: 2-[4,7,10-tris(carboxymethyl)-1,4,7,10-tetrazacyclododec-1-yl]acetic acid. In one example DOTA chelates $^{111}In$. In another example DOTA chelates $^{64}Cu$. In a further example DOTA is conjugated to a monoclonal antibody by incubating the monoclonal antibody with p-SCN-Bn-DOTA.

Effective amount: A quantity of a specific substance sufficient to achieve a desired effect in a subject to whom the substance is administered. For instance, this can be the amount of an antibody-conjugate sufficient for the detection of gamma rays and/or fluorescence from antibody-conjugate bound to GD2 positive cells by a handheld gamma probe or a handheld near infrared fluorescent camera.

In some aspects, administration of an effective amount of an antibody-conjugate that binds to GD2 can identify the presence or absence of GD2 positive cancer (for example, as measured by the presence or absence of GD2 expressing cells in a subject's tissue; in one aspect the presence or absence of GD2 expressing cells is ascertained by measuring the presence of a detectable marker forming part of the antibody-conjugate) by a desired amount.

The effective amount of an antibody-conjugate that specifically binds GD2 that is administered to a subject to identify GD2 expressing cancer will vary depending upon a number of factors associated with that subject, for example the overall health and/or weight of the subject. An effective amount can be determined by varying the dosage and measuring the resulting response, such as, for example, detecting the presence of gamma signal in the subject administered the antibody-conjugate. Effective amounts also can be determined through various in vitro, in vivo or in situ immunoassays.

An effective amount encompasses a fractional dose that contributes in combination with previous or subsequent administrations to attaining an effective response. For example, an effective amount of an agent can be administered in a single dose, or in several doses, for example daily, during a course of treatment lasting several days or weeks. However, the effective amount can depend on the subject being treated, the severity and type of the condition being treated, and the manner of administration. A unit dosage form of the agent can be packaged in an amount, or in multiples of the effective amount, for example, in a vial (e.g., with a pierceable lid) or syringe having sterile components.

Epitope: An antigenic determinant. These are particular chemical groups or peptide sequences on a molecule that are antigenic, i.e. that elicit a specific immune response. An antibody specifically binds a particular antigenic epitope on a polypeptide. In some examples a disclosed antibody specifically binds to an epitope on GD2.

Ewing's sarcoma: A rare type of malignant tumor found in bone or soft tissue. Ewing's sarcoma is a small, blue, round cell tumor.

Ganglioside G2 (GD2): A disianganglioside that can be expressed by neurons, skin melanocytes, and peripheral sensory nerve fibers.

GD2-positive cancer: A cancer that expresses or overexpresses cell-surface GD2. Examples of GD2-positive cancers include, but are not limited to, neuroblastoma, melanoma, osteosarcoma, retinoblastoma, Ewing sarcoma, small cell lung cancer, glioma, soft tissue sarcoma, and breast cancer.

Glioma: A tumor composed of neuroglia in any developmental state. Gliomas include all intrinsic neoplasms of the brain and spinal cord, such as astrocytomas, ependymomas, and oligodendrogliomas. "Low-grade" gliomas are well-differentiated (not anaplastic); these are benign and portend a better prognosis for the patient. "High-grade" gliomas are undifferentiated or anaplastic; these are malignant and carry a worse prognosis.

IgG: A polypeptide belonging to the class or isotype of antibodies that are substantially encoded by a recognized immunoglobulin gamma gene. In humans, this class comprises $IgG_1$, $IgG_2$, $IgG_3$, and $IgG_4$.

Immune complex: The binding of antibody to a soluble antigen forms an immune complex. The formation of an immune complex can be detected through conventional methods, for instance immunohistochemistry, immunoprecipitation, flow cytometry, immunofluorescence microscopy, ELISA, immunoblotting (for example, Western blot), magnetic resonance imaging, CT scans, radiography, and affinity chromatography.

Indium-111 ($^{111}$In or In-111): a radioactive isotope of indium with 49 protons and 62 neutrons. $^{111}$In decays by gamma emission with a $t_{1/2}$ of 2.81 days. Indium is a low-energy emission radioisotope. PubChem CID: 5462099.

IR 700 Dye: A near infrared dye with excitation/emission of about 685/705 nm. Commercial sources of IR 700 dye are available for example, Li-Cor® IRDye® 700, available as IRDye® 700DX NHS ester (P/N 929-70010), IRDye® 700 Phosphoramidite (P/N: 4200-33), and IRDye® 700 AP-1 Consensus Oligonucleotide (P/N: 829-07925). Another commercial vendor is Integrated DNA Technologies®, available as 5' IRDye® 700 (Mod Code: 5IRD700).

Antibody conjugates of IR 700 dye can induce targeted cell death, such as targeted tumor cell death, after exposure to near infrared light in the excitation range. See Mitsunaga et al., *Nat Med* 17 (12): 1685-1691, 2011. In some examples, IR 700 dye can be conjugated to an antibody, which is also conjugated to a distinct near-infrared fluorescent dye (such as 800CW Dye) and a chelator (such as DTPA).

Isolated: A biological component (such as a nucleic acid, peptide, protein or protein complex, for example an antibody) that has been substantially separated, produced apart from, or purified away from other biological components in the cell of the organism in which the component naturally occurs, that is, other chromosomal and extra-chromosomal DNA and RNA, and proteins. Thus, isolated nucleic acids, peptides and proteins include nucleic acids and proteins purified by standard purification methods. The term also embraces nucleic acids, peptides and proteins prepared by recombinant expression in a host cell, as well as, chemically synthesized nucleic acids. An isolated nucleic acid, peptide or protein, for example an antibody, can be at least 50%, at least 60%, at least 70%, at least 80%, at least 90%, at least 95%, at least 96%, at least 97%, at least 98%, or at least 99% pure.

Linker: A bi-functional molecule that can be used to link two molecules into one contiguous molecule, for example, to link a detectable molecule to an antibody. Non-limiting examples of peptide linkers include glycine-serine linkers.

The terms "conjugating," "joining," "bonding," or "linking" can refer to making two molecules into one contiguous molecule; for example, linking two polypeptides into one contiguous polypeptide, or covalently attaching an effector molecule or detectable marker radionuclide or other molecule to a polypeptide, such as an scFv. The linkage can be either by chemical or recombinant means. "Chemical means" refers to a reaction between the antibody moiety and the detectable molecule such that there is a covalent bond formed between the two molecules to form one molecule.

Lung cancer: A neoplastic tumor of lung tissue that is or has the potential to be malignant. The main types of lung cancer are lung carcinomas: adenocarcinoma, small cell carcinoma, squamous cell carcinoma, or non-small cell carcinoma. Lung cancer is typically staged from I to IV; other classifications are also used, for example small-cell lung carcinoma can be classified as limited stage if it is confined to one half of the chest and within the scope of a single radiotherapy field; otherwise, it is extensive stage. See, for example, Hansen (ed.), Textbook of Lung Cancer, $2^{nd}$, London: Informa Healthcare, 2008.

Neuroblastoma: A solid tumor arising from embryonic neural crest cells. Neuroblastoma commonly arises in and around the adrenal glands, but can occur anywhere that sympathetic neural tissue is found, such as in the abdomen, chest, neck or nerve tissue near the spine. Neuroblastoma typically occurs in children younger than 5 years of age.

NOTA: A chelating agent with molecular formula $C_{12}H_{21}N_3O_6$. Also known as 2-[4,7-bis(carboxymethyl)-1,4,7-triazonan-1-yl]acetic acid, 1,4,7-Triazacyclononane-N,N',N"-triacetic acid, or 2,2',2"-(1,4,7-triazonane-1,4,7-triyl) triacetic acid. CAS RN: 56491-86-2. PubChem CID: 124326. IUPAC name: 2-[4,7-bis(carboxymethyl)-1,4,7-triazonan-1-yl]acetic acid. In one example NOTA can chelate the radioisotope $^{64}$Cu. In another example NOTA is conjugated to a monoclonal antibody by incubating p-SCN-Bn-NOTA with the monoclonal antibody.

Osteosarcoma: A type of cancerous tumor found in the bone. Osteosarcoma is an aggressive cancer arising from primitive transformed cells of mesenchymal origin. This type of cancer is most prevalent in children and young adults.

Pharmaceutically acceptable carriers: The pharmaceutically acceptable carriers of use are conventional. *Remington: The Science and Practice of Pharmacy, $22^{nd}$ ed.*, London, UK: Pharmaceutical Press, 2013, describes compositions and formulations suitable for pharmaceutical delivery of the antibody-conjugates and other compositions disclosed herein. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polyhistidine-tag: an amino acid motif including at least six histidines. Polyhistidine-tags can be used to chelate a radioisotope such as Tc-99m. See Waibel et al., Nat. Biotech. (1999) 17:897-901. Polyhistidine-tags are commercially available from sources such as GenScript recombinant protein services. Hexahistidine-tag (6 histidines) is an exemplary polyhistidine-tag.

Purified: The term purified does not require absolute purity; rather, it is intended as a relative term. Thus, for example, a purified peptide preparation is one in which the peptide or protein (such as an antibody) is more enriched than the peptide or protein is in its natural environment within a cell. In one aspect, a preparation is purified such that the protein or peptide represents at least 50% of the total peptide or protein content of the preparation.

Radioguided Surgery (RGS): Utilizing emissions from radioisotopes to localize regions of interest. In one aspect gamma emissions are used to localize regions of interest. In another aspect radio-guided surgery is used for a sentinel lymph node biopsy in melanoma and breast cancer. In another aspect radio-guided surgery facilitates the surgical resection of cancer. In another aspect radio-guided surgery is used to identify lesions and localization of occult tumor metastases.

Retinoblastoma: A type of cancer that forms in the tissues of the retina. Retinoblastoma usually occurs in children younger than 5 years. It may be hereditary or nonhereditary (sporadic).

Sequence identity: The identity between two or more nucleic acid sequences, or two or more amino acid sequences, is expressed in terms of the identity between the sequences. Sequence identity can be measured in terms of percentage identity; the higher the percentage, the more identical the sequences. Homologs and variants of a $V_L$ or a $V_H$ of an antibody that specifically binds a target antigen are typically characterized by possession of at least about 75% sequence identity, for example at least about 80%, 85%, 90%, 91%, 92%, 93%, 94%, 95%, 96%, 97%, 98% or 99% sequence identity counted over the full-length alignment with the amino acid sequence of interest.

Any suitable method may be used to align sequences for comparison. Non-limiting examples of programs and alignment algorithms are described in: Smith and Waterman, *Adv. Appl. Math.* 2(4): 482-489, 1981; Needleman and Wunsch, *J. Mol. Biol.* 48(3): 443-453, 1970; Pearson and Lipman, *Proc. Natl. Acad. Sci. U.S.A.* 85(8): 2444-2448, 1988; Higgins and Sharp, Gene, 73(1): 237-244, 1988; Higgins and Sharp, *Bioinformatics,* 5(2): 151-3, 1989; Corpet, *Nucleic Acids Res.* 16(22): 10881-10890, 1988; Huang et al. *Bioinformatics,* 8(2): 155-165, 1992; and Pearson, *Methods Mol. Biol.* 24:307-331, 1994. Altschul et al., *J. Mol. Biol.* 215(3): 403-410, 1990, presents a detailed consideration of sequence alignment methods and homology calculations. The NCBI Basic Local Alignment Search Tool (BLAST) (Altschul et al., *J. Mol. Biol.* 215(3): 403-410, 1990) is available from several sources, including the National Center for Biological Information and on the Internet, for use in connection with the sequence analysis programs blastp, blastn, blastx, tblastn, and tblastx. Blastn is used to compare nucleic acid sequences, while blastp is used to compare amino acid sequences. Additional information can be found at the NCBI web site.

Generally, once two sequences are aligned, the number of matches is determined by counting the number of positions where an identical nucleotide or amino acid residue is present in both sequences. The percent sequence identity between the two sequences is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100.

Skin cancer: A neoplastic tumor of skin tissue that is or has the potential to be malignant. Melanoma is a skin cancer of transformed melanocytes (cells that make the pigment melanin). Melanocytes are found primary in the skin, but are also present in the bowel and eye. Melanoma in the skin includes superficial spreading melanoma, nodular melanoma, acral lentiginous melanoma, and lentigo maligna (melanoma). Any of the above types may produce melanin or can be amelanotic. Similarly, any subtype may show desmoplasia (dense fibrous reaction with neurotropism), which is a marker of aggressive behavior and a tendency for local recurrence. Other melanomas include clear cell sarcoma, mucosal melanoma and uveal melanoma. Melanoma is staged from I to IV. See, for example, Thompson et al. (eds), Textbook of Melanoma: Pathology, Diagnosis and Management, London: Taylor & Francis, 2004.

Small cell lung cancer (SCLC): Also called oat cell carcinoma SCLC tends to arise in the larger airways (primary and secondary bronchi) and grows rapidly, becoming quite large. The "oat" cell contains dense neurosecretory granules (vesicles containing neuroendocrine hormones), which give this an endocrine/paraneoplastic syndrome association. While initially more sensitive to chemotherapy, it ultimately carries a worse prognosis and is often metastatic at presentation. Small cell lung cancers are divided into limited stage and extensive stage disease. This type of lung cancer also is strongly associated with smoking.

Specifically bind: When referring to an antibody or antibody-conjugate, refers to a binding reaction which determines the presence of a target protein in the presence of a heterogeneous population of proteins and other biologics. Thus, under designated conditions, an antibody binds preferentially to a particular target protein, peptide or polysaccharide (such as an antigen present on the surface of a cancer, such as GD2) and does not bind in a significant amount to other proteins present in the sample or subject. Specific binding can be determined by standard methods. See Harlow & Lane, *Antibodies, A Laboratory Manual,* 2$^{nd}$ ed., Cold Spring Harbor Publications, New York (2013), for a description of immunoassay formats and conditions that can be used to determine specific immunoreactivity.

An antibody that specifically binds to GD2 is an antibody that binds substantially to GD2, including cells or tissue expressing GD2, substrate to which the GD2 is attached, or GD2 in a biological specimen. It is, of course, recognized that a certain degree of non-specific interaction may occur between an antibody and a non-target (such as a cell that does not express GD2). Typically, specific binding results in a much stronger association between the antibody and protein or cells bearing the antigen than between the antibody and protein or cells lacking the antigen. Specific binding typically results in greater than 2-fold, such as greater than 5-fold, greater than 10-fold, or greater than 100-fold increase in amount of bound antibody (per unit time) to a protein including the epitope or cell or tissue expressing the target epitope as compared to a protein or cell or tissue lacking this epitope. Specific binding to a protein under such conditions requires an antibody that is selected for its specificity for a particular protein. A variety of immunoassay formats are appropriate for selecting antibodies or other ligands specifically immunoreactive with a particular protein. For example, solid-phase ELISA immunoassays are routinely used to select monoclonal antibodies specifically immunoreactive with a protein.

Subject: Living multi-cellular vertebrate organisms, a category that includes human and non-human mammals. In an example, a subject is a human. In an additional example, a subject is selected that is in need of treatment for GD2 positive cancer. In one example the subject has been diagnosed with GD2 positive cancer. In an additional example the subject is suspected of having GD2 positive cancer.

Technetium-99m ($^{99m}$Tc): A radioisotope of technetium with a half-life of approximately 6 hours. PubChem CID: 26476.

Tumor burden: The total volume, number, metastasis, or combinations thereof of tumor or tumors in a subject.

Zirconium-89 ($^{89}$Zr): A radioisotope of zirconium with a half life of approximately 3.3 days. PubChem CID: 109374074.

III. Overview

Surgical resection is often utilized for the management of high-risk neuroblastoma. Achieving resection safely is challenging, as these tumors are poorly circumscribed, develop an intimate relationship with vital structures that must be preserved, and can form satellite lesions that are difficult to find. Guided by direct tumor visualization and palpation, inadequate surgery rates for high-risk neuroblastoma are up to 30%, and up to 50% suffer significant surgery-related complications. The tumor antigen-specific tracers disclosed herein permit visualize neuroblastoma in a surgical environment.

The use of at least two probes as disclosed herein permits detection of deeper tumors (RGS) and margin visualization (FGS). DTPA-αGD2-IRDye800CW was synthesized and radiolabeled with Indium-111. While the binding affinity of DTPA-αGD2-IRDye800CW is 10-fold lower than unlabeled antibody (21.31 nM versus 2.39 nM), it remains adequate for intraoperative imaging.[37] In biodistribution studies, the probe had excellent tumor-to-background ratios four days after injection, including a tumor-to-blood ratio of 3.87 and a tumor-to-muscle ratio of 30.0. As with other antibody-based IMI probes, there was non-specific accumulation in the liver (tumor-to-liver ratio of 1.32) and spleen (tumor-to-spleen ratio of 1.76). While the addition of 10× unlabeled antibody did not block probe from accumulating in the tumor, this is likely due to a large antigen sink that was not sufficiently occupied by unlabeled antibody.[38] Similar results were seen in a fluorescence biodistribution three days after probe injection, where average fluorescence intensity was significantly higher in tumor versus all other organs except for the liver, with a comparable tumor-to-muscle ratio of 4.5. Furthermore, the tumor was detectable in vivo with the Neoprobe and SPY-PHI NIR camera.

The effect of tumor depth on detection was assessed with a processed tissue model. Gamma detection of the labeled tumor was excellent at 5 cm of intervening processed tissue. Gamma detection provided directional guidance, helpful for surgeons performing dissection, as counts were highest when the probe was on an axis pointed directly towards the tumor. Changing this axis, by even 5 degrees resulted in a significant drop in signal strength. Using conventional methods, identifying a tumor more than 2 cm below an organ surface is exceedingly difficult. By comparison, fluorescent detection was significantly limited by depth, only visible through 5 mm or less of tissue.

Mice with xenograft neuroblastomas were injected with the tracer and complete tumor resection was faithfully attempted without IMI guidance (standard surgery); however, imaging with the SPY-PHI revealed presumed residual disease that was not appreciated during the initial white-light resection. The residual fluorescent tissue was then resected under IMI guidance. These findings support the use of IMI to help surgeons localize occult or residual disease and facilitate a more complete resection with a potential benefit on patient survival. Moreover, the IMI tracers disclosed herein are detectable with excellent sensitivity and specificity.

Some examples make use of a murine anti-GD2 antibody. The use of the FDA-approved chimeric antibody, Dinutuximab is further contemplated herein. Dinutuximab possesses the same variable regions ($V_H$ and $V_L$), establishing the utility of the anti-GD2 targeting strategy.

Disclosed herein is an antibody-conjugate, including a monoclonal antibody and/or antigen binding fragment thereof-conjugated to a near-infrared fluorescent dye and a chelator. In some examples, the monoclonal antibody and/or antigen binding fragment specifically binds to Ganglioside G2 (GD2) and includes a heavy chain and a light chain including heavy and light chain variable regions set forth as SEQ ID NOs: 3 and 4, respectively. In some examples, the antibody-conjugate specifically binds to GD2. In a further specific example, the antibody-conjugate includes the monoclonal antibody. In some examples, the antibody's heavy chain and light chain include SEQ ID NOs: 1 and 2, respectively. In another specific example, the antibody-conjugate includes the antigen binding fragment. In some examples, the antigen binding fragment is a Fv, Fab, Fab', $F(ab')_2$, scFV, $scFV_2$, diabody, and/or minibody fragment. In some examples, the chelator includes DTPA, DOTA, NOTA, and/or DFO. In a specific example, the chelator is DTPA. In further examples, the antibody-conjugate includes a radioisotope chelated by the chelator, such as Indium-111 ($^{111}$In), Copper-64 ($^{64}$Cu), Zirconium-89 ($^{89}$Zr), or Technetium-99m ($^{99m}$Tc). In a specific example, the radioisotope is $^{111}$In. In a further specific example the near-infrared fluorescent dye includes 800CW dye. In some examples, the monoclonal antibody or antigen binding fragment is conjugated to an additional anti-cancer agent, such as IR700.

In some examples, the antibody-conjugate includes about 1-5 fluorescent dye molecules and/or about 1-3 chelator molecules per monoclonal antibody and/or antigen binding fragment. In further examples, the antibody-conjugate includes about 1-3 fluorescent dye molecules and/or about 1-2 DTPA molecules per monoclonal antibody and/or antigen binding fragment. In further examples, the antibody-conjugate includes about 1.5-3 fluorescent dye molecules and/or about 0.5-2 DTPA molecules per monoclonal antibody or antigen binding fragment. In some examples the antibody-conjugate includes about 2-2.5 fluorescent dye molecules and/or about 1 to 1.5 DTPA molecules per monoclonal antibody and/or antigen binding fragment. In some examples, the antibody-conjugate has a molar ratio of the monoclonal antibody and/or antigen binding fragment to the DTPA of about 1:1.5 to about 1:2 and/or a molar ratio of the monoclonal antibody and/or antigen binding fragment to the fluorescent dye of about 1:1 to about 1:3. In further examples the antibody-conjugate has a molar ratio of the monoclonal antibody and/or antigen binding fragment to the DTPA of about 1:1 to about 1:1.5 and/or a molar ratio of the monoclonal antibody and/or antigen binding fragment to the fluorescent dye of about 1:2 to about 1:2.5. In further examples, the antibody-conjugate has a molar ratio of the monoclonal antibody or antigen binding fragment to the DTPA of about 1:0.5 to about 1:2 and/or a molar ratio of the monoclonal antibody or antigen binding fragment to the fluorescent dye of about 1:1.5 to about 1:3.

In some examples, the monoclonal antibody or antigen binding fragment conjugated to a near-infrared fluorescent dye has chemical structure 1 where R is the monoclonal antibody or antigen binding fragment:

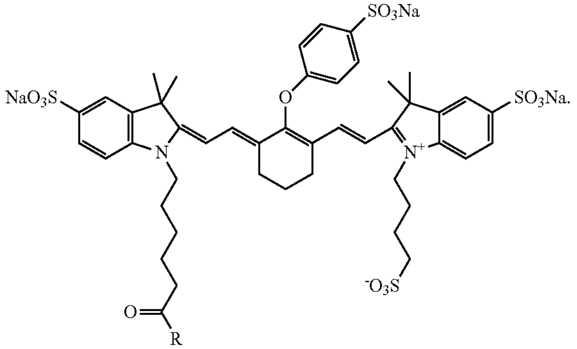

In some examples, the monoclonal antibody or antigen binding fragment is conjugated via covalent bond to the fluorescent dye and the chelator.

Further disclosed herein is a composition for use in identifying or treating GD2 positive cancer in a subject, including the antibody-conjugates described above, and optionally, a pharmaceutically acceptable carrier.

Also disclosed herein is a method of identifying GD2 positive cancer tissue in a subject, including administering to the subject an amount of the antibody-conjugate disclosed above effective to label the GD2-positive cancer tissue in the subject. In some examples the subject is suspected of having a GD2 positive cancer. Further disclosed herein is a method of treating a GD2 positive cancer tissue in a subject, including administering to the subject a therapeutically effective amount of the antibody-conjugate disclosed above. In some examples, the subject is suspected of having a GD2 positive cancer. In some examples, the subject is a human subject. In some examples, the GD2 positive cancer includes neuroblastoma, melanoma, osteosarcoma, retinoblastoma, Ewing sarcoma, small cell lung cancer, glioma soft tissue sarcoma, and/or breast cancer. In a specific example, the GD2 positive cancer is neuroblastoma. In some examples, the methods of treating or identifying a GD2 positive cancer tissue include surgically resecting some or all of the labeled GD2-positive cancer tissue, such as at least 10%, at least 20%, at least 30%, at least 40%, at least 50%, at least 60%, at least 70%, at least 80%, at least 90%, at least 95%, at least 99%, or 100% of the GD2-positive cancer tissue.

Disclosed herein is a method of producing the antibody conjugates disclosed above, including incubating a monoclonal antibody or antigen binding fragment with a near-infrared fluorescent dye and diethylenetriaminepentaacetic acid (DTPA) under conditions sufficient to conjugate the near-infrared fluorescent dye and the DTPA to the monoclonal antibody or antigen binding fragment, to produce the antibody-conjugate. In some examples, the antibody-conjugate has a molar ratio of monoclonal antibody and/or antigen binding fragment to DTPA of about 1:1.5 to about 1:2 and/or the antibody-conjugate has a molar ratio of monoclonal antibody and/or antigen binding fragment to near-infrared fluorescent dye of about 1:1 to about 1:3. In some examples, the antibody-conjugate has a molar ratio of monoclonal antibody and/or antigen binding fragment to DTPA of about 1:1 to about 1:1.5 and/or the antibody-conjugate has a molar ratio of monoclonal antibody and/or antigen binding fragment to near-infrared fluorescent dye of about 1:2 to about 1:2.5. In some examples, the antibody-conjugate has a molar ratio of monoclonal antibody and/or antigen binding fragment to DTPA of about 1:0.5 to about 1:2 and/or the antibody-conjugate has a molar ratio of monoclonal antibody and/or antigen binding fragment to near-infrared fluorescent dye of about 1:1.5 to about 1:3. In some examples, the method further includes incubating 111 In with the antibody-conjugate under conditions sufficient for the DTPA to chelate the 111 In.

Also disclosed are kits for identifying GD2 positive cancer in a subject, including: a container including the antibody-conjugate of any one of claims 1-17 and instructions for using the kit. In some examples, the kit includes a monoclonal antibody or antigen binding fragment, a near-infrared fluorescent dye, and/or a chelator in separate containers, which are configured to be mixed.

Further disclosed is a method producing an antibody-conjugate including incubating a monoclonal antibody or antigen binding fragment with diethylenetriaminepentaacetic acid (DTPA) under conditions sufficient to conjugate the DTPA to the monoclonal antibody or antigen binding fragment, thereby producing a monoclonal antibody or antigen binding fragment conjugated to DTPA. In some examples, the method includes incubating the monoclonal antibody or antigen binding fragment conjugated to DTPA with an 800CW dye under conditions sufficient to conjugate the 800CW dye to the monoclonal antibody or antigen binding fragment conjugated to DTPA, thereby producing a monoclonal antibody or antigen binding fragment conjugated to DTPA and 800CW dye. In further examples, the method includes incubating the monoclonal antibody or antigen binding fragment conjugated to DTPA and the 800CW dye with a radioisotope under conditions sufficient to chelate the radioisotope to the monoclonal antibody or antigen binding fragment conjugated to DTPA and 800CW dye, thereby producing the antibody-conjugate. In a specific example, the monoclonal antibody or antigen binding fragment specifically binds to Ganglioside G2 (GD2) and includes a heavy chain and a light chain including heavy and light chain variable regions set forth as SEQ ID NOs: 3 and 4, respectively and the radioisotope includes Indium-111. In some examples, the antibody-conjugate has a molar ratio of monoclonal antibody and/or antigen binding fragment to DTPA of about 1:1 to about 1:1.5. In some examples the antibody-conjugate has a molar ratio of monoclonal antibody and/or antigen binding fragment to DTPA of about 1:0.5 to about 1:2. In further examples, the antibody-conjugate has a molar ratio of monoclonal antibody to near-infrared fluorescent dye of about 1:2 to about 1:2.5. In some examples the antibody-conjugate has a molar ratio of monoclonal antibody to near-infrared fluorescent dye of about 1:1.5 to about 1:3. In further examples the antibody-conjugate has a ratio of radioisotope to monoclonal antibody and/or antigen binding fragment conjugated to DTPA and/or the 800CW dye of about 1.5 microcurie: 1 μg to about 2.5 microcurie: 1 μg.

In some examples, the conditions sufficient to conjugate the DTPA to the monoclonal antibody and/or antigen binding fragment include about 9 pH and/or about 15 to about 50 molar excess of DTPA. In a specific example, the conditions sufficient to conjugate the DTPA to the monoclonal antibody or antigen binding fragment include about 15- to 25-fold molar excess of DTPA. In some examples, the conditions sufficient to conjugate the 800CW dye to the monoclonal antibody or antigen binding fragment conjugated to DTPA include about 9 pH and/or about 3 to about 5 molar excess of 800CW dye. In a specific example, the conditions sufficient to conjugate the 800CW dye to the monoclonal antibody or antigen binding fragment conjugated to DTPA about 4 molar excess of 800CW dye. In some examples, the conditions sufficient to chelate the radioisotope to the monoclonal antibody or antigen binding fragment conjugated to DTPA and 800CW dye include about 6 pH. In some examples, the conditions sufficient to chelate the radioisotope to the monoclonal antibody or antigen binding fragment conjugated to DTPA and/or 800CW dye include a ratio of about 1 millicurie radioisotope: 300 μg monoclonal antibody and/or antigen binding fragment conjugated to DTPA and/or 800CW dye to about 1 millicurie radioisotope: 600 μg monoclonal antibody or antigen binding fragment conjugated to DTPA and/or 800CW dye. In some examples, the DTPA includes IRDye800CW-NHS. In some examples the 800CW dye includes 800CW dye-NHS.

IV. Description of Several Aspects

Provided are antibody-conjugates that specifically bind to GD2, and methods of use thereof. The antibody-conjugate includes a monoclonal antibody that specifically binds to GD2, which is conjugated to a near-infrared fluorescent dye and a chelating agent, such as diethylenetriaminepentaacetic acid (DTPA). In several aspects, the antibody-conjugate further comprises Indium-111 ($^{111}In$) chelated by the DTPA. The antibody-conjugate is useful, for example, for detection of GD2 positive tumor cells, delineation of GD2-positive tumor borders, visual mapping of the primary GD2-positive tumor bed, or the detection of occult GD2-positive tumor lesions.

The monoclonal antibody in the antibody-conjugate specifically binds to the extracellular domain of GD2 present on the cell surface. Antibodies that specifically bind to the GD2 extracellular domain are available, including those that have been derived from the IgG3 murine monoclonal antibody 14.18. Mouse IgG isotype switch variant hybridomas derived from that clone include 14G1 (IgG1), 14G2a (IgG2a; sold by BioXCell Cat #BE0318), and 14G2b (IgG2b). A chimeric variant of 14.18, called ch14.18, with human IgG1 heavy and light chain constant regions (γ1 heavy chain and κ light chain) with the murine 14.18 variable regions has been developed to increase the half-life of the antibody in human circulation, decrease immunogenicity, and to elicit increased ADCC and complement-dependent cytotoxicity. This antibody, produced in SP2/0 cells, was approved for sale in the United States by the Food and Drug Administration (FDA) in 2015 (dinutuximab, or Unituxin™ as sold by United Therapeutics Oncology). Antibody produced by the same plasmid but in CHO cells was approved by the European Medicines Agency (EMA) in 2017 (dinutuximab-beta or Qarziba® or Danyelza® as sold by mAbs Therapeutics Inc™). In some aspects, the monoclonal antibody included in the antibody-conjugate is selected from the group consisting of 14G1, 14G2a, 14G2b, dinutuximab, and dinutuximab-beta.

The heavy and light chain variable regions of dinutuximab and dinutuximab-beta are provided herein as SEQ ID NOs: 3 and 4, respectively. The full heavy and light chain sequences of dinutuximab and dinutuximab-beta are provided herein as SEQ ID NOs: 1 and 2, respectively.

In some aspects, the monoclonal antibody included in the antibody-conjugate comprises a heavy chain and a light chain comprising heavy and light chain variable regions set forth as SEQ ID NOs: 3 and 4, respectively. In some aspects, the monoclonal antibody included in the antibody-conjugate comprises a heavy chain and a light chain set forth as SEQ ID NOs: 1 and 2, respectively.

Any suitable means may be used to produce or obtain the monoclonal antibody included in the antibody-conjugate. In some instances, the antibody is obtained from a commercial source. In other instances, one or more nucleic acid molecules encoding the heavy and light chain of the antibody can be expressed in an appropriate host cell and the resulting antibody purified using appropriate procedures. Numerous expression systems are available for expression of proteins including *E. coli*, other bacterial hosts, yeast, and various higher eukaryotic cells such as the COS, CHO, HeLa and myeloma cell lines.

Methods for expression of monoclonal antibody and/or refolding to an appropriate active form, from mammalian cells, and bacteria such as *E. coli* have been described e.g., Harlow and Lane, *Antibodies: A Laboratory Manual, 2nd*, Cold Spring Harbor Laboratory, New York, 2013. Once expressed, the monoclonal antibody can be purified according to standard procedures including ammonium sulfate precipitation, affinity columns, column chromatography, and the like. The antibody-conjugate need not be 100% pure. Once purified, partially or to homogeneity as desired, if to be used therapeutically, the polypeptides should be substantially free of endotoxin.

The monoclonal antibody included in the antibody-conjugate is conjugated to both a near-infrared fluorescent dye and DTPA. Following conjugation of the near-infrared fluorescent dye and metal chelator, the antibody-conjugate retains the GD2-specificity and binding activity of the monoclonal antibody in the antibody-conjugate.

Any near-infrared fluorescent dye suitable for conjugation to a monoclonal antibody and use in vivo may be used. In some examples, the near infrared fluorescent dye is an 800CW dye, such as IRDye800CW dye available from Licor. An exemplary structure of the IRDye800CW dye conjugated to a monoclonal antibody (R) is provided in the following:

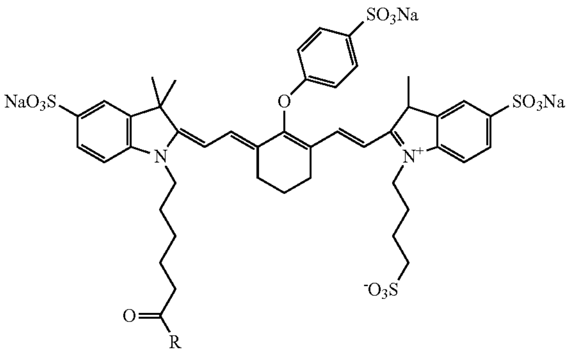

Any suitable means, including covalent and non-covalent attachment means, may be used to conjugate the near-infrared fluorescent dye or the DTPA to the monoclonal antibody. The procedure for attaching a detectable marker to an antibody varies according to the chemical structure. Polypeptides typically contain a variety of functional groups; such as carboxylic acid (COOH), free amine (—$NH_2$) or sulfhydryl (—SH) groups, which are available for reaction with a suitable functional group on the near-infrared fluorescent dye or the DTPA. Alternatively, the antibody is derivatized to expose or attach additional reactive functional groups. The derivatization may involve attachment of any of a number of known linker molecules such as those available from Pierce Chemical Company, Rockford, IL. The linker can be any molecule used to join the antibody to the detectable marker. The linker is capable of forming covalent bonds to both the antibody and to the detectable marker. Suitable linkers include, but are not limited to, straight or branched-chain carbon linkers, heterocyclic carbon linkers, or peptide linkers.

Additionally, in several aspects, the linker can include a spacer element, which, when present, increases the size of the linker such that the distance between the detectable marker and the antibody is increased.

An antibody can also be derivatized with a chemical group such as polyethylene glycol (PEG), a methyl or ethyl group, or a carbohydrate group. These groups may be useful to improve the biological characteristics of the antibody, such as to increase serum half-life or to increase tissue binding.

When using a metal radioactive isotope, for example $^{111}In$, as a detectable molecule it can be attached by conjugating a monoclonal antibody to a chelating agent, such as DTPA, and subsequently incubating the monoclonal antibody-conjugated to DTPA with a source of radioactive isotope, such that each chelating agent conjugated to the monoclonal antibody chelates the radioactive isotope.

Chelating agents capable of being conjugated to a monoclonal antibody are commercially available, for instance, p-SCN-Bn-CHX-A"-DTPA (sold by Macrocyclics™ Cat #B-355), DTPA-SCN (sold by Macrocyclics™ Cat #B-305) p-SCN-Bn-DOTA (sold by Macrocyclics™ Cat #B-205), p-SCN-Bn-Deferoxamine (sold by Macrocyclics™ Cat #B-705), or p-SCN-Bn-NOTA (sold by Macrocyclics™ Cat #B-605).

Bifunctional chelating agents may be used to form an antibody-conjugated to a metal chelate. A bifunctional chelating agent is a molecule capable of forming a bond with another molecule and also capable of forming a metal chelate by binding a metal ion. Appropriate bifunctional chelating agents therefore include a reactive group and a metal chelating group. The reactive group of a bifunctional chelating agent is a group of atoms that that will undergo a reaction with a surface group of an antibody to form a bond. Examples of reactive groups include carboxylic acid groups, diazotiazable amine groups, N-hydroxysuccinimidyl, esters, aldehydes, ketones, anhydrides, mixed anhydrides, acyl halides, maleimides, hydrazines, benzimidates, nitrenes, isothiocyanates, azides, sulfonamides, bromoacetamides, iodocetamides, carbodiimides, sulfonylchlorides, hydroxides, thioglycols, or any reactive group useful for forming conjugates.

Specific examples of bifunctional chelating agents include bifunctional diethylenetriaminepentaacetic acid (DTPA) derivatives such as those disclosed in U.S. Pat. No. 5,434,287 to Gansow et al. Other examples include poly-substituted diethylenetriaminepentaacetic acid chelates such as those described by Gansow et al. in U.S. Pat. No. 5,246,692. Bifunctional chelating agents comprising 1,4,7,10-Tetraazacyclododecane-N,N',N",N'"-tetraacetic acid (DOTA) and its derivatives are also useful. Examples of bifunctional DOTA derivatives are provided in U.S. Pat. No. 5,428,154 to Gansow et al. and references therein. A particular example of a bifunctional imaging agent is 2-(p-isothiocyanatobenzyl)-6-methyl-diethylenetriaminepentaacetic acid (1B4M).

In some examples, the chelator is an acyclic chelator, which includes linear or branched chains of atoms. Exemplary acrylic chelators include DTPA and DFO. In some examples the chelator is a macrocyclic chelator, which includes a ring-shaped structure with multiple donor groups that can form a cage around metal ions. Exemplary macrocyclic chelators include DOTA and NOTA. In some examples, the chelator has a molecular weight of equal to or less than 1000 g/mol, 800 g/mol, 700 g/mol, 600 g/mol, 500 g/mol, 400 g/mol, or 300 g/mol.

The average number of near-infrared fluorescent dye moieties and metal chelator moieties per antibody in the conjugate can range, for example, from 1 to 10 moieties per antibody. In some aspects, the antibody-conjugate comprises about 1-5 fluorescent dye molecules per monoclonal antibody and about 1-3 DTPA molecules per monoclonal antibody. In some aspects, the antibody-conjugate comprises about 1-3 fluorescent dye molecules per monoclonal antibody and about 1-2 DTPA molecules per monoclonal antibody. In some aspects, the antibody-conjugate comprises a molar ratio of the monoclonal antibody to the DTPA of about 1 to 1.5 to about 1 to 2 and a molar ratio of the monoclonal antibody to the fluorescent dye of about 1 to 1 to about 1 to 3. The average number of detectable marker moieties per antibody in preparations of conjugates may be characterized using any suitable means, such as those described in the examples.

In some examples the average number of near-infrared fluorescent dye moieties per monoclonal antibody or antigen binding fragment and/or the average number of metal chelator moieties per monoclonal antibody or antigen binding fragment in the conjugate can range from about 0.5 to about 1.0, about 0.5 to about 1.5, about 0.5 to about 2.0, about 0.5 to about 2.5, about 0.5 to about 3.0, about 0.5 to about 3.5, about 0.5 to about 4.0, about 0.5 to about 5.0, about 0.5 to about 10.0, about 1.0 to about 1.5, about 1.0 to about 2.0, about 1.0 to about 2.5, about 1.0 to about 3.0, about 1.0 to about 3.5, about 1.0 to about 4.0, about 1.0 to about 5.0, about 1.0 to about 10.0, about 1.5 to about 2.0, about 1.5 to about 2.5, about 1.5 to about 3.0, about 1.5 to about 3.5, about 1.5 to about 4.0, about 1.5 to about 5.0, about 1.5 to about 10, about 2.0 to about 2.5, about 2.0 to about 3.0, about 2.0 to about 3.5, about 2.0 to about 4.0, about 2.0 to about 5.0, about 2.0 to about 10.0, about 2.5 to about 3.0, about 2.5 to about 3.5, about 2.5 to about 4.0, about 2.5 to about 5.0, about 2.5 to about 10.0, about 3.0 to about 3.5, about 3.0 to about 4.0, about 3.0 to about 5.0, about 3.0 to about 10.0, about 3.5 to about 4.0, about 3.5 to about 5.0, about 3.5 to about 10.0, about 4.0 to about 5.0, about 4.0 to about 10.0, or about 5.0 to about 10.0 moieties per antibody. In further specific examples, the average number of near-infrared fluorescent dye moieties per monoclonal antibody or antigen binding fragment and/or the average number of metal chelator moieties per monoclonal antibody or antigen binding fragment in the conjugate can be about 0.5, about 1.0, about 1.5, about 2.0, about 2.5, about 3.0, about 3.5 about 4.0, about 5.0, or about 10.0. In some examples, the average number of near-infrared fluorescent dye moieties per antibody and/or the average number of metal chelator moieties per antibody can be expressed as a molar ratio of near-infrared fluorescent dye molecules and/or metal chelator molecules to antibodies.

The loading (for example, detectable molecule/antibody ratio) of an conjugate may be controlled in different ways, for example, by: (i) limiting the molar excess of detectable molecule-linker intermediate or linker reagent relative to antibody, (ii) limiting the conjugation reaction time or temperature, (iii) partial or limiting reductive conditions for cysteine thiol modification, (iv) engineering by recombinant techniques the amino acid sequence of the antibody such that the number and position of cysteine residues is modified for control of the number or position of linker-detectable molecule attachments (such as thioMab or thioFab prepared as disclosed in WO2006/03448, incorporated by reference herein in its entirety). When multiple distinct moieties are conjugated to a single antibody it may be helpful to observe the impact of each conjugate on the others, for example the impact of DTPA on 800CW dye fluoresce, and to optimize the ratios of each conjugate so as not to interfere with the others.

In some examples the near-infrared fluorescent dye, such as an 800CW dye, is conjugated to a monoclonal antibody or antigen binding fragment by providing a molar excess of the near-infrared fluorescent dye relative to the monoclonal antibody or antigen binding fragment, such as about 2.0 to about 6.0, about 2.5 to about 6.0, about 3.0 to about 6.0, about 3.5 to about 6.0, about 4.0 to about 6.0, about 4.5 to about 6.0, about 5.0 to about 6.0, about 5.5 to about 6.0, about 2.0 to about 5.5, about 2.5 to about 5.5, about 3.0 to about 5.5, about 3.5 to about 5.5, about 4.0 to about 5.5, about 4.5 to about 5.5, about 5.0 to about 5.5, about 2.0 to about 5.0, about 2.5 to about 5.0, about 3.0 to about 5.0, about 3.5 to about 5.0, about 4.0 to about 5.0, about 4.5 to about 5.0, about 2.0 to about 4.5, about 2.5 to about 4.5, about 3.0 to about 4.5, about 3.5 to about 4.5, about 4.0 to about 4.5, about 2.0 to about 4.0, about 2.5 to about 4.0, about 3.0 to about 4.0, about 3.5 to about 4.0, about 2.0 to about 3.5, about 2.5 to about 3.5, about 3.0 to about 3.5, about 2.0 to about 3.0, about 2.5 to about 3.0, or about 2.0 to about 2.5 molar excess of the near-infrared fluorescent dye. In further specific examples the near-infrared fluorescent dye is conjugated to a monoclonal antibody or antigen binding fragment by providing about 2.0, about 2.5, about 3.0, about 3.5, about 4.0, about 4.5, about 5.0, about 5.5, or about 6.0 molar excess of the near-infrared fluorescent dye, or an amount greater than any of these values.

In some examples the chelator, such as DTPA, is conjugated to the monoclonal antibody or antigen binding fragment by providing a molar excess of the chelator relative to the monoclonal antibody or antigen binding fragment, such as about 10 to about 55, about 15 to about 55, about 20 to about 55, about 25 to about 55, about 30 to about 55, about 35 to about 55, about 40 to about 55, about 45 to about 55, about 50 to about 55, about 10 to about 50, about 15 to about 50, about 20 to about 50, about 25 to about 50, about 30 to about 50, about 35 to about 50, about 40 to about 50, about 45 to about 50, about 10 to about 45, about 15 to about 45, about 20 to about 45, about 25 to about 45, about 30 to about 45, about 35 to about 45, about 40 to about 45, about 10 to about 40, about 15 to about 40, about 20 to about 40, about 25 to about 40, about 30 to about 40, about 35 to about 40, about 10 to about 35, about 15 to about 35, about 20 to about 35, about 25 to about 35, about 30 to about 35, about 10 to about 30, about 15 to about 30, about 20 to about 30, about 25 to about 30, about 10 to about 25, about 15 to about 25, about 20 to about 25, about 10 to about 20, about 15 to about 20, or about 10 to about 15 molar excess of the chelator. In further specific examples, the chelator is conjugated to a monoclonal antibody or antigen binding fragment by providing about 10, about 15, about 20, about 25, about 30, about 35, about 40, about 45, about 50, about 55, or about 60 molar excess of the chelator, or an amount greater than any of these values.

In one example the antibody-conjugate is $^{111}$In-dinutuximab-IRDye800CW wherein the $^{111}$In is chelated by DTPA conjugated to the dinutuximab or DOTA conjugated to the dinutuximab. In another example the antibody-conjugate is $^{64}$Cu-dinutuximab-IRDye800CW wherein the $^{64}$Cu is chelated by DOTA conjugated to the dinutuximab or NOTA conjugated to the dinutuximab. In another example the antibody-conjugate is $^{89}$Zr-dinutuximab-IRDye800CW wherein the $^{89}$Zr is chelated by DFO conjugated to the dinutuximab. In another example the antibody-conjugate is $^{99m}$Tc-dinutuximab-IRDye800CW. In another example the antibody-conjugate is $^{99m}$Tc-αGD2 antibody fragment-IRDye800CW.

Disclosed herein is a method of producing an antibody conjugate. In some examples, this includes incubating a monoclonal antibody or antigen binding fragment conjugated to a chelator (such as DTPA) and a fluorescent dye (such as an 800CW dye) with a radioisotope. In some examples, probe has a ratio of radioisotope to monoclonal antibody or antigen binding fragment conjugated to chelator and fluorescent dye of about 1.5 microcurie: 1 μg to about 2.5 microcurie: 1 μg. In some examples, the method includes incubating a ratio of about 1 millicurie radioisotope: 300 μg monoclonal antibody or antigen binding fragment conjugated to the chelator and the infrared dye to about 1 millicurie radioisotope: 600 μg monoclonal antibody or antigen binding fragment conjugated to the chelator and the infrared dye. In some examples, the incubating takes place at about 6 pH. In some examples the incubating takes place at about 6.03 pH. In some examples, 600 μg of probe are incubated in 400 μL of sodium citrate buffer with 1-2 millicurie of radioisotope (such as In-111). In some examples, excess radioisotope is purified. In some examples, probe conjugated to radioisotope is purified.

In some examples the antibody conjugate has an average amount of radioisotopes per grams of monoclonal antibody(s) or antigen binding fragment(s) conjugated to a chelator and a fluorescent dye such as about 1 μCi (microcurie)/μg, about 1.5 μCi/μg, about 2.0 μCi/μg, about 2.5 μCi/μg, about 3 μCi/μg, or a range between any two of these values. In some examples, the method of making the antibody conjugate includes incubating an amount of radioisotope per grams of monoclonal antibody(s) or antigen binding fragment(s) conjugated to a chelator and a fluorescent dye such as about 1 mCi/200 μg, 1 mCi/300 μg, 1 mCi/400 μg, 1 mCi/500 μg, 1 mCi/600 μg, 1 mCi/700 μg, or a range between any two of these values.

Detecting GD2-Positive Cells and Cancer

Methods are provided for detecting the presence or absence of cell-surface GD2 expression in a subject. In some aspects, the methods include contacting a cell from a subject with a radiolabeled antibody-conjugate as described herein to form an immune complex with cell-surface GD2. The presence (or absence) of the immune complex is then assessed by detecting the radiolabel (e.g., using photographic film or scintillation counters) and the fluorescent marker (e.g., using a photodetector to detect emitted illumination). The detection methods can involve in vivo detection or in vitro detection of the immune complex. In several aspects, detecting cell-surface GD2 expression in a subject detects the presence of a GD2-positive cancer in the subject. In several aspects, the method is used to delineate GD2-positive tumor borders, for visual mapping of a primary GD2-positive tumor bed, or the detection of occult GD2-positive tumor lesions.

In some aspects, a subject is selected for evaluation who has, is suspected of having, or is at risk of developing, a GD2-positive cancer, for example, a carcinoma. For example, the subject has, is suspected of having, or is at risk of developing a GD2-positive neuroblastoma, melanoma, osteosarcoma, retinoblastoma, Ewing sarcoma, small cell lung cancer, glioma, soft tissue sarcoma, or breast cancer. Thus, the presence of a GD2-positive cancer can be detected in these subjects.

In one aspect, a sample is obtained from a subject, and the presence of a cell that expresses GD2 is assessed in vitro. For example, such methods include contacting an endothelial cell in a biological sample from the subject with one or more of the antibody-conjugates provided herein that specifically bind GD2 to form an immune complex. The presence (or absence) of the immune complex is then detected. The presence of the immune complex on the cell from the subject indicates the presence of a cell that expresses GD2 in the subject. For example, an increase in the presence of the immune complex in the sample as compared to formation of the immune complex in a control sample indicates the presence of a cell that expresses GD2 in the subject.

A biological sample is typically obtained from a mammalian subject of interest, such as human. The sample can be any sample, including, but not limited to, tissue from biopsies, autopsies and pathology specimens. Biological samples also include sections of tissues, for example, frozen sections taken for histological purposes.

In some examples, in vivo detection of a cell that expresses GD2 detects a tumor in the subject, for example, neuroblastoma, melanoma, osteosarcoma, retinoblastoma, Ewing sarcoma, small cell lung cancer, glioma, soft tissue sarcoma, or breast cancer. In one aspect, an effective amount of an antibody-conjugate that specifically binds to GD2 is administered to the subject for a sufficient amount of time for the antibody to form an immune complex, which can then be detected. Detection of the immune complex in the subject determines the presence of a cell that expresses GD2, which detects cancer in the subject. In one specific, non-limiting example detection of an immune complex is performed by immunoscintography. Other specific, non-limiting examples of immune complex detection include radiolocalization, radioimaging, magnetic resonance imaging (such as using a biotinylated antibody and avidin-iron oxide), positron emission tomography (such as using an $^{111}$indium-labeled monoclonal antibody) or fluorescence imaging (such as using luciferase, green fluorescent protein, or 800CW dye labeled antibodies). See Paty et al., *Transplantation.*, 77:1133-1137, 2004, herein incorporated by reference. In one aspect the immune complex is detected via handheld gamma probe and/or handheld near infrared fluorescent camera. In another aspect the immune complex is detected via handheld gamma probe and/or handheld near infrared fluorescent camera during surgery, and the presence of immune complex aids in delineation of tumor borders, visual mapping of the primary tumor bed, or the detection of occult tumor lesions.

In one aspect, an effective amount of an antibody-conjugate is administered to a subject having a tumor following anti-cancer or anti-angiogenic treatment. After a sufficient amount of time has elapsed to allow for the administered antibody-conjugate to form an immune complex with GD2 on the surface of cancer cells, the immune complex is detected. For example, the antibody-conjugate can be administered to a subject prior to, or following, treatment of a tumor. The tumor can be (but is not limited to) a neuroblastoma, melanoma, osteosarcoma, retinoblastoma, Ewing sarcoma, small cell lung cancer, glioma soft tissue sarcoma, or breast cancer. The presence (or absence) of the immune complex can be used to evaluate the effectiveness of the treatment. For example, a decrease in the immune complex compared to a control taken prior to the treatment indicates a reduction in tumor burden.

Administration of the antibody-conjugate can be accompanied by administration of other anti-cancer or anti-angiogenesis therapeutic treatments such as surgical resection of a tumor or radiation therapy. For example, prior to, during, or following administration of the antibody-conjugate the subject can receive one or more additional therapies. In one example, at least part of the tumor is surgically or otherwise excised or reduced in size or volume prior to administering the antibody-conjugate. In another example the antibody-conjugate is administered prior to surgical resection of the tumor or a part thereof. In another example, the antibody-conjugate is administered during the course of a surgical resection of the tumor or a part thereof. In some aspects, the presence of antibody-conjugate in immune complex with GD2 expressing tumor cells aids in delineation of tumor borders, visual mapping of the primary tumor bed, or the detection of occult tumor lesions during a surgical resection of the tumor, to assist the surgeon in removing the tumor from the subject.

Compositions

Compositions are provided that include the antibody-conjugate disclosed herein in a pharmaceutically acceptable carrier. The compositions are useful, for example, for example, for the detection of a GD2-positive cancer in a subject. The compositions can be prepared in unit dosage forms for administration to a subject. The amount and timing of administration are at the discretion of the administering physician to achieve the desired purposes. The GD2-specific antibody-conjugate can be formulated for systemic or local administration. In one example, the GD2-specific antibody-conjugate is formulated for parenteral administration, such as intravenous administration.

In some aspects, the antibody-conjugate in the composition is at least 70% (such as at least 75%, at least 80%, at least 85%, at least 90%, at least 95%, at least 96%, at least 97%, at least 98% or at least 99%) pure. In some aspects, the composition contains less than 10% (such as less than 5%, less than 4%, less than 3%, less than 2%, less than 1%, less than 0.5%, or even less) of macromolecular contaminants, such as other mammalian (e.g., human) proteins.

The compositions for administration can include a solution of the antibody-conjugate dissolved in a pharmaceutically acceptable carrier, such as an aqueous carrier. A variety of aqueous carriers can be used, for example, buffered saline and the like. These solutions are sterile and generally free of undesirable matter. These compositions may be sterilized by any suitable technique. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antibody-conjugate in these formulations can vary widely, and will be selected primarily based on fluid volumes, viscosities, body weight and the like in accordance with the particular mode of administration selected and the subject's needs.

A typical composition for intravenous administration comprises about 0.01 to about 30 mg/kg of the antibody-conjugate per subject per day. Any suitable method may be used for preparing administrable compositions; non-limiting examples are provided in such publications as *Remington: The Science and Practice of Pharmacy,* 22$^{nd}$ *ed.*, London, UK: Pharmaceutical Press, 2013. In some aspects, the composition can be a liquid formulation including the antibody-conjugate in a concentration range from about 0.1 mg/ml to about 20 mg/ml, or from about 0.5 mg/ml to about 20 mg/ml, or from about 1 mg/ml to about 20 mg/ml, or from about 0.1 mg/ml to about 10 mg/ml, or from about 0.5 mg/ml to about 10 mg/ml, or from about 1 mg/ml to about 10 mg/ml.

The antibody-conjugate can be provided in lyophilized form and rehydrated with sterile water before administration, although it can also be provided in a sterile solution of known concentration. The antibody-conjugate solution can then be added to an infusion bag containing 0.9% sodium chloride, USP, and typically administered at a dosage of from 0.5 to 15 mg/kg of body weight. Antibody-conjugates can be administered by slow infusion, rather than in an intravenous push or bolus.

Controlled-release parenteral formulations can be made as implants, oily injections, or as particulate systems. For a broad overview of protein delivery systems see, Banga, *Therapeutic Peptides and Proteins: Formulation, Processing, and Delivery Systems,* 3$^{rd}$ Ed. Boca Raton, FL: CRC Press Inc, Inc., 2015. Particulate systems include microspheres, microparticles, microcapsules, nanocapsules, nanospheres, and nanoparticles. Microcapsules contain the active protein agent, such as a cytotoxin or a drug, as a central core. In microspheres, the active protein agent is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly. See, for example, *Treatise on Controlled Drug Delivery: Fundamentals, Optimization, Applications*, A. Kydonieus (Ed.), Boca Raton, FL: CRC Press Inc, Inc., 2021.

Polymers can be used for ion-controlled release of the antibody-conjugate compositions disclosed herein. Any suitable polymer may be used, such as a degradable or nondegradable polymeric matrix designed for use in controlled drug delivery. Alternatively, hydroxyapatite has been used as a microcarrier for controlled release of proteins. In yet another aspect, liposomes are used for controlled release as well as drug targeting of the lipid-capsulated drug.

Kits

Kits are also provided. For example, kits for detecting a cell (such as a tumor cell) that expresses GD2 in a subject. The kits include an antibody-conjugate that specifically binds to GD2 as described herein. In some examples the kit includes a first container containing an antibody-conjugate that lacks a radioisotope metal as described herein and a separate container containing a radioisotope which can be chelated with the antibody-conjugate prior to use.

The kit can include a container and a label or package insert on or associated with the container. Suitable containers include, for example, bottles, vials, syringes, etc. The containers may be formed from a variety of materials such as glass or plastic. The container typically holds a composition including one or more of the disclosed GD2 specific antibody-conjugates. In several aspects the container may have a sterile access port (for example the container may be an intravenous solution bag or a vial having a stopper pierceable by a hypodermic injection needle). A label or package insert indicates that the composition is used for treating the particular condition.

The label or package insert typically will further include instructions for use of a disclosed GD2 specific antibody-conjugate, for example, in a method of identifying, treating or preventing cancer in a subject. The package insert typically includes instructions customarily included in commercial packages of therapeutic products that contain information about the indications, usage, dosage, administration, contraindications and/or warnings concerning the use of such therapeutic products. The instructional materials may be written, in an electronic form or may be visual (such as video files). The kits may also include additional components to facilitate the particular application for which the kit is designed. The kits may additionally include buffers and other reagents routinely used for the practice of a particular method.

EXAMPLES

The following examples are provided to illustrate particular features of certain aspects of the disclosure, but the scope of the claims should not be limited to those features exemplified.

Example 1

Antibody-Conjugate Optimization and Synthesis

This example illustrates the design and assessment of an antibody-conjugate that can identify the presence of GD2 expressing cells.

Synthesis of $^{111}$In-dinutuximab-IRDye800CW. To remove preservatives and stabilizers that would impede conjugation reactions, 1 mL dinutuximab (United Therapeutics Oncology) or αGD2 (14G2a) (BioXCell) was added to a 2-6 mL Pierce Protein Concentrator, 10K molecular weight cut-off (ThermoScientific), and diluted to the 6 mL mark with 1×PBS. The concentrator was centrifuged at 4,000×g until ~1 mL remained, diluted to 6 mL and centrifuged again, then repeated for a total of 5 rinses. Purity was confirmed by Size-Exclusion HPLC (SE-HPLC), and the final concentration determined by UV-Vis Spectrophotometry.

To conjugate the DTPA chelator to the antibody, 1.0 mg of purified antibody was added to 25 mM sodium carbonate/bicarbonate buffer, pH 9, with a 15-molar excess of p-SCN-Bn-CHX-A"-DTPA (Macrocyclics B-355) with a total reaction volume of 1.00 mL. The reaction mixture was incubated with shaking at 37° C. for 30 min, then analyzed by SE-HPLC. Further excess of DTPA could have been added if substitution did not reach desired level. The same purification technique as above was employed for the reaction mixture. DTPA substitution level was determined by UV-Vis spectrophotometry.

Dinutuximab-DTPA was added to same reaction buffer as above with 3-molar excess IR800CW-NHS ester (LiCor) with total reaction volume 1.00 mL. Mixture was incubated for 20 minutes at room temperature with shaking, then analyzed by SE-HPLC. Further excess of dye could have been added if desired substitution level was not reached. Final dinutuximab-DTPA-IR800CW conjugate was purified using the same method as above. Purity and substitution level were determined by SE-HPLC and UV-Vis spectrophotometry, respectively.

Exemplary radiolabeling methods can be found in Nalla et al., *Curr. Radiopharm.* (2011) 4:1-4. To perform radiolabeling sodium citrate (500 mM) was added to the In-111 stock solution to bring the volume to 1.6 mL at pH 6. After 5 min, the anti-GD2-DPTA was added to the In-111 solution and incubated at 25° C. for 30 min. Instant thin-layer chromatography (ITLC) was used to determine the radiolabeling efficiency, which was developed using 50 mM sodium citrate eluent. High-performance liquid chromatography (HPLC) using a BioSec3 column and gamma detector was performed to confirm the successful radiolabeling of the anti-GD2-DPTA conjugate, and the tracer was subsequently buffer-exchanged with DPBS (Lonza, Cat #175512F12) for use.

Synthesis of $^{111}$In-αGD2(14G2a)-IRDye800CW. 5 mg of anti-GD2 (Clone: 14G2a, BioXCell) in PBS solution was adjusted to pH 9.0 with 1M Sodium carbonate solution. A 50-molar excess of DTPA-SCN (Macrocyclics) was then added, and the reaction mixture was incubated at room temperature (with shaking) for 50 min. The reaction was monitored by size exclusion high pressure liquid chromatography (SEC-HPLC) or fast protein liquid chromatography (FPLC). After 50 min of reaction, 5 molar excess of IR800CW-NHS ester (Li-Cor) was added and incubated for 10 min, after which 20 ul of 0.2M glycine was added to stop the reaction. The Anti-GD2-DTPA-IR800 conjugate was purified by AKTA pure FPLC, using a Superdex 200 Increase 10/300 GL column, with 100 mM sodium citrate as a buffer. The resultant fractions were pulled together and concentrated using a Pierce Protein Concentrator, 30K molecular weight cut-off (ThermoScientific). The same process was used to create DTPA- and IR800CW-labeled isotype GD2α (BioXCell).

Exemplary radiolabeling methods can be found in Nalla et al., *Curr. Radiopharm.* (2011) 4:1-4. To perform radiolabelings citrate (500 mM) was added to the In-111 stock solution to bring the volume to 1.6 mL at pH 6. After 5 min, the anti-GD2-DPTA was added to the In-111 solution and incubated at 25° C. for 30 min. Instant thin-layer chromatography (ITLC) was used to determine the radiolabeling efficiency, which was developed using 50 mM sodium citrate eluent. High-performance liquid chromatography (HPLC) using a BioSec3 column and gamma detector was performed to confirm the successful radiolabeling of the anti-GD2-DPTA conjugate, and the tracer was subsequently buffer-exchanged with DPBS (Lonza, Cat #175512F12) for tail vein injections.

Figure 1C:
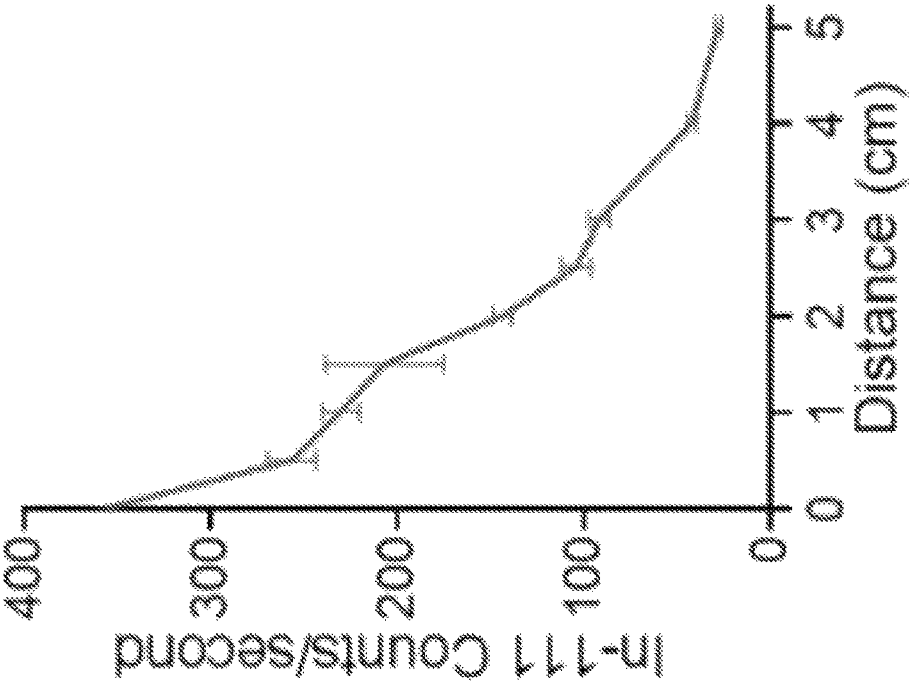
Figure 1B:
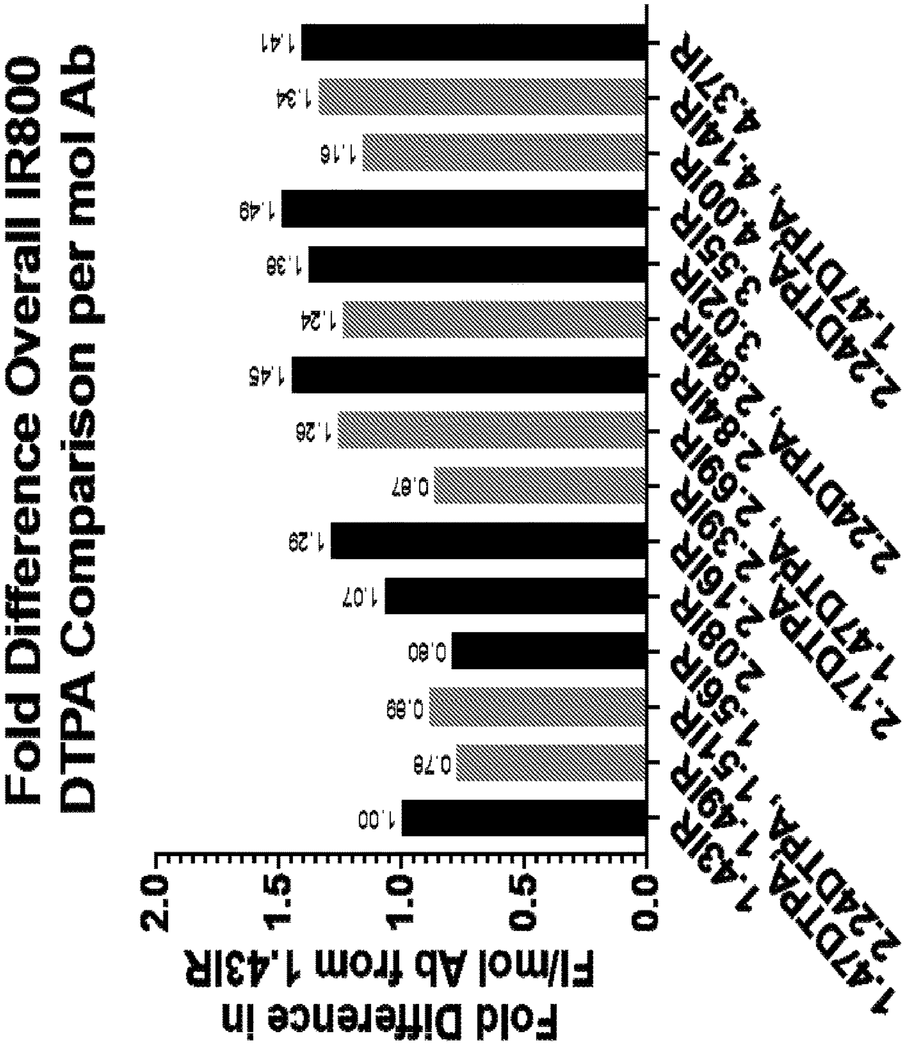

Optimization of $^{111}$In-dinutuximab-IRDye800CW and $^{111}$In-αGD2(14G2a)-IRDye800CW. An approximately linear increase in fluorescence was seen between conjugation of 1-3 IR800 fluorophores per antibody (FIG. 1A). The fluorescence signal peaked above 3 IR800 fluorophores per antibody, and at higher concentrations it would likely even decrease due to quenching. The synthesis was optimized to obtain 1-3 fluorophores per antibody. Conjugation of DTPA was found to decrease fluorescence intensity of the probe and decrease the binding affinity of the antibody (FIG. 1B). However, with only 1-1.5 DTPA moieties per antibody (the In-111 chelator), adequate gamma signal was observed from tumors labeled with the probe with up to 5 cm of processed tissue between the probe and sensor (FIG. 1C). The synthesis was optimized for 1.5-2 DTPA moieties per antibody.

The effect of conjugation of IR800 and DTPA on the binding affinity was assessed. While both decrease the binding affinity (Kd 1.869 nM for dinutuximab alone vs 9.539 nM for dinutuximab-DTPA vs 22.28 nM for dinutuximab-DTPA-IR800), the binding affinity of the labeled probe remains sufficiently high for use as a specific imaging agent (Table 1).

FBS (Hyclone, Cat #SH3091003), 100 mM sodium pyruvate (Lonza, Cat #BW13-115E), 1× Antibiotic-Antimycotic (Gibco, Cat #15-240-062), 55 μM beta-mercaptoethanol (Gibco, Cat #21-985-023), 1×MEM NEAA (Gibco, Cat #11140-050), and 50 mg/mL Normicin (Invivogen, Cat #ant-nr-2) and maintained in a 37° C. humidified incubator with 5% $CO_2$.

Flow cytometry for GD2 expression. Cells were detached from Corning™ T-75 vented cell culture flasks (Cat #430641U) with Corning™ 0.05% Trypsin/0.53 mM EDTA in HBSS without calcium, magnesium, or sodium bicarbonate (Cat #MT25052CI). Each line was stained with PE anti-human Ganglioside GD2 (1 μg per one million cells, Cat #357304) at 4° C. for 30 min. Quantibrite™ PE beads (Cat #340495) were stained with GD2 and were used to quantify the number of GD2 molecules per cell. Analyses were performed on the LSR Fortessa (BD Biosciences), and the data were analyzed using FlowJo Software, version 10.8 (BD Biosciences).

Figures 2A, 2B:
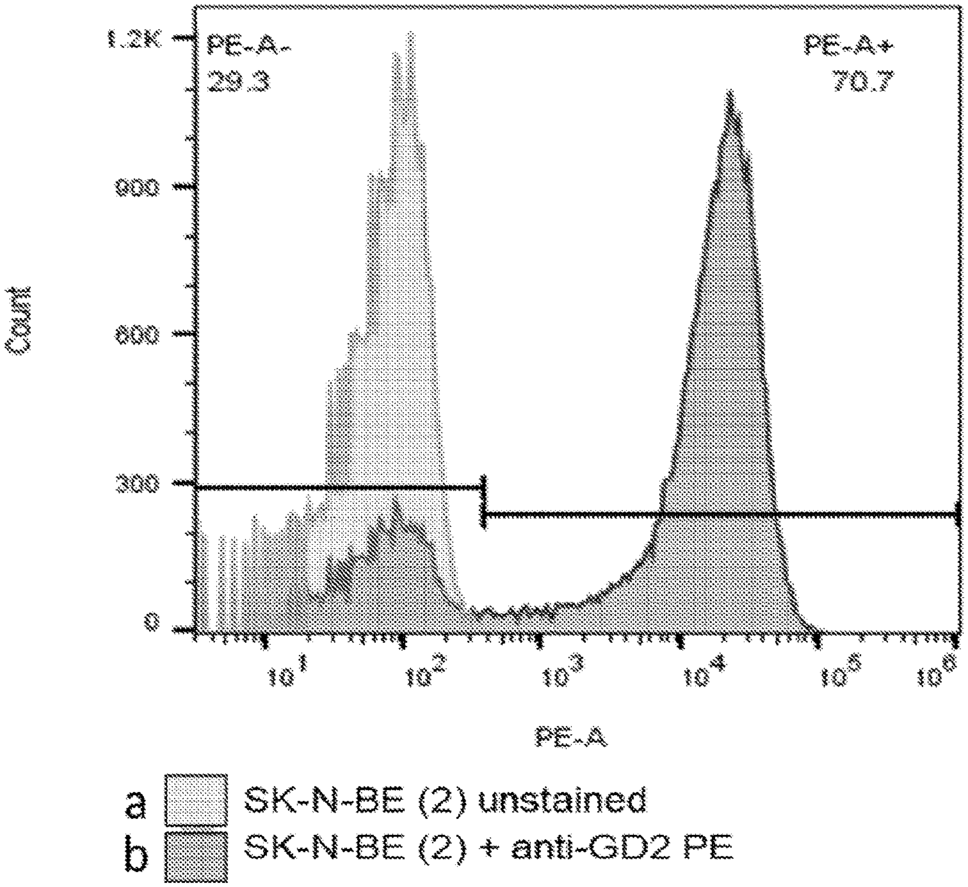
FIGS. 2A-2C. GD2 expression on human NB cell lines.

Quantitation for GD2 expression. The mean values for control PE staining were used with Quantibrite PE beads to create a standard curve of PE molecules per bead. The mean values for positive PE staining were determined by overlaying the positive and negative stains and subtracting any overlapping areas within the curves. The positive mean values were then substituted into the standard curve equation to determine the average GD2 molecules per cell. There was variable GD2 expression among the cell lines; NMB6 showed the highest expression, SK-N-BE (2) and SK-N-AS showed high expression, SH-SY5Y showed intermediate expression and CHP212 and SK-N-SH showed low/no expression and a thousand-fold difference in GD2 expression between NMB6 and SK-N-AS. (FIG. 2) Given the high GD2 expression on SK-N-BE (2), its ability to establish orthotopic tumors, and its wide usage across published preclinical NB research this cell line was selected for preliminary studies.

TABLE 1

| One Site - Specific Binding | aGd2 Standard | Dinutuximab-DTPA-IR800 | Dinutuximab | Dinutuximab-DTPA |
|---|---|---|---|---|
| Best-Fit Values | | | | |
| Bmax | 0.4963 | 0.4692 | 0.4368 | 0.5548 |
| Kd (nM) | 2.395 | 22.28 | 1.869 | 9.539 |
| 95% CI (profile Likelihood | | | | |
| Bmax | 0.4441 to 0.5518 | 0.4063 to 0.5433 | 0.3883 to 0.4883 | 0.5051 to 0.6082 |
| Kd | 0.9987 to 4.618 | 12.92 to 37.73 | 0.6098 to 3.890 | 6.323 to 14.13 |

Synthesis variables including the quantity of DTPA-SCN and IR800CW-NHS used in the reaction, and method of purification were modified to obtain 1-3 fluorophores per antibody, 1-1.5 DTPA per antibody, and to optimize yield.

Example 2

Neuroblastoma Cell Line GD2 Expression

This example illustrates expression of GD2 on the cell surface of neuroblastoma cell lines.

In vitro maintenance of cell lines. NMB6, SK-N-BE(2) (ATCC no. CRL-2271), SK-N-AS (ATCC no. CRL-2137), SK-N-SH (ATCC no. HTB-11), SH-SY5Y (ATCC no. CRL-2266) and CHP212 (CHP tumor bank) cells were cultured in Dulbecco's Modified Eagle Medium (Lonza, Cat #BW12614F), supplemented with 10% heat-inactivated

Example 3

Intraoperative Detection

This example illustrates intraoperative detection of antibody-conjugate to improve surgical outcomes.

Orthotopic Xenograft Model. Four- to six-week-old athymic nude (nu/nu) (NCRNU-F sp/sp) mice or athymic nude (Crl:NIH-Foxn1$^{rnu}$) rats, were used for orthotopic xenograft mouse and rat models, respectively. Under isoflurane anesthesia (2-3% in 1 L/min oxygen), a transverse left flank incision was made with fine sharp-tip surgical scissors in the dorsal skin. A 1-cm incision was made in the lateral body wall and the left kidney and accompanying adrenal gland were exteriorized and maneuvered using a cotton tip applicator. One million human SK-N-SH neuroblastoma cells (ATCC; HTB-11) or SK-N-BE (2) (ATCC; CRL-2268) suspended in 20 μL of Matrigel basement membrane matrix (354234, Corning, NY) were implanted into the left adrenal gland and surrounding fat pad with a 30-gauge needle on a 1 cc syringe. After the cells were injected and the Matrigel protein polymerized the needle was removed. The kidney and adrenal gland were returned to the abdominal cavity and a 4-0 Polysorb suture was used to close the body wall. The skin was closed with surgical wound clips and the animals recovered in a clean cage placed on a heating pad and monitored until sternally recumbent. Wound clips were removed 10-14 days after the procedure. MRI was used to monitor tumor growth and was performed at 3, 4 and 5 weeks after orthotopic injection. Animals that reached USDA Class D sacrifice requirements were euthanized upon reaching these standards.

Gamma- and Fluorescent Intraoperative Detection Protocol. The intraoperative molecular imaging (IMI) tracer was evaluated in the context of two clinically utilized intraoperative detection systems: a Neoprobe (Mammotome) gamma probe and a SPY-PHI (Stryker) NIR camera. A gamma probe is a wand-shaped instrument that detects gamma decay in a linear range with high sensitivity. Additionally a handheld NIR camera that detects fluorescence signal and displays it on a monitor was used. Three mice were administered adrenal gland injections with $1\times10^6$ SK-N-BE(2) cells and $^{111}$In-αGD2-IRDye800CW via tail vein injection four weeks after the cells were injected. The Neoprobe was held over the major regions of the body to determine the 111 In counts in each region at three- and four-days post tracer injection to evaluate regional specificity (FIG. 4). The SPY-PHI was also used at three- and four-days post tracer injection to visualize the tumor and tumor bed regions of the mice. The SPY-PHI was used to visualize tumor pre- and post-resection. The Neoprobe was used to quantify gamma signal of the tumor prior to opening the skin, during resection and post-resection.

Figure 5A:
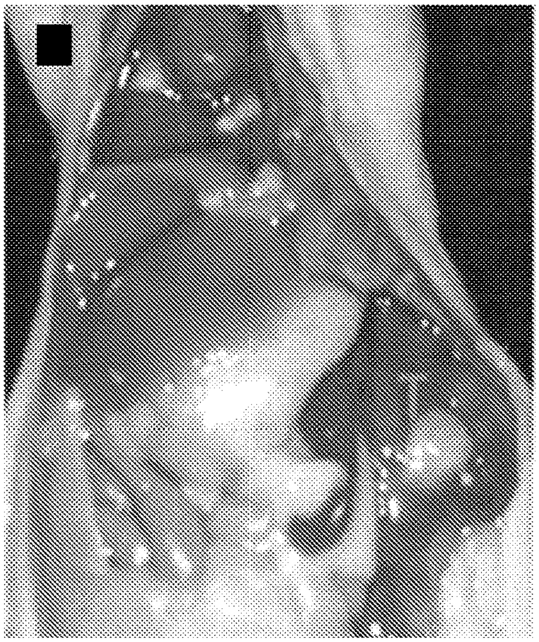
FIGS. 5A-5D. Detection of fluorescence in tumor-bearing mice with handheld near infrared fluorescent camera.
Figure 5B:
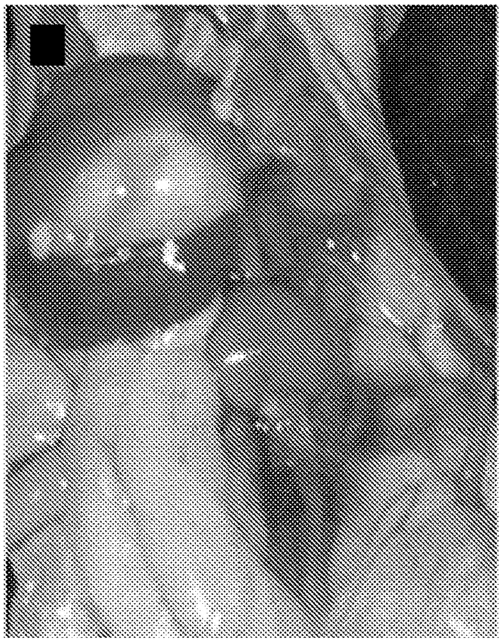
Figure 5C:
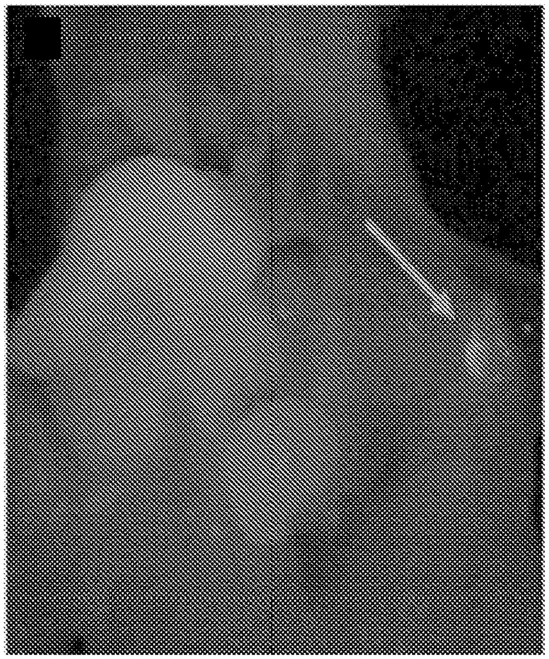
Figure 5D:
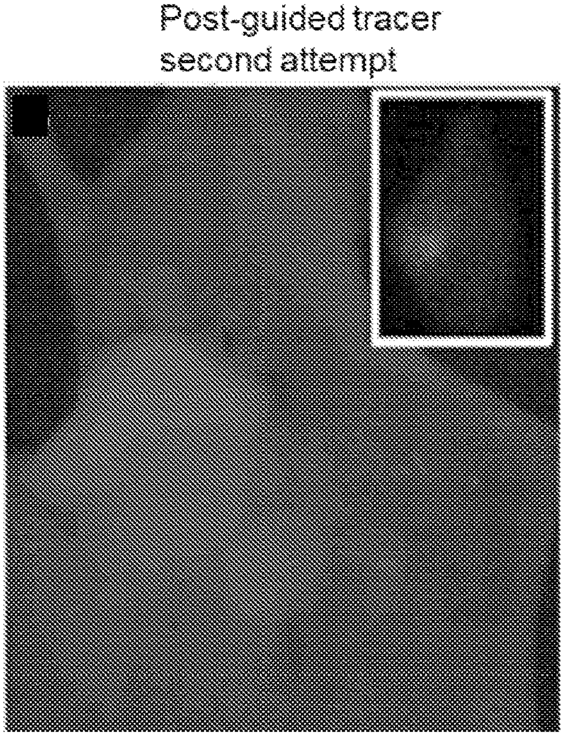

The SPY-PHI camera was able detect residual disease in and around the tumor bed after tumor resection. Mice (n=2, new mice) were administered tracer 3 weeks after SK-N-BE (2) injection and 4 days prior to surgery. Complete tumor resection was performed without IMI (FIGS. 5A and 5B; however, post-resection NIR imaging revealed unexpected residual disease (FIG. 5C). The gamma probe and SPY-PHI were used to remove residual disease (FIG. 5D. Without IMI guided surgery, residual disease would have remained in the tumor bed and could have been a pertinent source of recurrent disease.

Example 4

Materials and Methods

This example illustrates materials and methods for the following examples.

Synthesis of DTPA-αGD2-IRDye800CW. 1 mg of anti-GD2 (Clone 14G2a, Bio X Cell, PBS) was added to 0.1 M sodium carbonate buffer, pH 9 (final pH 8.5-9). 25-fold molar excess of p-SCN-Bn-CHX-A"-DTPA (Macrocyclics) was added (37° C., 1 hr). Excess DTPA was removed by centrifugal ultrafiltration (Pierce Protein Concentrator, 10 kDa MWCO, ThermoScientific) using PBS as the diluent. Purity was confirmed by Size-Exclusion HPLC (Agilent 1260, Bio SEC-3, PBS, 0.3 mL/min) and DPTA substitution of 1.5-3.0 was confirmed with UV-Vis Spectrophotometry (BioTek Epoch with a Take3 plate). In the same buffer, purified DTPA-αGD2 was added to 4-fold molar excess of IRDye800CW-NHS ester (final pH 8.5-9) and incubated (RT, 30 min, with shaking). DTPA-αGD2-IRDye800CW was purified by ultrafiltration and protected from light until use. Purity was confirmed via SEC-HPLC, then concentration and IRDye800CW substitution were determined by UV-Vis Spectrophotometry before storage at less than 3 mg/ml.

DTPA-αGD2-IRDye800CW was radiolabeled with In-111 using the Nalla. method for radiolabeling DTPA-conjugated proteins with minimal modifications. Sodium citrate (500 mM) was added to the In-111 stock solution to bring the volume to 1.6 mL at pH 6. After 5 min, the probe was added and incubated (25° C., 30 min). The radiolabeling reaction progress was monitored by instant thin-layer chromatography (ITLC) developed in 50 mM sodium citrate eluent. Purity was determined by SEC-HPLC (BioSec3, PBS, 3 μm, 300 A, 4.6×300 mm, 0.4 mL/min). The buffer was exchanged with DPBS (Lonza, Cat #175512F12) for tail vein injections (11.11 MBq/nmol).

Evaluation of DTPA-αGD2-IRDye800CW. An ELISA was performed to assess changes in GD2-specific binding affinity after conjugation of the dye and chelator. Briefly, ganglioside GD2 (Advanced ImmunoChemical Inc.) was reconstituted (1 mg/mL) and immobilized on a microtiter plate (0.8 ug/well). After blocking with 1% BSA, a range of concentrations of αGD2 or DTPA-IRDye800CW-αGD2 were added (2.6-333 nM), followed by HRP-conjugated goat anti-human IgG Fc (Thermo Scientific), then visualized. Nonspecific binding was determined with GD2 immobilization and secondary antibody only, then total binding was corrected to yield specific binding, which was then fit by non-linear regression to yield the equilibrium dissociation constants (GraphPad Prism v9.4.1).

Orthotopic xenograft mouse model. Four- to six-week-old female athymic nude (nu/nu) (NCRNU-F sp/sp) mice (Taconic™), were maintained in a temperature-controlled animal facility with a 12-hour light/dark cycle in cohorts of five. Animals were kept in the facility for at least one week prior to performing any procedures, to minimize stress-related symptoms.

Under isoflurane anesthesia, a transverse left flank incision was made; and the left kidney and adrenal gland were exteriorized and maneuvered using a cotton tip applicator. One million SK-N-BE(2) neuroblastoma cells were suspended in a 20 μl of PBS and mixed with 20 μL of Matrigel basement membrane matrix (Corning™ Cat #354234) and implanted into the left adrenal gland and surrounding fat pad with a 30-gauge needle on a 1 cc syringe and the needle was slowly removed. The kidney and adrenal gland were returned to the abdominal cavity, the body wall was closed with 4-0 Polysorb, and the skin was closed with surgical wound clips. The animals recovered in a clean cage on a heating pad and were monitored until sternally recumbent and active. Wound clips were removed 10-14 days later.

Magnetic Resonance Imaging. MRI was performed 5 weeks after tumor injection on a 7T/30-cm A VIII spectrometer (Bruker Biospin, Billerica, MA) equipped with a 12 cm gradient set, a 40 mm quadrature RF volume coil, and Paravision 6.0.1 software. A T1-weighted Intragate FLASH sequence was used (repetition time (TR)/echo time (TE) =162/2.6 ms, field of view 40×40 mm, acquisition matrix 256×256, 13 slices, slice thickness 1 mm, and 1 average). Animals that reached USDA Class D sacrifice requirements were euthanized upon reaching these standards.

Handheld gamma detection, fluorescence detection, and biodistribution studies. $^{111}$In-αGD2-IRDye800CW was injected intravenously (50 ug and 3700 MBq in 100 uL DPBS) twenty-five days after SK-N-BE(2) injection and four days prior to biodistribution analysis. Control mice were injected with tracer and concomitant 10-fold molar excess of unlabeled αGD2. Gamma counts were measured percutaneously from the left flank (tumor), right flank, left and right hind limbs, tail, and chest using a Neoprobe gamma decay detector (Mammotome). NIR imaging was performed with the SPY-PHI NIR camera (Stryker) both pre-laparotomy and post-laparotomy with representative images recorded. Mice were then euthanized, and the indicated organs were harvested and weighed. Tissue-associated radioactivity was measured in a PerkinElmer Wizard 2 model 2480 gamma counter and quantified as percent injected dose per gram of tissue (% ID/g). In a separate experiment, tumors were grown in 3 mice and after 4.5 weeks, $^{111}$In-αGD2-IRDye800CW was injected intravenously (74.6 ug and 6300 MBq in 100 uL DPBS). Mice were euthanized 3 days later, organs were harvested and placed on a minimally fluorescent paper, and images were acquired with the SPY-PHI camera. Borders were drawn around each organ using ImageJ (NIH) and the average intensity was quantified. Average fluorescence from the brain (which had the lowest signal in each image, including the surrounding paper) was used as background signal and subtracted from the fluorescence of each organ.

In a separate experiment, tumors were grown in 10 mice and after 4.5 weeks, $^{111}$In-αGD2-IRDye800CW was injected intravenously (50 ug in 100 uL DPBS). Mice were euthanized 4 or 6 days later (n=5 each), organs were harvested and placed on a minimally fluorescent PLA plate, and images were acquired with the SPY-PHI camera. Regions of interest (ROIs) were drawn around each organ and a background region on images with uniformly enhanced brightness and contrast using ImageJ (NIH), and the average intensity of those ROIs was quantified on the original, unenhanced image (in arbitrary units per pixel$^2$, or AU/p$^2$), and the average intensity was quantified. Average background mean fluorescence was subtracted from the mean fluorescence of each organ.

Isotype control probe was synthesized by the same method as $^{111}$In-αGD2-IRDye800CW, but using a mouse IgG2 isotype control antibody (clone C1.18.4 in PBS, Bio X Cell #BE0085) instead. $^{111}$In-isotype-IR800 (n=4 on day 4 and n=3 on day 6) was injected intravenously into neuroblastoma-bearing mice as previously, and 4 or 6 days after tracer or control injection, mice were euthanized and the indicated organs were harvested and weighed. Tissue-associated radioactivity was measured in a PerkinElmer Wizard 2 model 2480 gamma counter and quantified as percent injected dose per gram of tissue (% ID/g). Organs were also placed on a minimally fluorescent PLA plate, and images were acquired with the SPY-PHI camera. ROIs were drawn and quantified as previously, and average background mean fluorescence was subtracted from the mean fluorescence of each organ.

To determine if residual disease was present following standard, non-IMI guided resection, and further demonstrate the ability of disclosed IMI systems to detect residual disease, four days post-tracer delivery to tumor-bearing mice, tumor resection was performed, without IMI guidance. The intraoperative systems were then used to inspect for residual disease, and if identified, used to guide additional resection until no further disease could be detected.

Figure 4A:
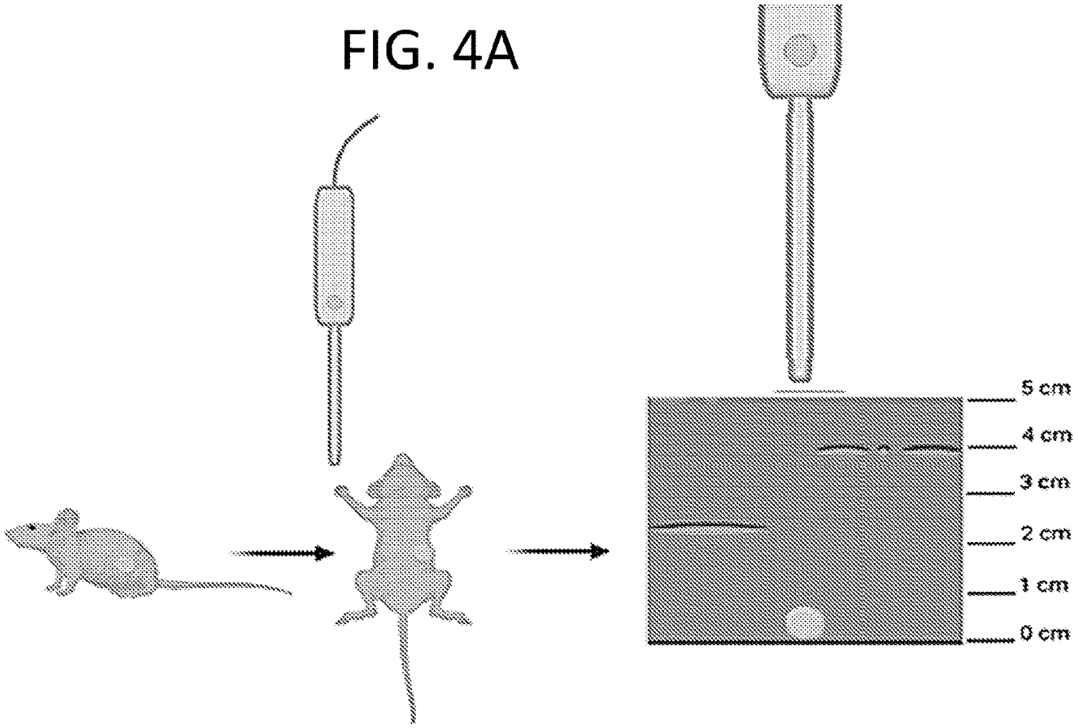
FIGS. 4A-4F. Handheld instruments can detect probe accumulation in the tumor.
Figure 4B:
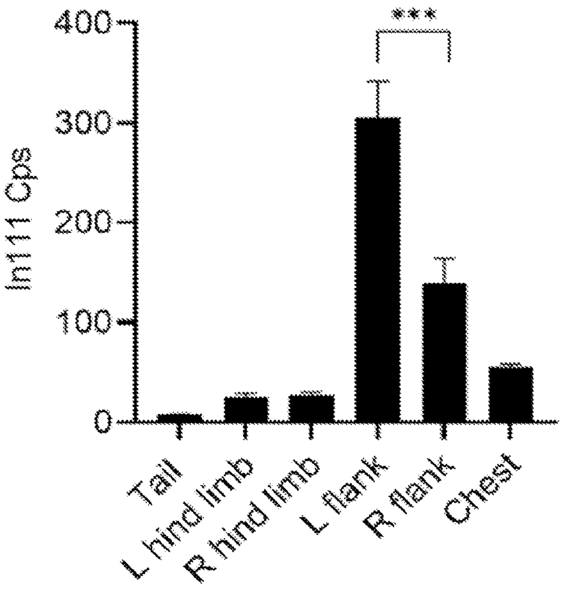

Tissue Phantom Studies. NB xenografts harvested from tumor-bearing mice for the biodistribution studies (n=4) were then implanted below 5 cm of processed tissue (FIG. 4A). Handheld instruments were used above the processed tissue and gamma decay and fluorescence were recorded with the removal of 5 mm increments of tissue, until the implanted xenograft was reached.

Image Processing and Statistical Analysis. MRI images were processed using VivoQuant, DSI Studio and RadiAnt software. Images for the fluorescence biodistribution were analyzed with ImageJ (NIH). Graphing and statistical analyses were performed using Prism GraphPad v10. Organ uptake (% ID/g) in the biodistribution experiments is reported as mean±SEM. Probe accumulation within organs was compared using one-way ANOVA (or two-way ANOVA for day 4 gamma biodistribution, as both organ uptake and probe only vs probe and block were compared) and if significant, the Sidak post-hoc test was used to compare the uptake of each organ to the tumor uptake.

Example 5

Figure 2C:
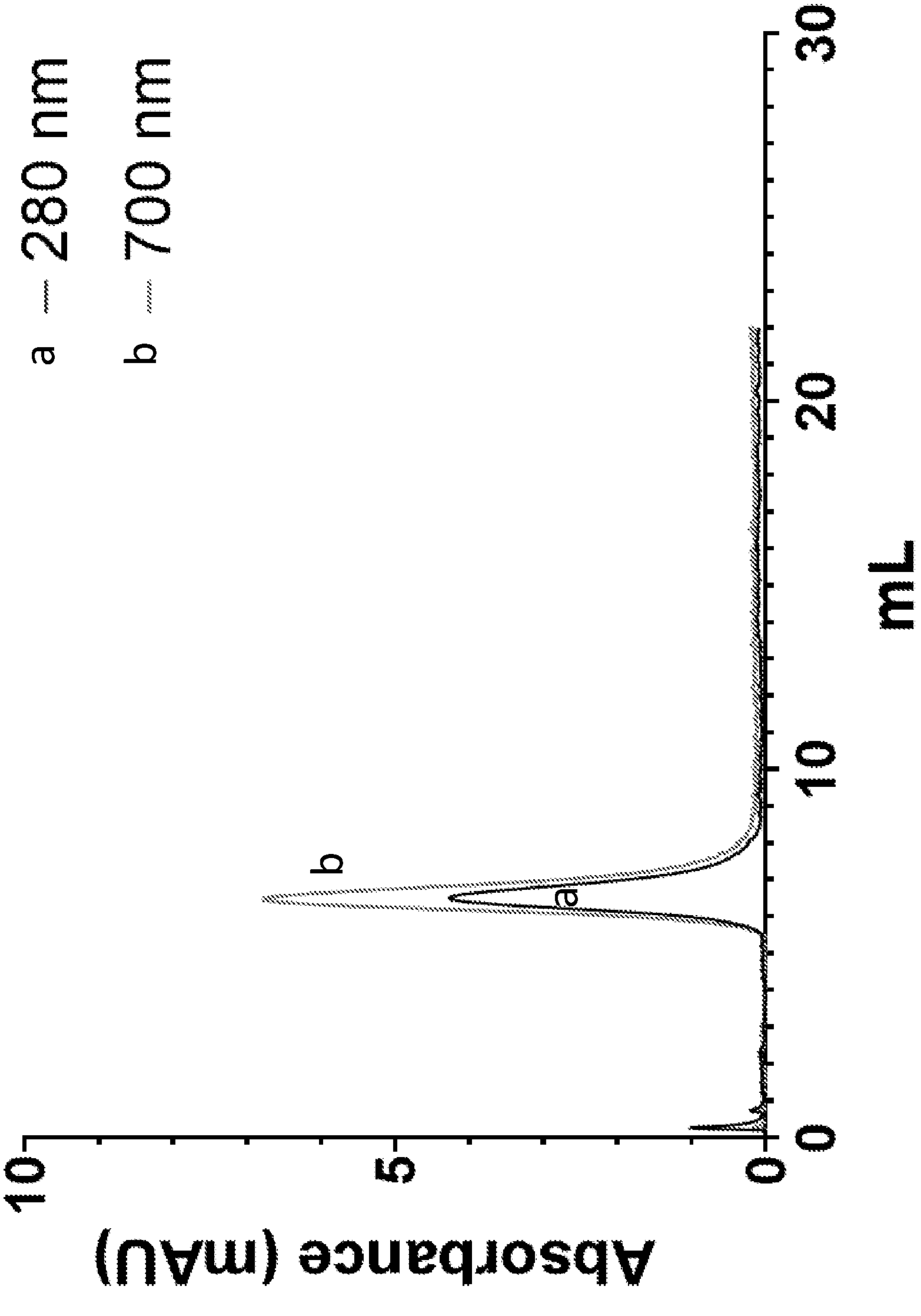

DTPA-αGD2-IRDye800CW Characterization $^{111}$In-αGD2-IRDye800CW was synthesized with high radiochemical yield (>99%) at the target molar activity (11.11 MBq/nmol). The substitution level of DTPA varied from 1 to 1.5 DTPA/antibody and the NIR-dye was 2-2.5 dyes/antibody, as determined by UV-Vis spectra comparing absorbance at 700 nm (IRDye800-CW) versus 280 nm (protein) (FIG. 2C). When performed with more than 4-fold excess of IRDy800CW to αGD2, there was slight precipitation of the antibody. With 4-fold excess, no precipitation was observed on visual inspection and aggregation was not seen with SEC-HPLC (FIG. 2C). The binding affinity for αGD2 and DTPA-αGD2-IRDye800CW are $K_d$=2.39 nM (0.99-4.62 nM, 95% CI) and $K_d$=21.31 nM (14.06-32.16 nM, 95% CI) respectively.

Example 6

MRI and Biodistribution Analysis

Figure 3A:
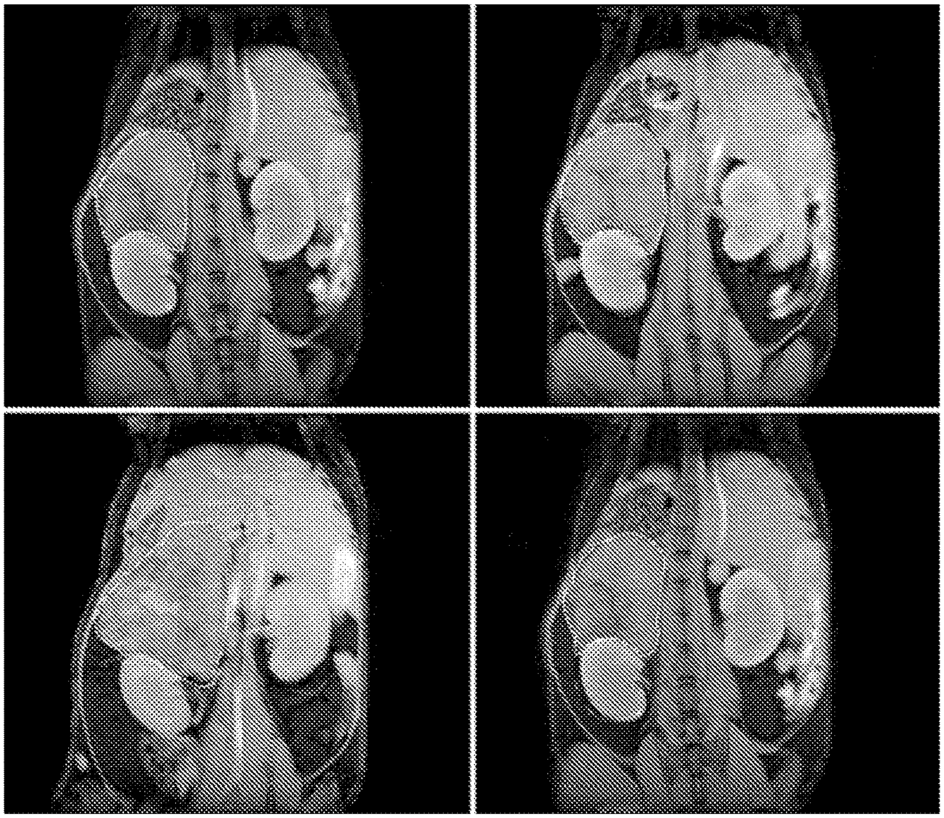
FIGS. 3A-3N.

MR imaging five weeks post orthotopic injection (n=19) revealed tumors of an average volume of 907.5 mm$^3$±44.6 (13.8±0.24 mm in largest dimension). In several of the mice, the left kidney was embedded within the tumor at this timepoint (FIG. 3A).

Figure 3B:
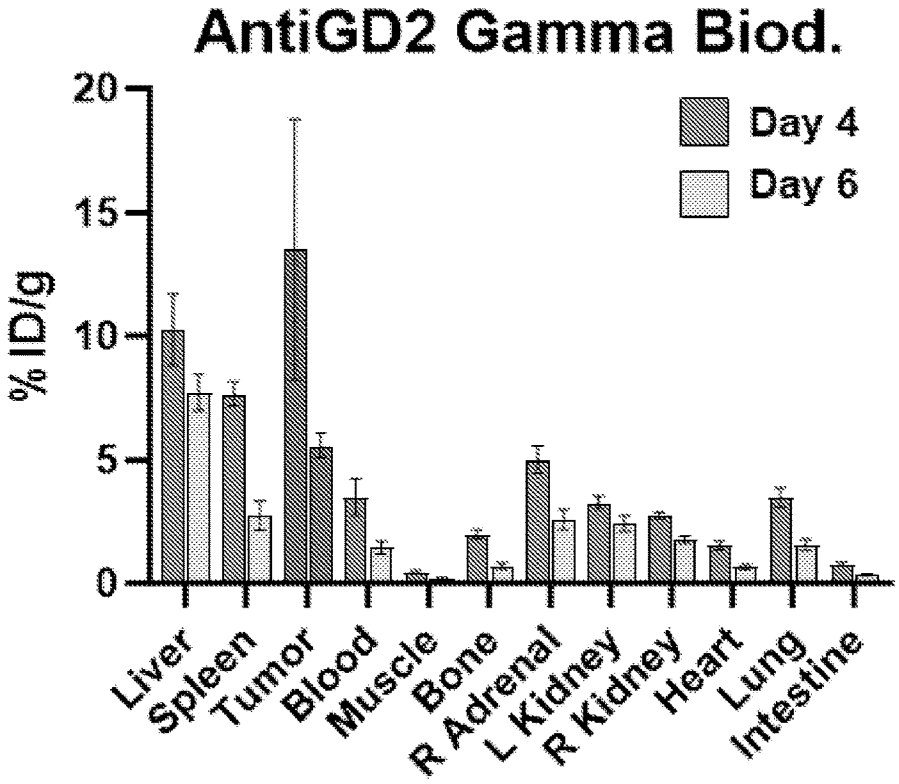
(FIG. 3B) Gamma count biodistribution of $^{111}$In-αGD2-IRDye800CW as percent injected dose per gram of tissue (% ID/g) in orthotopic xenograft neuroblastoma 4 days after probe injection and 6 days after probe injection.
Figure 3C:
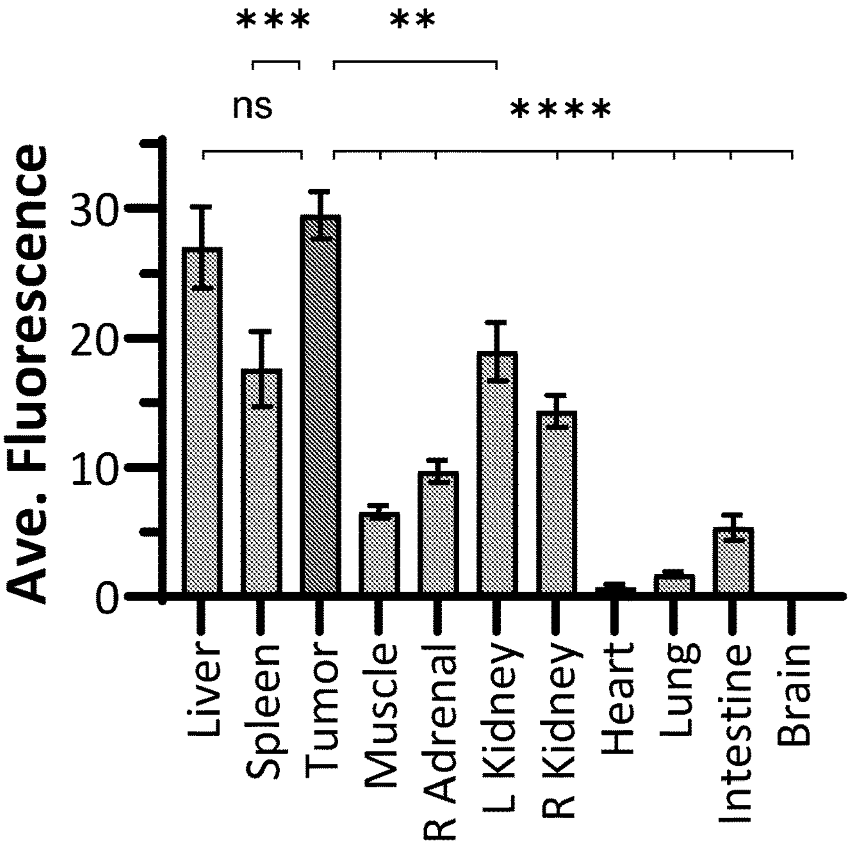
(FIG. 3C) Fluorescence biodistribution 3 days after probe injection, normalized to brain fluorescence (* for $p<0.01$,  for $p<0.001$, and * for $p<0.0010$; Statistical analysis-ANOVA with Sidak's multiple comparisons post-hoc test, with comparisons to tumor only).
Figure 3D:
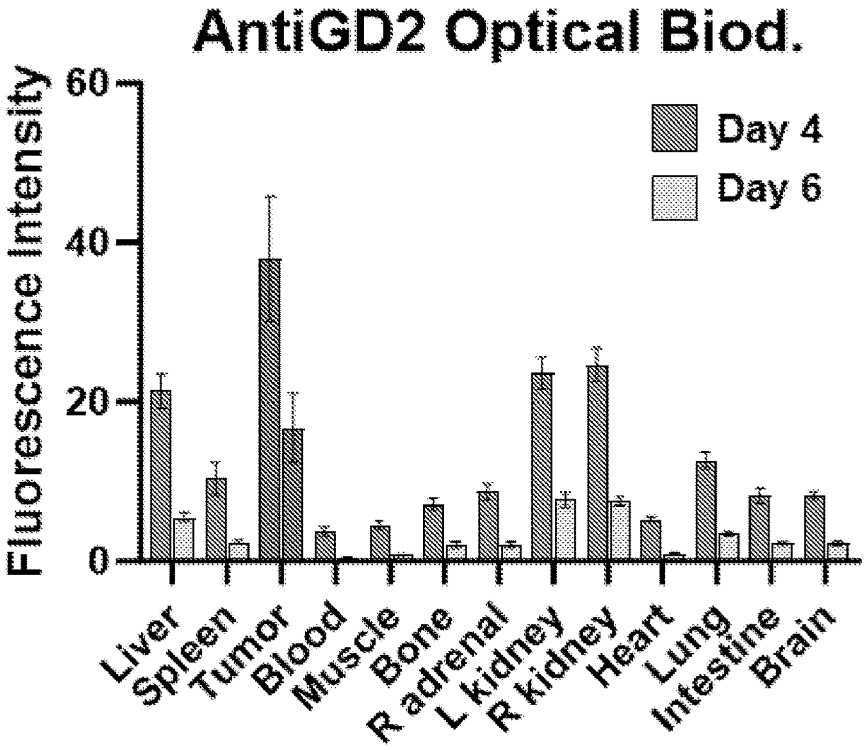
(FIG. 3D) Fluorescence biodistribution 4 and 6 days after probe injection, with background subtracted, not normalized. Tumor is significantly different from all other organs.
Figure 3E:
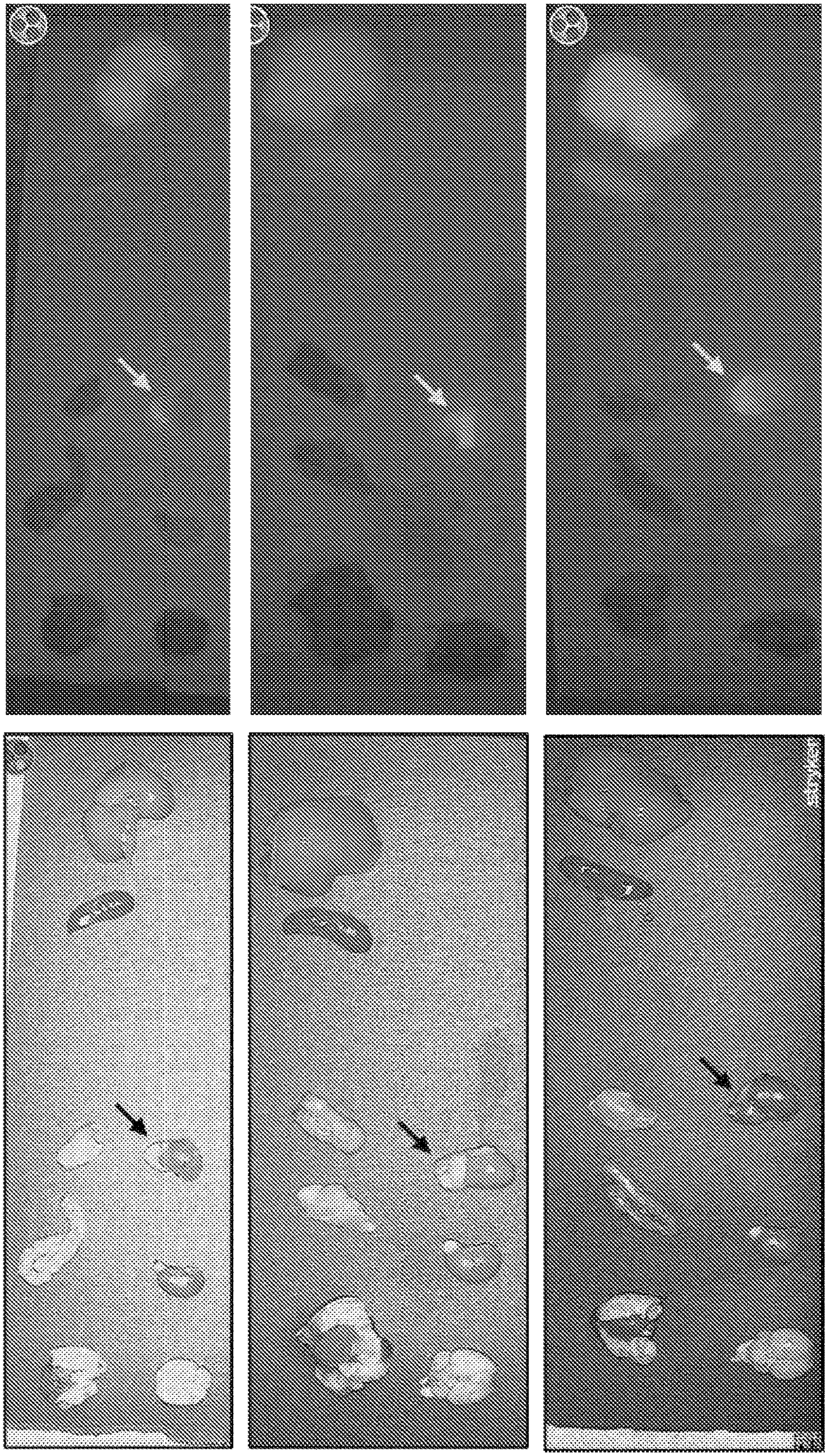
(FIG. 3E) White light (left) and fluorescence (right) SPY-PHI images of ex vivo organs used for fluorescence biodistribution analysis 3 days after probe injection (with each fluorescent image uniformly increased in brightness and contrast). Organs in a clockwise order from the upper left are the heart and lungs, small intestine, muscle, spleen, liver, left kidney and tumor (arrow points to tumor), right kidney and adrenal, and brain (muscle and small intestine are reversed in middle panels).
Figure 3F:
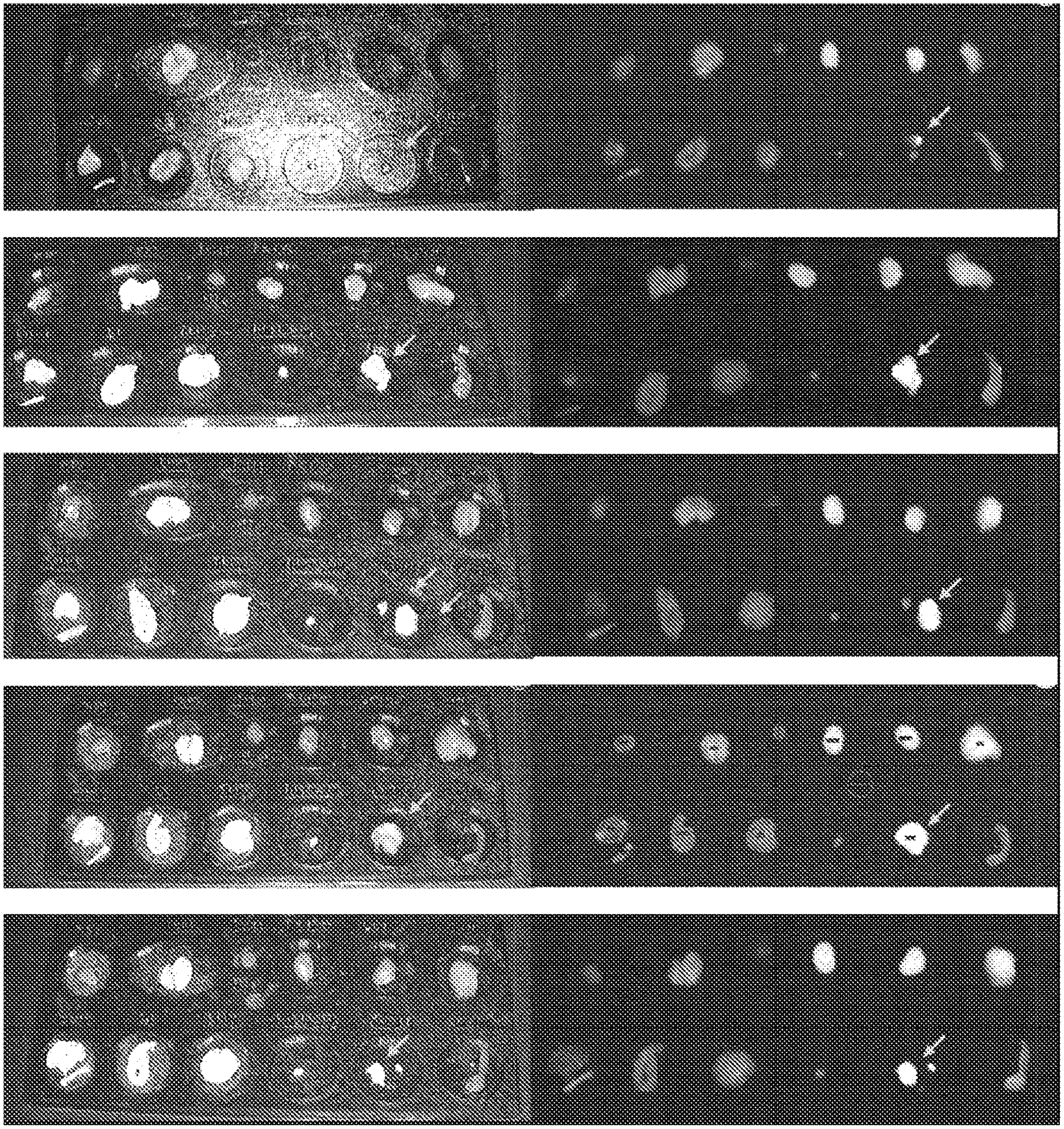
(FIG. 3F) White light (left) and fluorescence (right) SPY-PHI images of ex vivo organs 4 days after probe injection (with each fluorescent image uniformly increased in brightness and contrast). Arrows point to tumors. Clockwise from the upper left are heart, lung, blood, right kidney, left kidney, liver, spleen, tumor, right adrenal, brain, intestine, and muscle & bone.
Figure 3G:
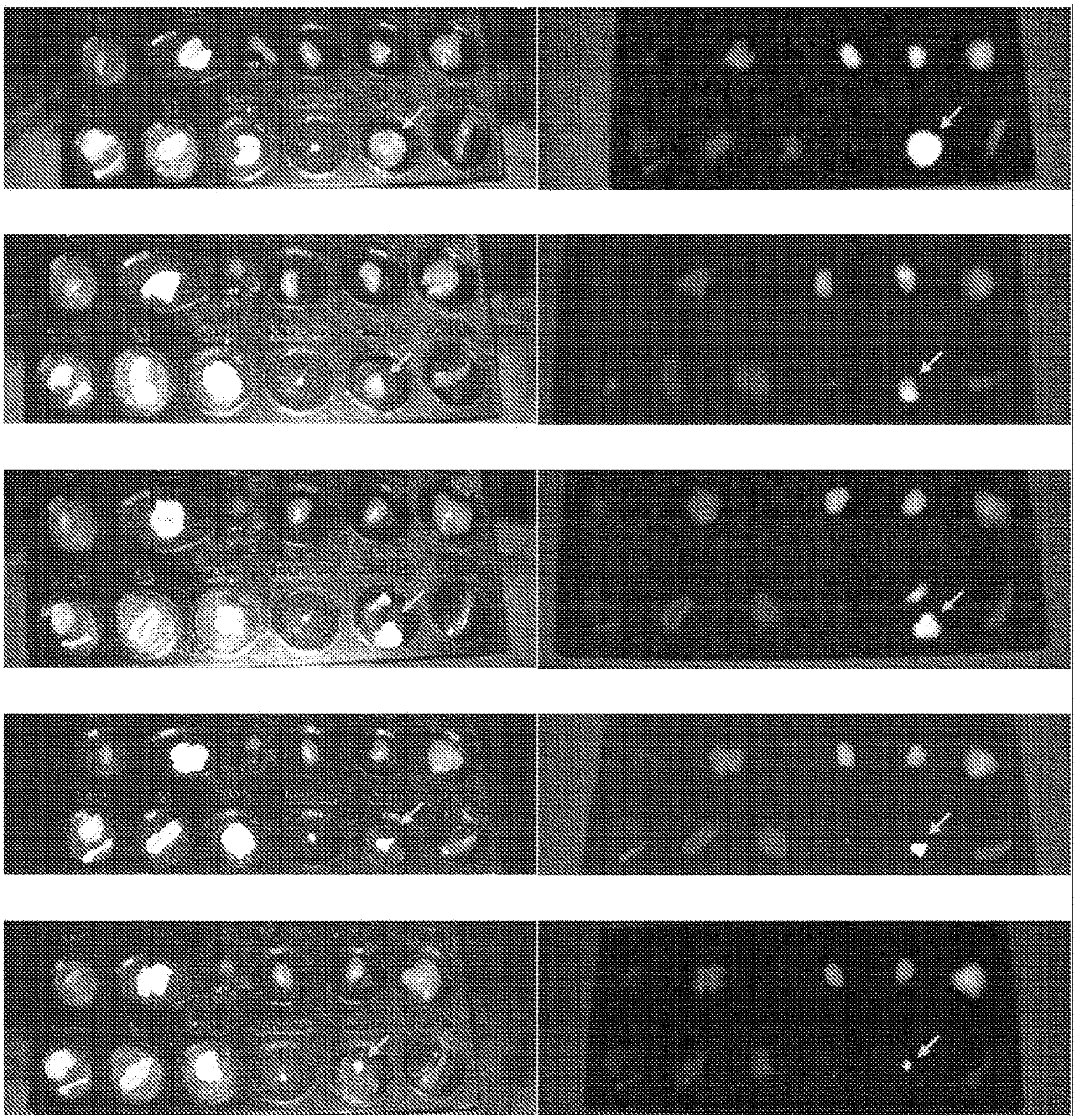
(FIG. 3G) White light (left) and fluorescence (right) SPY-PHI images of ex vivo organs 6 days after probe injection (with each fluorescent image uniformly increased in brightness and contrast). Arrows point to tumors. Clockwise from the upper left are heart, lung, blood, right kidney, left kidney, liver, spleen, tumor, right adrenal, brain, intestine, and muscle & bone.
Figure 3H:
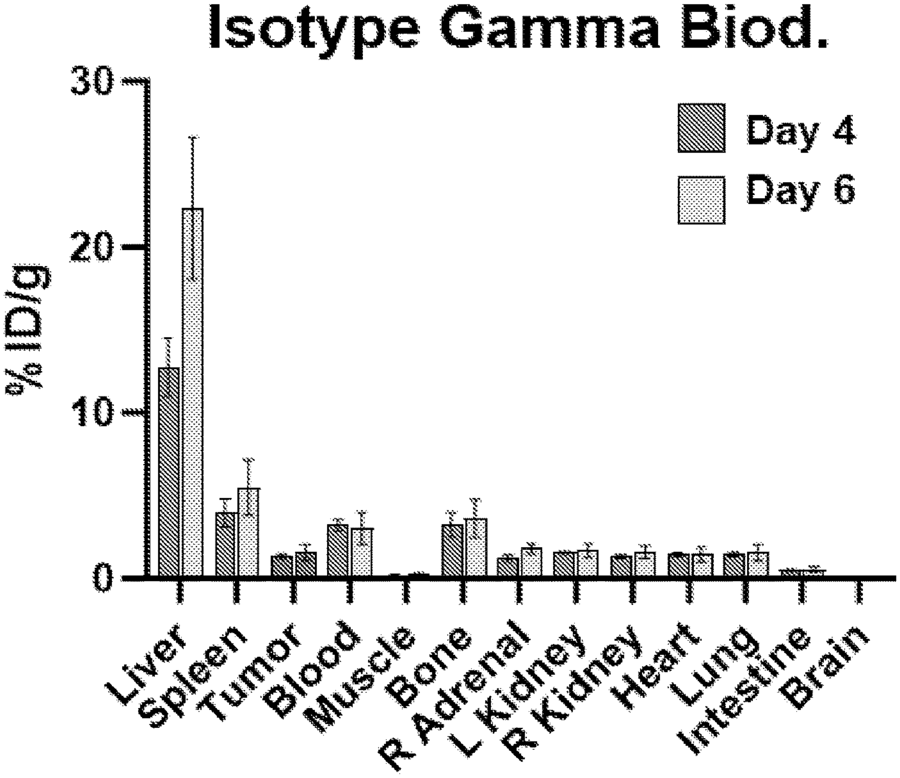
(FIG. 3H) Gamma count biodistribution of isotype control as % ID/g in orthotopic xenograft neuroblastoma 4 and 6 days after probe injection.

Specific accumulation of $^{111}$In-αGD2-IRDye800CW or $^{111}$In-isotype-IR800 in GD2-expressing neuroblastoma tumors was examined by gamma decay count and fluorescence biodistribution analysis 4 and 6 days after probe injection, with and without the addition of unlabeled αGD2 antibody on day 4 or 6 (FIG. 3B). On both days, $^{111}$In-αGD2-IRDye800CW accumulated significantly more in tumor tissue than almost all other measured organs while $^{111}$In-isotype-IR800 did not (FIG. 3H).

On day 4 (n=7 for probe only), retention was significantly higher in the tumor (13.49±5.26% ID/g) than the blood (3.49±0.75% ID/g; p<0.0001) and muscle (0.45±0.06% ID/g; p<0.0001), with ratios of 3.87 and 30.0, respectively. As is common with antibody-based tracers, non-specific accumulation was noted in the liver (10.25±1.45% ID/g; p=ns) and the spleen (7.659±0.50% ID/g, p=ns). The tumor of one mouse was 2.3 standard deviations above the average, though when data from that mouse were removed, tumor uptake was still significantly higher than all other organs except the spleen and liver. All other data points were within 2 standard deviations of the mean for the same organ. No significant difference was observed with the dinutuximab block (n=5; data not shown).

On day 6 (n=6), tumor uptake (5.58±0.47% ID/g) was similarly significantly higher than all other organs except the liver (7.70±0.73% ID/g, $p<0.01$), including the blood (1.44±0.26% ID/g; $p<0.0001$) and muscle (0.19±0.01% ID/g; $p<0.0001$), with ratios of 3.88 and 29.4, respectively. Of note, a seventh mouse had been removed from the analysis because of an uncorrectable data collection error. At both timepoints, $^{111}$In-isotype-IR800 accumulation was not significantly higher in tumor than any other organ (but significantly lower than the spleen on day 4 and the liver on both days; FIG. 3H).

Fluorescence biodistribution using the SPY-PHI camera and ImageJ analysis yielded similar results. At 3 days after injection, the fluorescence of brain tissue, with the least fluorescence in all specimens, was subtracted as background signal (FIGS. 3C & E). Average fluorescence intensity was significantly higher in tumor versus all other organs ($p<0.002$) except for liver (p=ns), with a tumor-to-muscle ratio of 4.5.

Figure 3I:
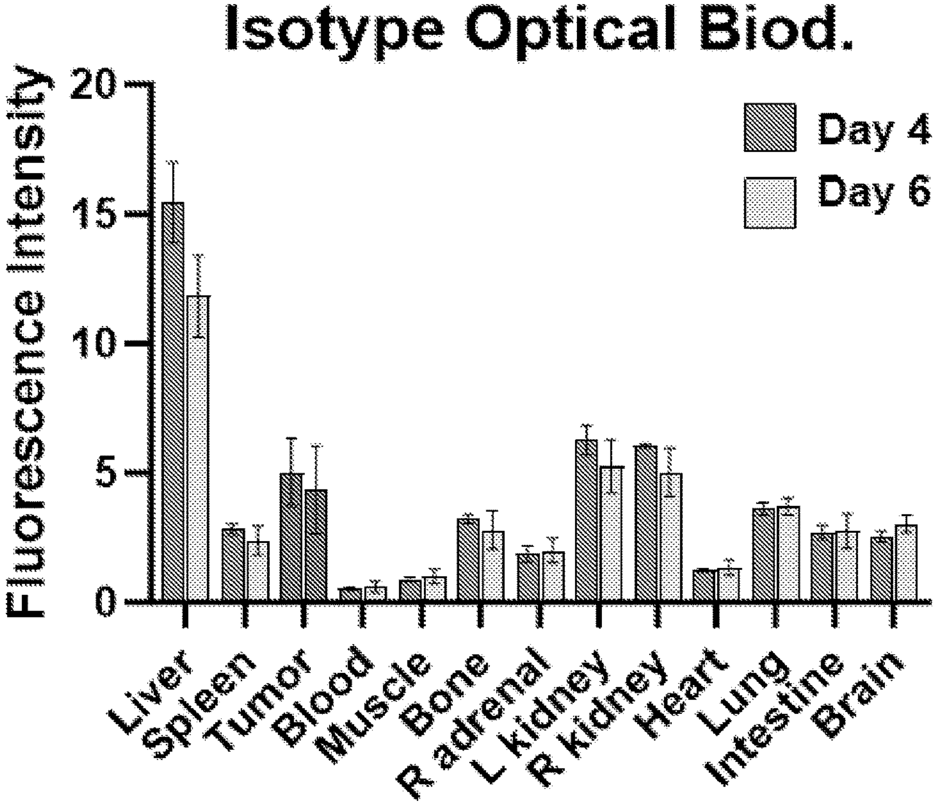
(FIG. 3I) Fluorescence biodistribution of isotype control 4 and 6 days after probe injection (with background subtracted).
Figure 3J:
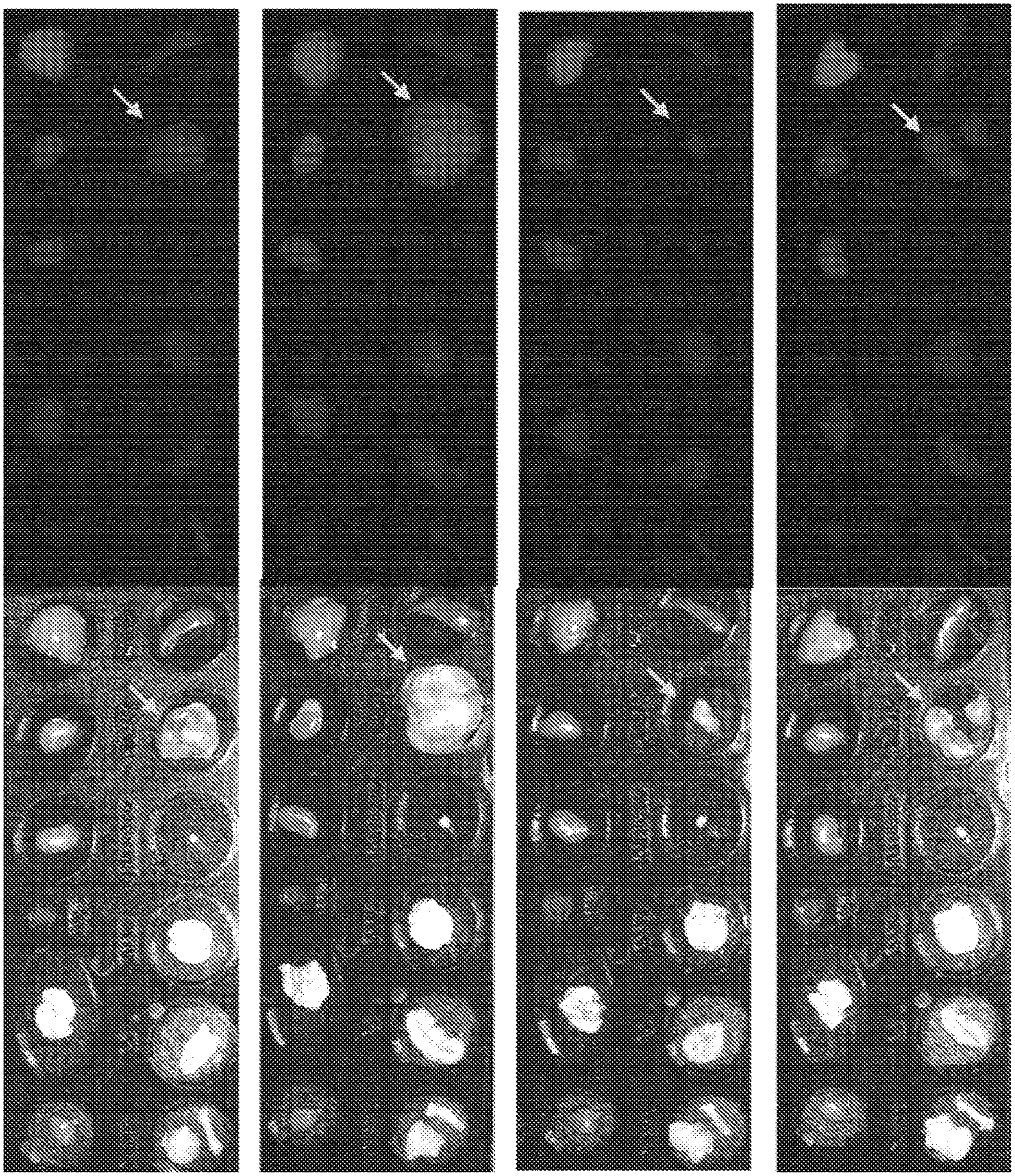
(FIG. 3J) White light (left) and fluorescence (right) SPY-PHI images of ex vivo organs 4 days after isotype control tracer injection (with each fluorescent image uniformly increased in brightness and contrast). Arrows point to tumors. Clockwise from the upper left are heart, lung, blood, right kidney, left kidney, liver, spleen, tumor, right adrenal, brain, intestine, and muscle & bone.
Figure 3K:
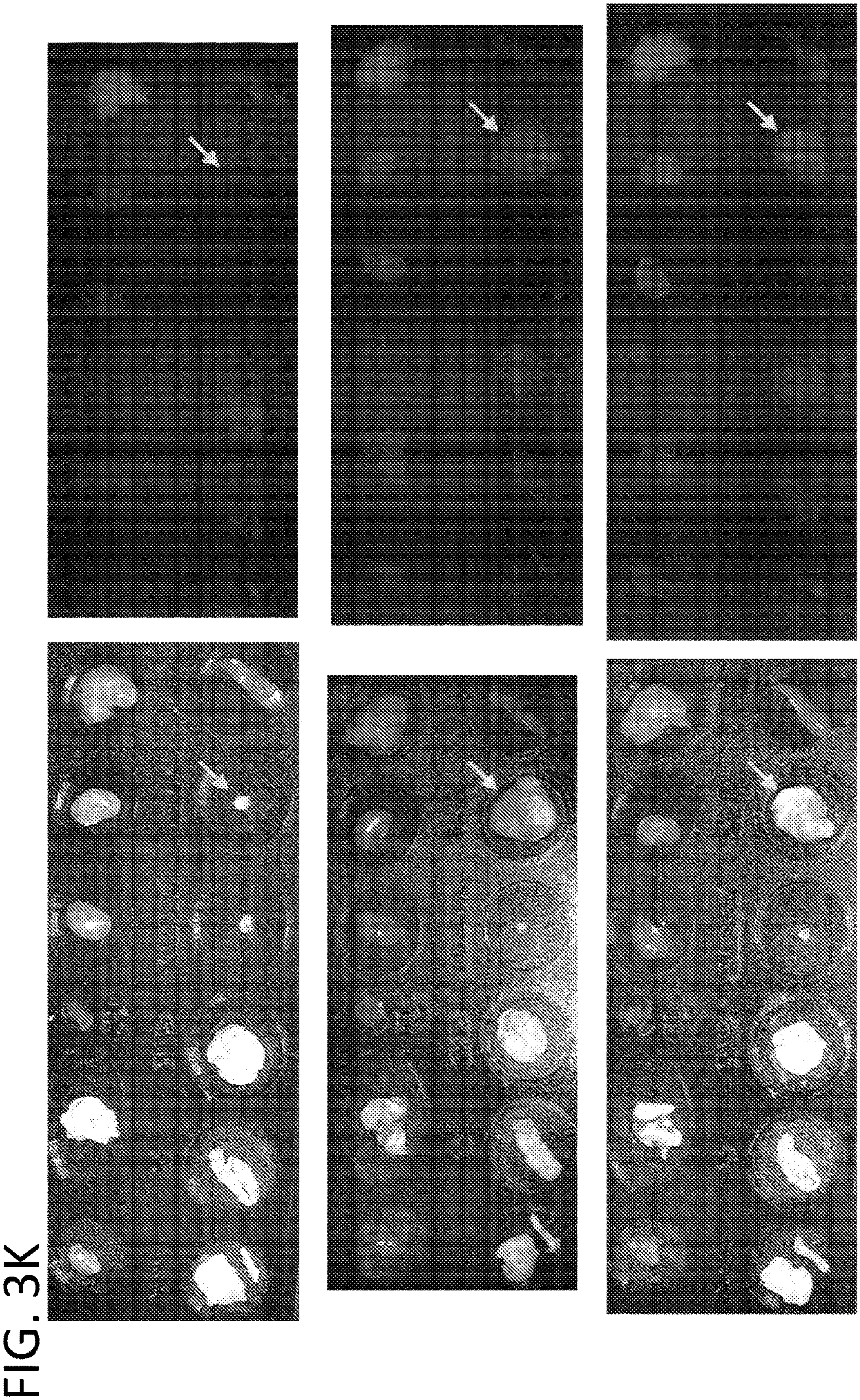
(FIG. 3K) White light (left) and fluorescence (right) SPY-PHI images of ex vivo organs 6 days after isotype control tracer injection (with each fluorescent image uniformly increased in brightness and contrast). Arrows point to tumors. Clockwise from the upper left are heart, lung, blood, right kidney, left kidney, liver, spleen, tumor, right adrenal, brain, intestine, and muscle & bone.
Figure 3L:
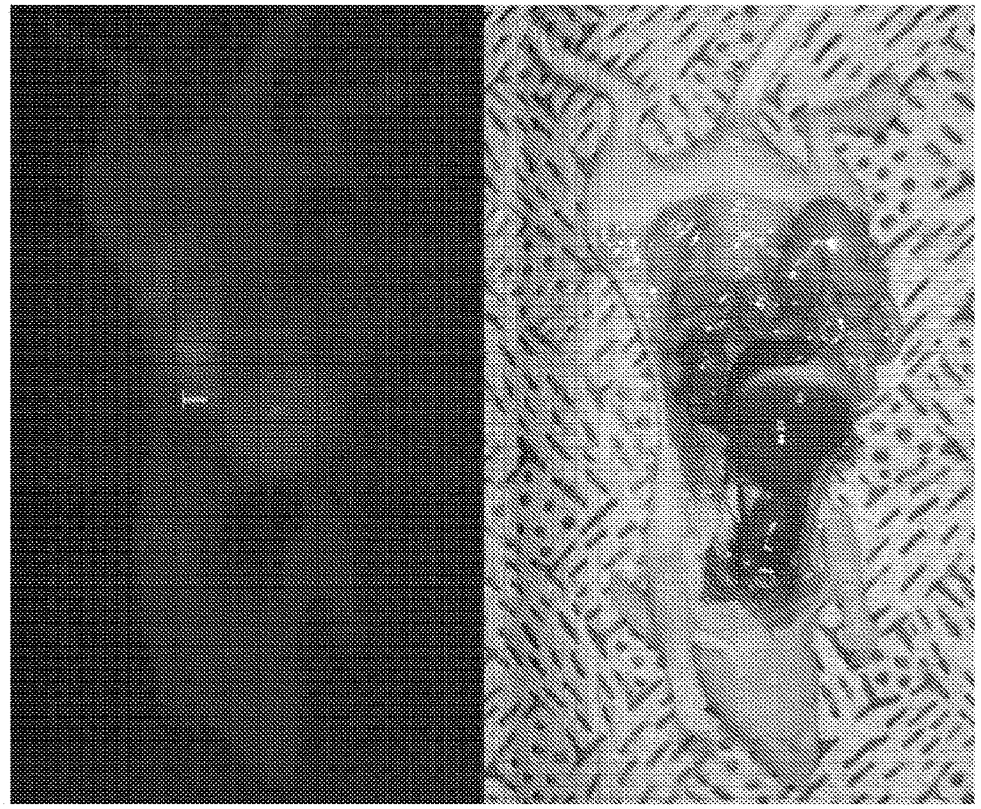
Figure 3M:
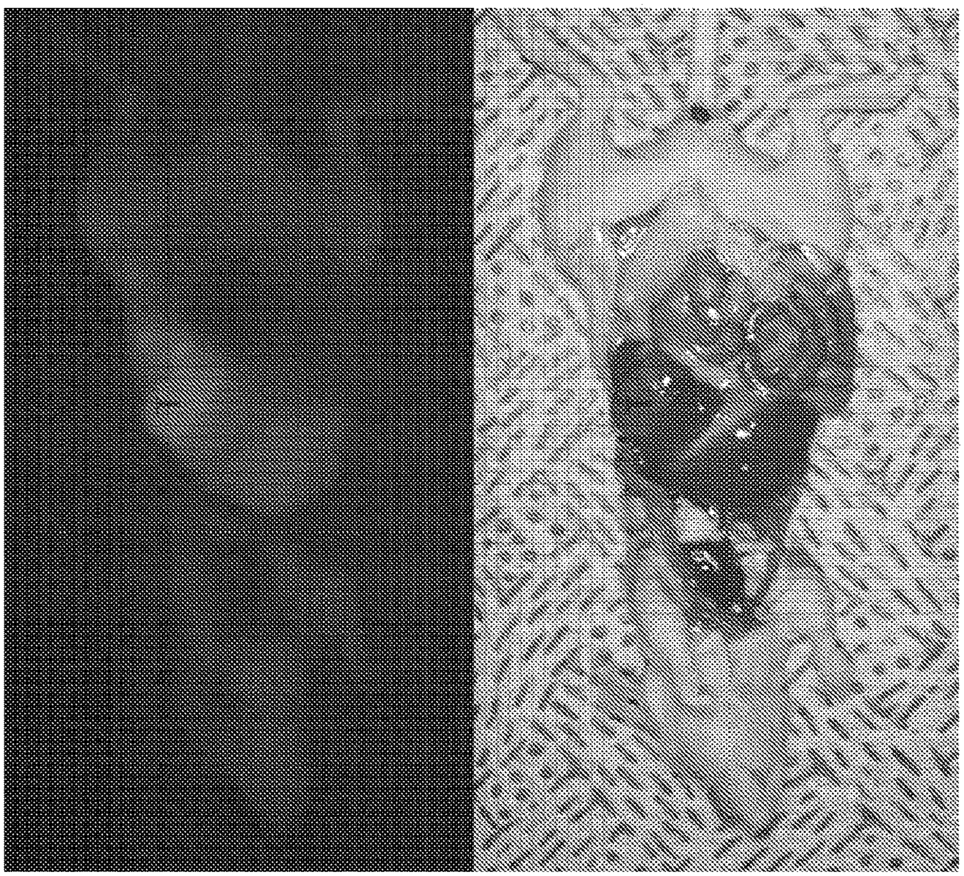
Figure 3N:
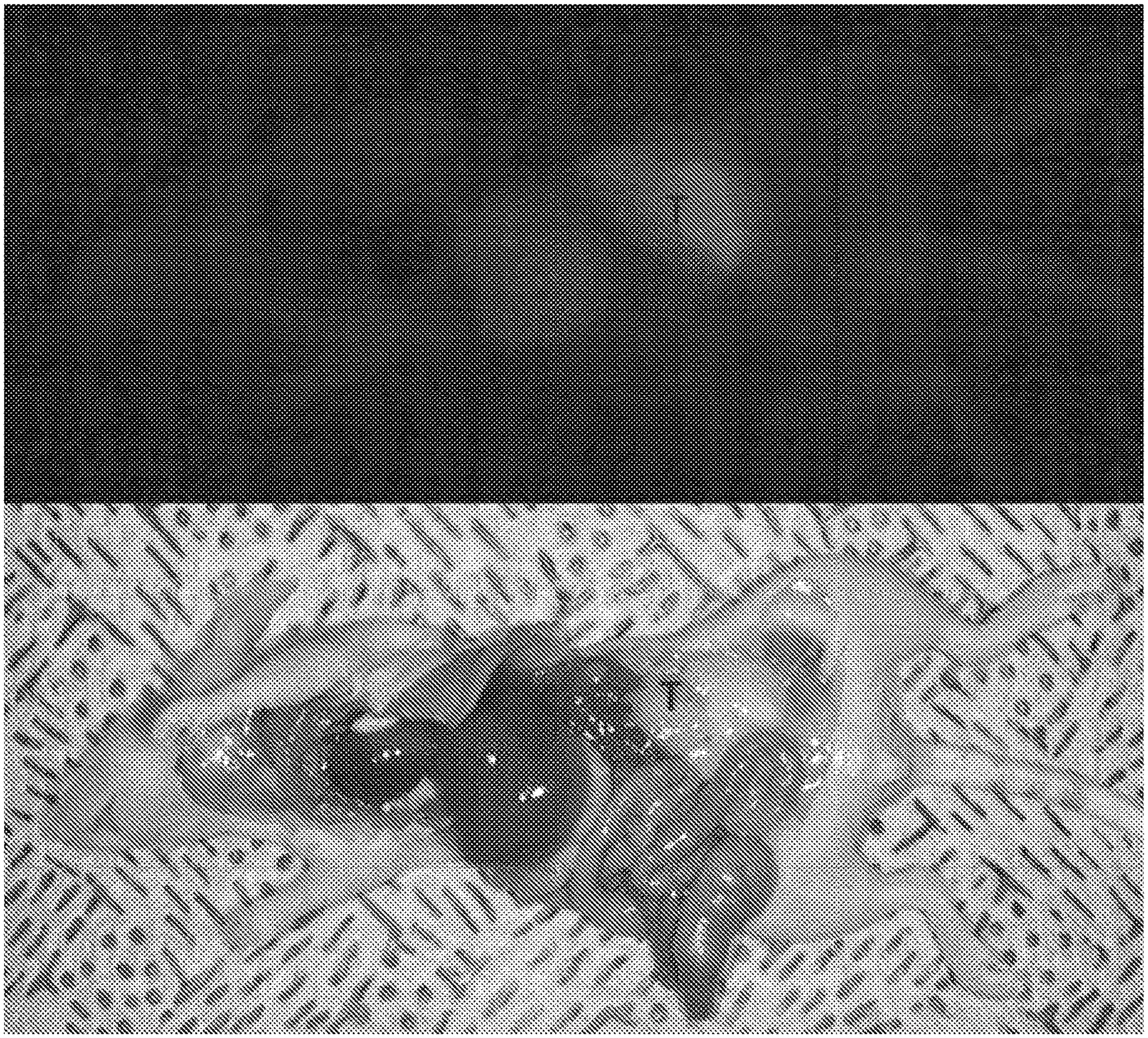

On days 4 and 6, average fluorescence intensity was significantly higher in tumor (37.9±7.88 AU/$p^2$ on day 4 and 16.8±4.30 AU/$p^2$ on day 6) versus all other organs ($p<0.001$; FIGS. 3D, F, and G). On day 4, there was accumulation in the liver (21.3±2.12 AU/$p^2$), blood (3.80±0.54 AU/$p^2$) and muscle (4.57±0.52 AU/$p^2$), with tumor-to-blood and -muscle ratios of 9.97 and 8.29, respectively. Similarly on day 6, fluorescence of the tumor was higher than other organs including the liver (5.54±0.56 AU/$p^2$), blood (0.43±0.15 AU/$p^2$), and muscle (0.808+/−0.045 AU/$p^2$), with tumor-to-blood and tumor-to-muscle ratios of 39.1 and 20.8, respectively. No difference was seen with co-administered 50 μg dinutuximab block on day 6 (n=5; data not shown). With $^{111}$In-isotype-IR800, tumor brightness was low (5.03±1.3 AU/$p^2$ on day 4 and 4.34±1.69 AU/$p^2$ on day 6; FIG. 3I-K). On day 4, isotype control fluorescence was significantly higher than heart (1.24±0.06 AU/$p^2$; $p<0.001$), blood (0.521±0.06 AU/$p^2$; $p<0.0001$), muscle (0.89±0.09 AU/$p^2$; $p<0.001$), and adrenal (1.88±0.31 AU/$p^2$; $p<0.01$), while significantly lower than liver (15.4±1.55 AU/$p^2$; $p<0.0001$). On day 6, it was only significantly higher than blood (0.59±0.20 AU/$p^2$; $p<0.05$) and lower than liver (11.82±1.59 AU/$p^2$; $p<0.0001$).

Isotype control probe had extremely low accumulation on both days (1.34±0.15% ID/g and 1.56±0.52% ID/g) and did not accumulate significantly more in the tumor than in any other organ (FIG. 3H). While accumulated $^{111}$In-isotype-IR800 had greater fluorescence in the tumor versus some background organs, it remained overall quite low (5.03±1.3 AU/$p^2$ on day 4 and 4.34±1.69 AU/$p^2$ on day 6; FIG. 3I) and significantly lower than the liver. The accumulation of the GD2-targeted probe but not the isotype control probe indicates specific binding of the antiGD2 probe in the tumor rather than accumulation due to the enhanced permeability and retention (EPR) effect.

Example 7

Handheld Clinical IMI Detection Systems

Figure 4C:
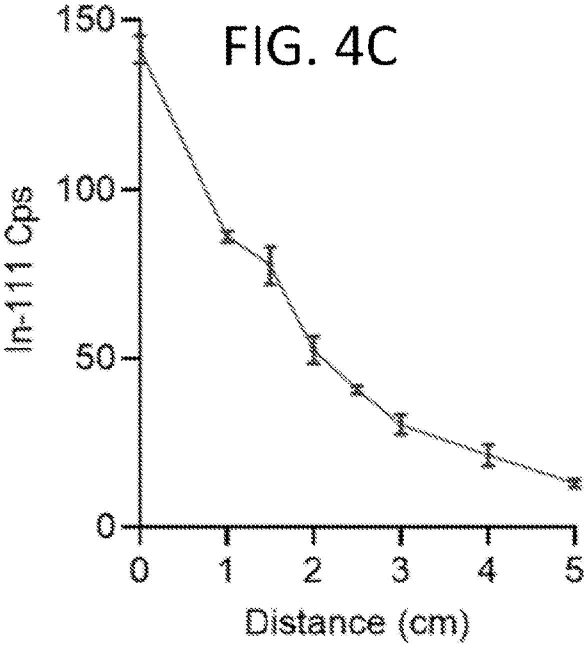
Figure 4D:
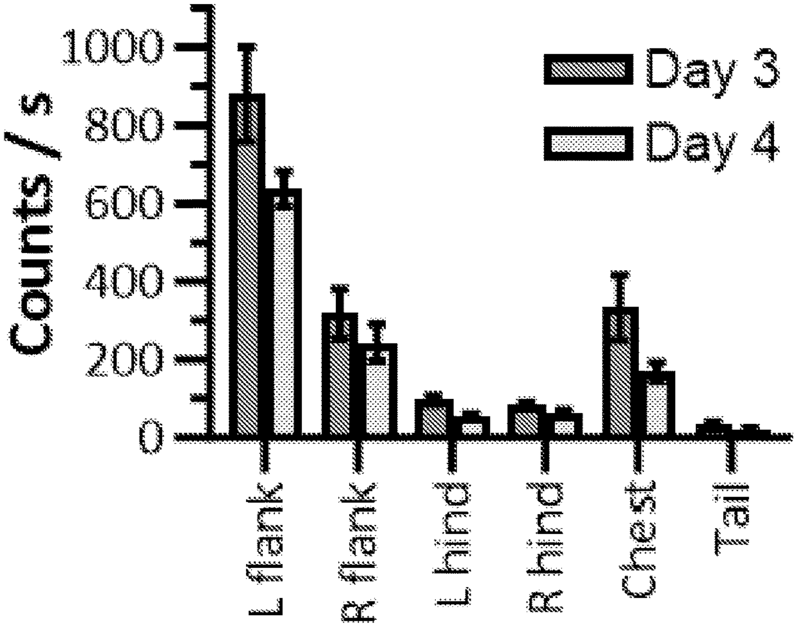
Figure 4E:
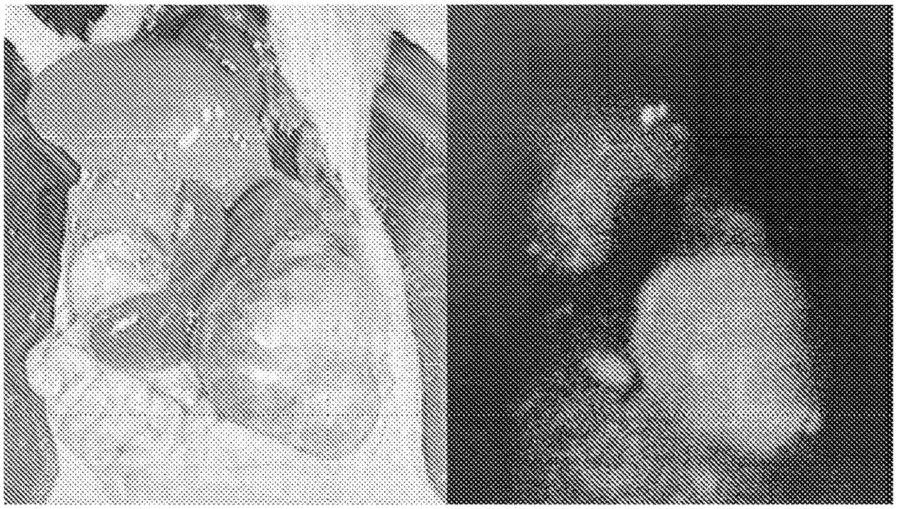
Figure 4F:
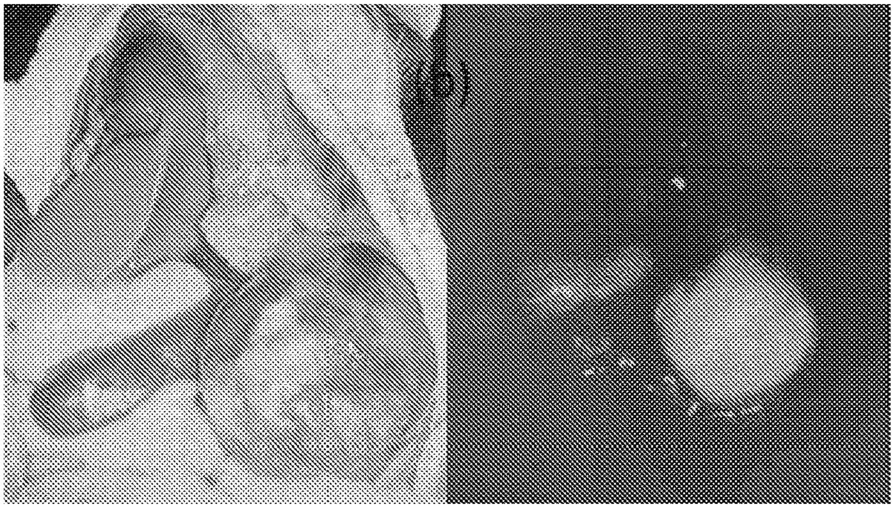

To evaluate tracer detection in vivo, neuroblastoma-bearing mice (n=15) received tail vein injections of $^{111}$In-αGD2-IRDye800CW (3700 MBq in 50 μg in 100 μL DPBS). Three and four days later, gamma decay was measured percutaneously with the handheld Neoprobe over various regions of the body, including the left flank (tumor region). At both time points, the gamma decay signal was significantly higher in the left flank than in any of the other body regions (FIG. 4D; $p<0.0001$). No difference was seen on either day between probe only and probe with 10× blocking antibody. Immediately afterwards, fluorescent signal was evaluated with the handheld NIR camera. The tumor demonstrated strong qualitative fluorescence with the SPY-PHI with little surrounding signal on days 3 and 4 (FIGS. 4E, 4F, and 3E).

Tumors harvested from mice at days 3 and 4 (n=5) were implanted in processed tissue cubes to evaluate the effect of tumor depth on gamma and fluorescent signal detection. Gamma signal was detected at 5 cm of tissue depth when the probe was aimed directly at the tumor, but no signal was detected when the probe was angled away more than ~5 degrees or moved laterally. Gamma detection increased in a linear fashion as 5 mm slices were removed from the tissue cube (FIG. 4A, 4C). Fluorescence could not be visualized until only 5 mm of processed tissue covered the tumor.

Example 8

$^{111}$In-Dinutuximab-IRDye800CW

Synthesis of $^{111}$In-Dinutuximab-IRDye800CW.

To generate DTPA-αGD2-IR800 or DTPA-isotype-IR800, 1 mg of anti-GD2 (Clone 14G2a in PBS, Bio X Cell #BE0318) or mouse IgG2a isotype control (clone C1.18.4 in PBS, Bio X Cell #BE0085) was added to 0.1 M sodium carbonate buffer, pH 9 (final pH 8.5-9). 15- to 25-fold molar excess of p-SCN-Bn-CHX-A"-DTPA (Macrocyclics) was added (37° C., 1 hr). Excess DTPA was removed by centrifugal ultrafiltration (Pierce Protein Concentrator, 10 kDa MWCO, ThermoScientific) using PBS as the diluent. Purity was confirmed by Size-Exclusion HPLC (Agilent 1260, Bio SEC-3, PBS, 0.3 mL/min) and DPTA substitution of 1.0-3.0 was confirmed with UV-Vis Spectrophotometry (BioTek Epoch with a Take3 plate). In the same buffer, purified DTPA-αGD2 or DTPA-isotype was added to 4-fold molar excess of IRDye800CW-NHS ester (final pH 8.5-9) and incubated (RT, 30 min, with shaking). DTPA-αGD2-IR800 or DTPA-isotype-IR800 was purified by ultrafiltration and protected from light until use. Purity was confirmed via SEC-HPLC, then concentration and IRDye800CW substitution were determined by UV-Vis Spectrophotometry before storage at less than 3 mg/ml.

DTPA-αGD2-IR800 or DTPA-isotype-IR800 was radiolabeled with In-111 using the Nalla et al. method for radiolabeling DTPA-conjugated proteins with minimal modifications.[30] Sodium citrate (500 mM) was added to the In-111 stock solution to bring the volume to 1.6 mL at pH 6. After 5 min, the probe was added and incubated (25° C., 30 min). The radiolabeling reaction progress was monitored by instant thin-layer chromatography (iTLC) developed in 50 mM sodium citrate eluent. The buffer was exchanged with DPBS (Lonza, Cat #175512F12) for tail vein injections. Purity was determined by SEC-HPLC (BioSec3, PBS, 3 μm, 300 A, 4.6×300 mm, 0.4 mL/min), and purification repeated until >95% pure.

Figure 6A:
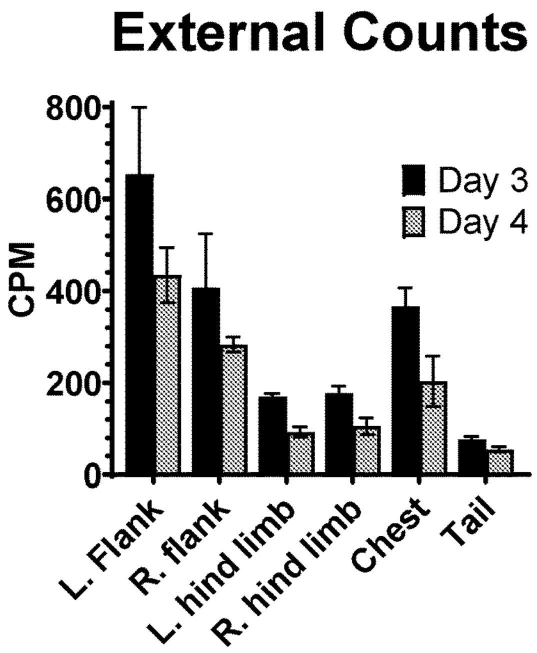
FIGS. 6A-6E.
Figure 6B:
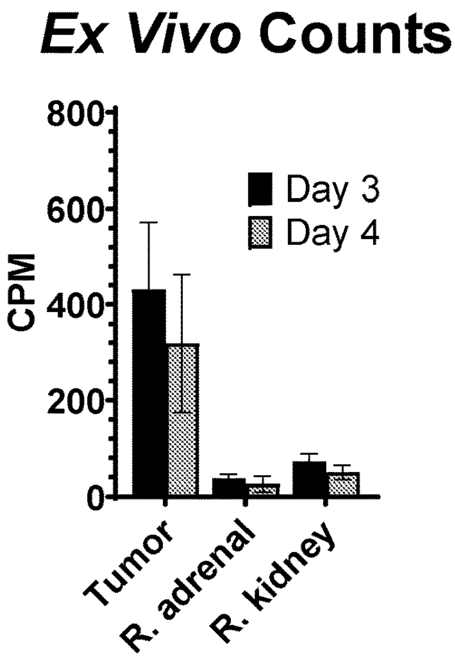
Figure 6C:
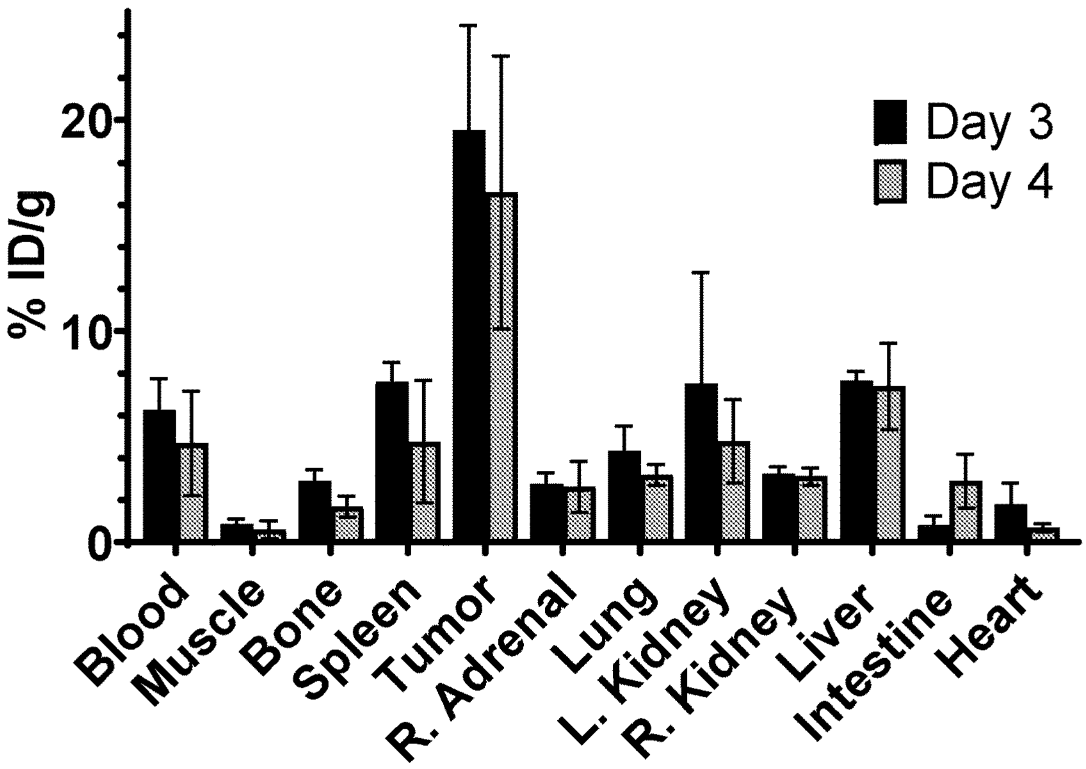
Figure 6D:
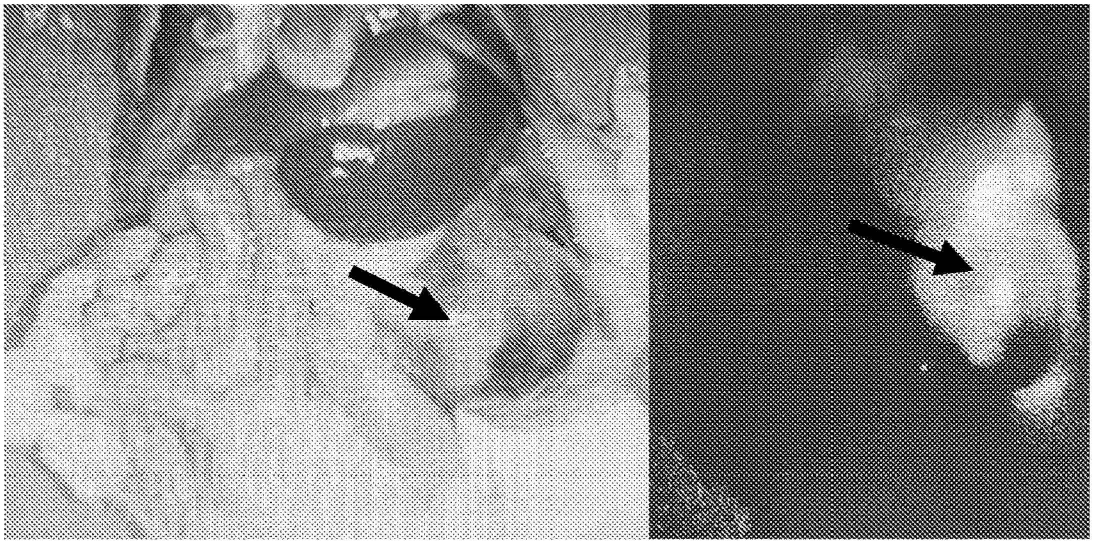
Figure 6E:
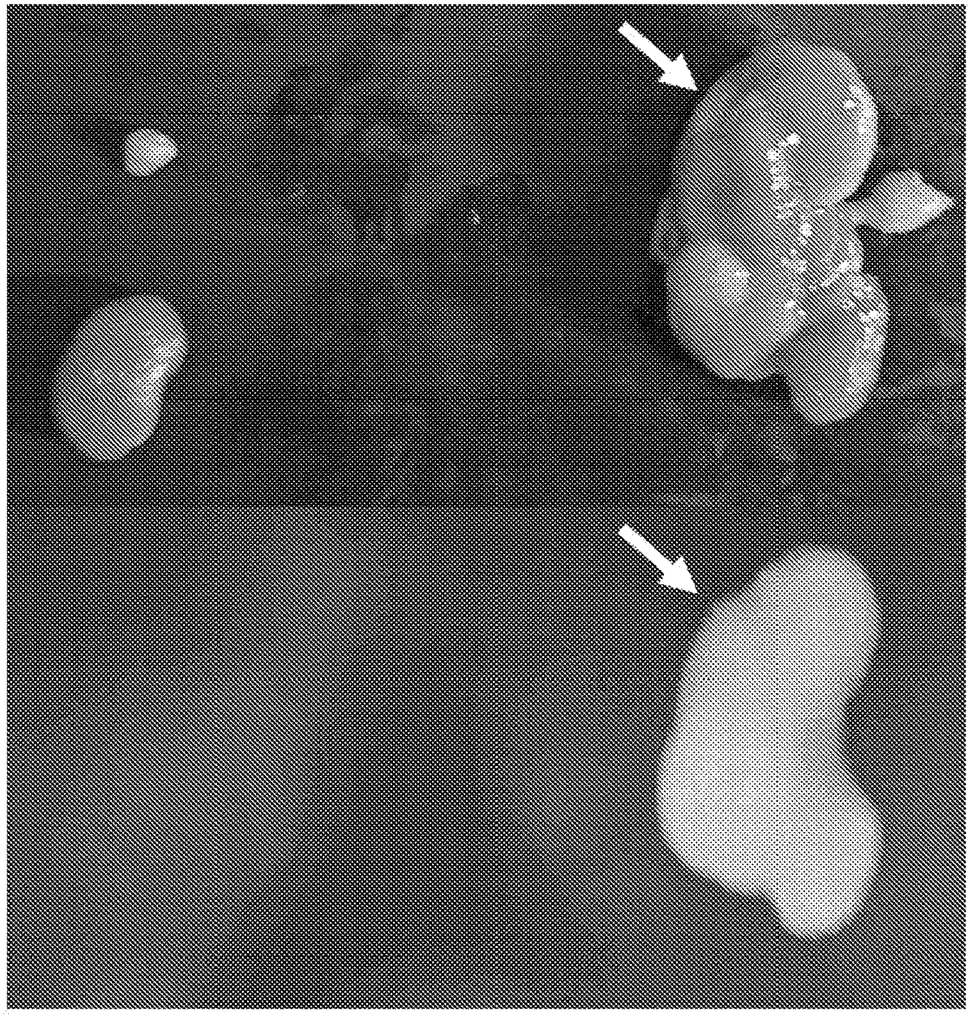

Xenograft Model and Biodistribution Studies. The previously described orthotopic xenograft mouse model and a similar rat model were used to assess handheld gamma detection and biodistribution of $^{111}$In-αGD2-IRDye800CW or $^{111}$In-Dinutuximab-IRDye800CW. Neuroblastoma-bearing mice or rats received tail vein injections of $^{111}$In-αGD2-IRDye800CW or $^{111}$In-Dinutuximab-IRDye800CW. Three and four days later, gamma decay was measured percutaneously with the handheld Neoprobe over various regions of the body, including the left flank (tumor region) (FIG. 6A). At both time points, the gamma decay signal was significantly higher in the left flank than in any of the other body regions. At both timepoints ex vivo, tumor gamma decay signal was significantly higher than the right adrenal or right kidney (FIG. 6B). Specific accumulation of $^{111}$In-αGD2-IRDye800CW or $^{111}$In-Dinutuximab-IRDye800CW in GD2-expressing neuroblastoma tumors was examined by gamma decay count and/or fluorescence intensity 3-6 days after probe injection (FIG. 3B-D, 6C, 7A-B). Tumor uptake was typically significantly higher than most other organs (though sometimes similar to spleen and liver which had non-specific accumulation).

Example 9

Figure 7A:
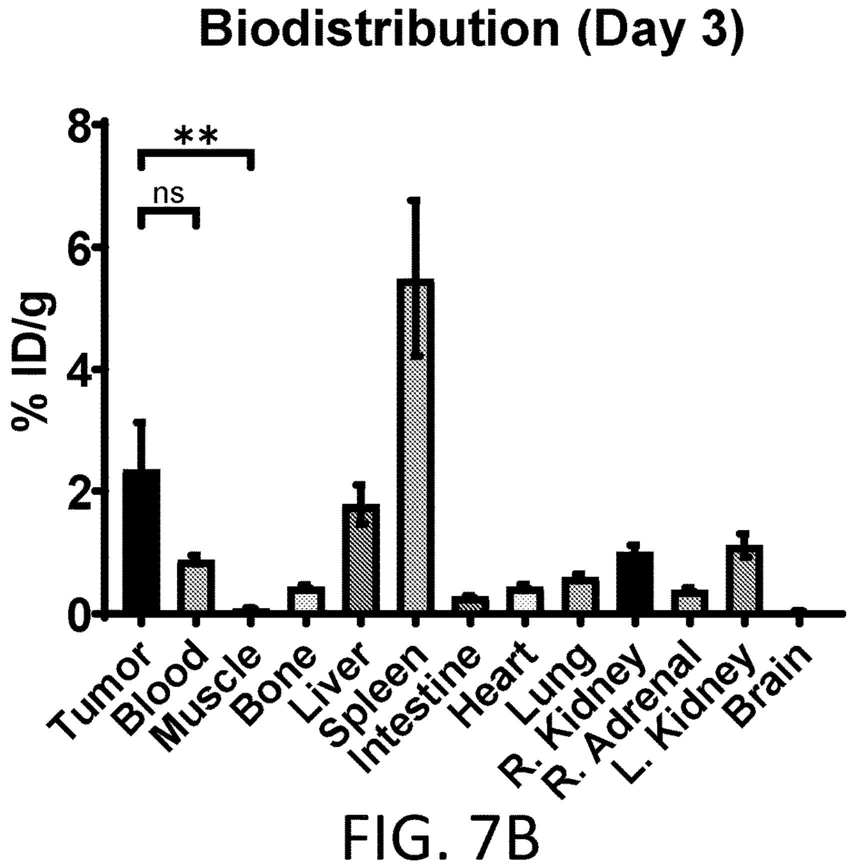
FIGS. 7A-7F. Gamma count biodistribution of $^{111}$In-Dinutuximab-IRDye800CW as percent injected dose per gram of tissue (% ID/g) in rat tumor model 3 days (FIG. 7A) and 5 days (FIG. 7B) after probe injection. White light (left) and fluorescence (right) SPY-PHI images of ex vivo organs 3 days (FIG. 7C) and 5 days (FIG. 7D) after $^{111}$In-Dinutuximab-IRDye800CW injection, tumor and tumor nodules indicated with an arrow. Clockwise from the upper left are right adrenal, tumor, and right kidney.
Figure 7B:
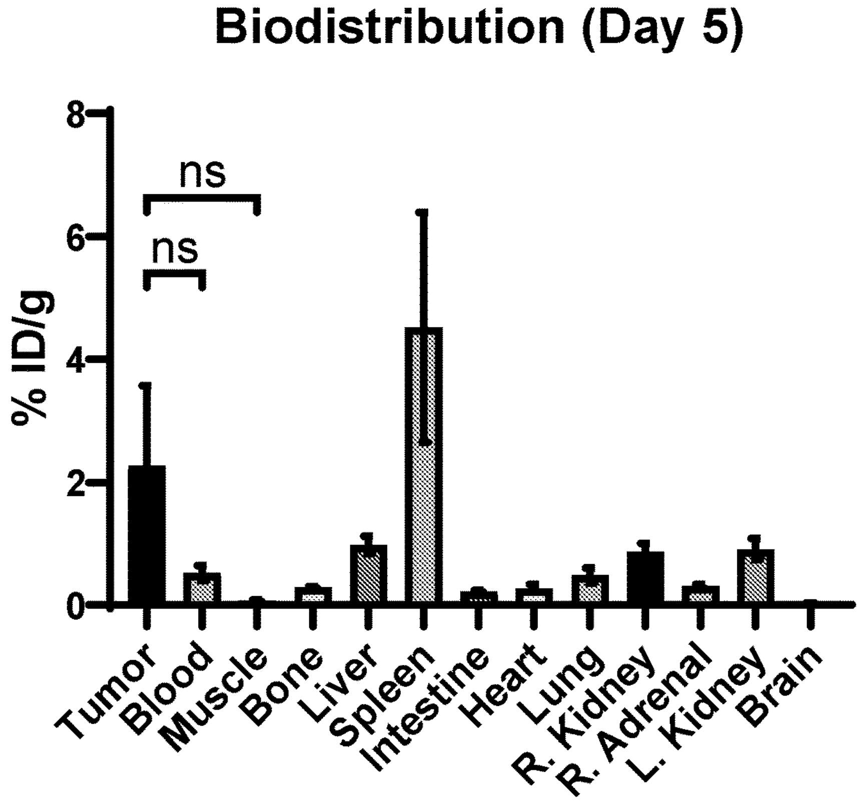
Figure 7C:
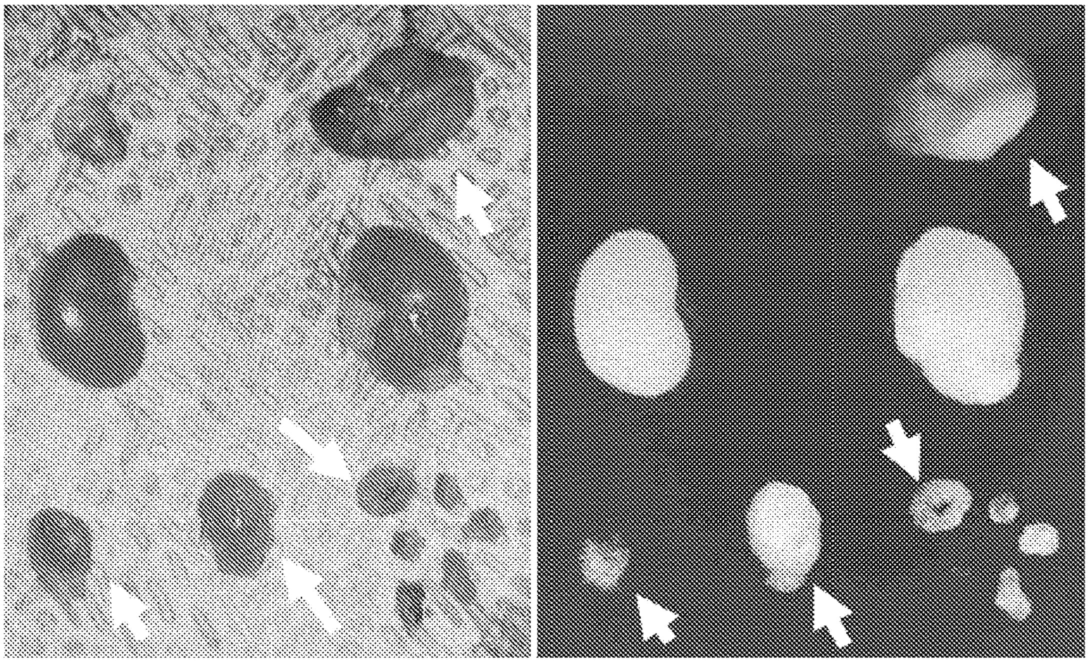
Figure 7D:
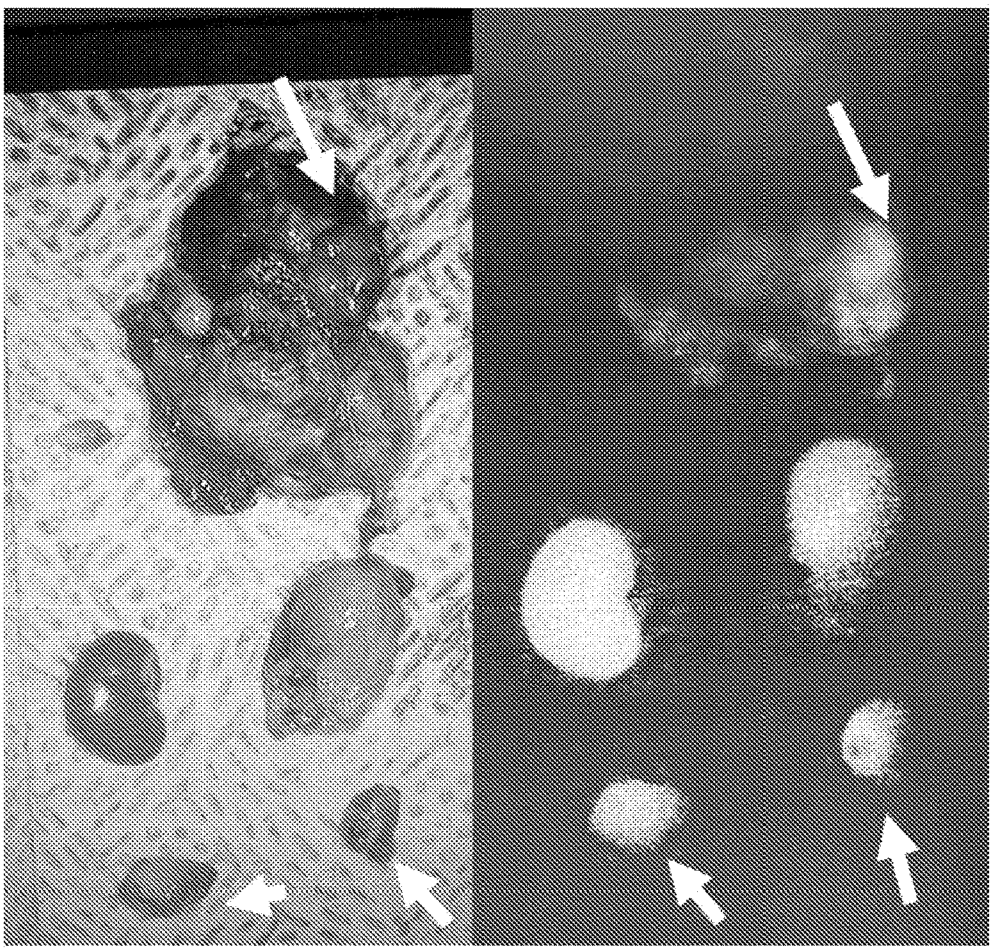

DTPA-Dinutuximab-IRDye800CW Assisted Surgical Resection in Rats $^{111}$In-Dinutuximab-IRDye800CW was synthesized as described above. Tumor bearing rats received tail vein injections of $^{111}$In-Dinutuximab-IRDye800CW. Specific accumulation of $^{111}$In-Dinutuximab-IRDye800CW in GD2-expressing tumors was examined by gamma decay count 3 and 5 days after probe injection (FIGS. 7A and 7B). Tumor uptake of probe was higher than many other organs, though there was non-specific uptake in the spleen and liver, which is common for antibody-based imaging agents.

Figure 7E:
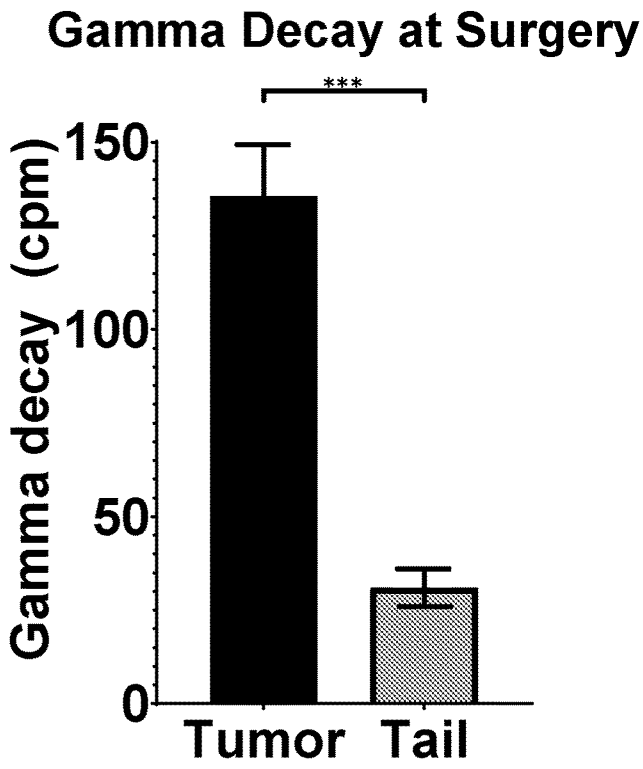
Figure 7F:
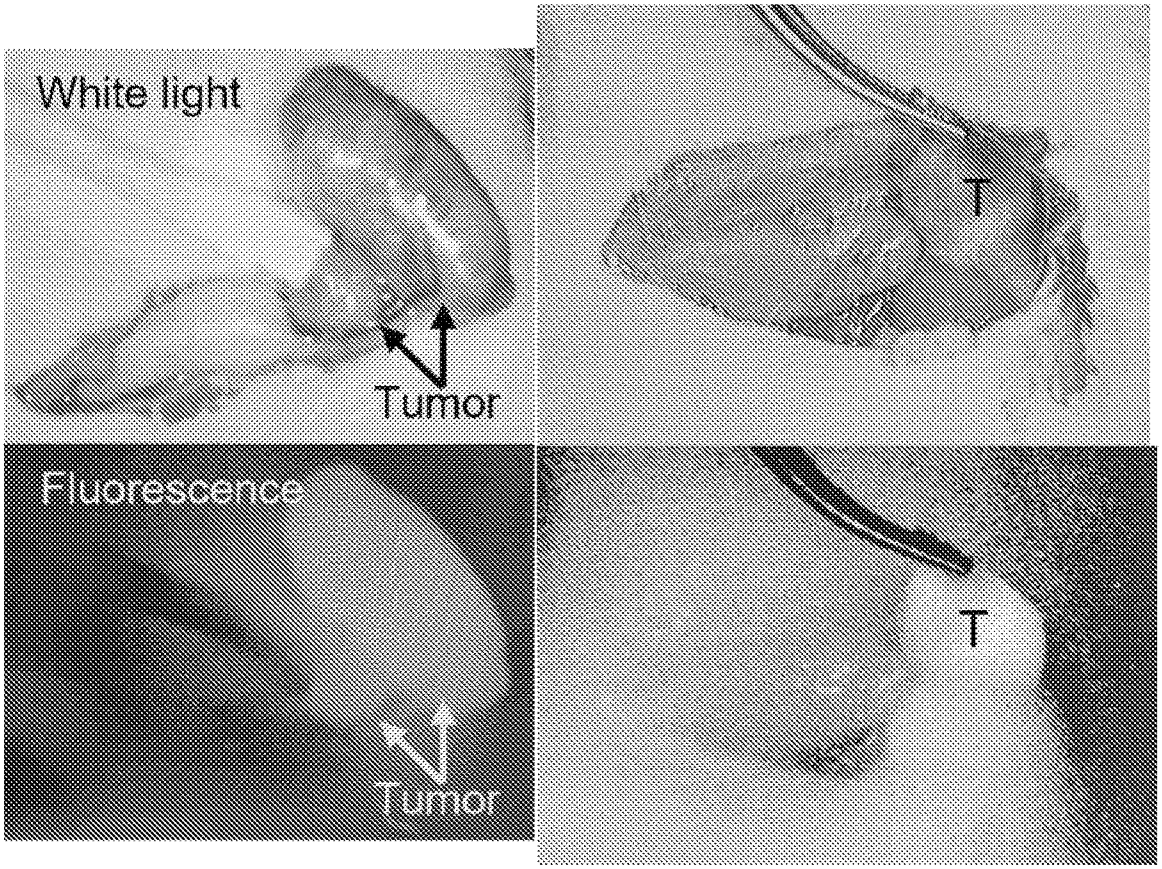

Gamma probe and near-IR camera imaging of the accumulated $^{111}$In-Dinutuximab-IRDye800CW 3 days after injection were used to assist tumor removal in the rat model. Use of the camera also enabled identification of a previously unseen tumor deposit. No tumor deposits were seen with the naked eye that were not also detectable via agent (FIGS. 7E and 7F). Of 9 tumors, 7 were bright and 2 were weakly fluorescent. All tumors had gamma decay higher than background (gamma decay from the tail).

Example 10

Phantom Surgical Resection Model

Figure 8A:
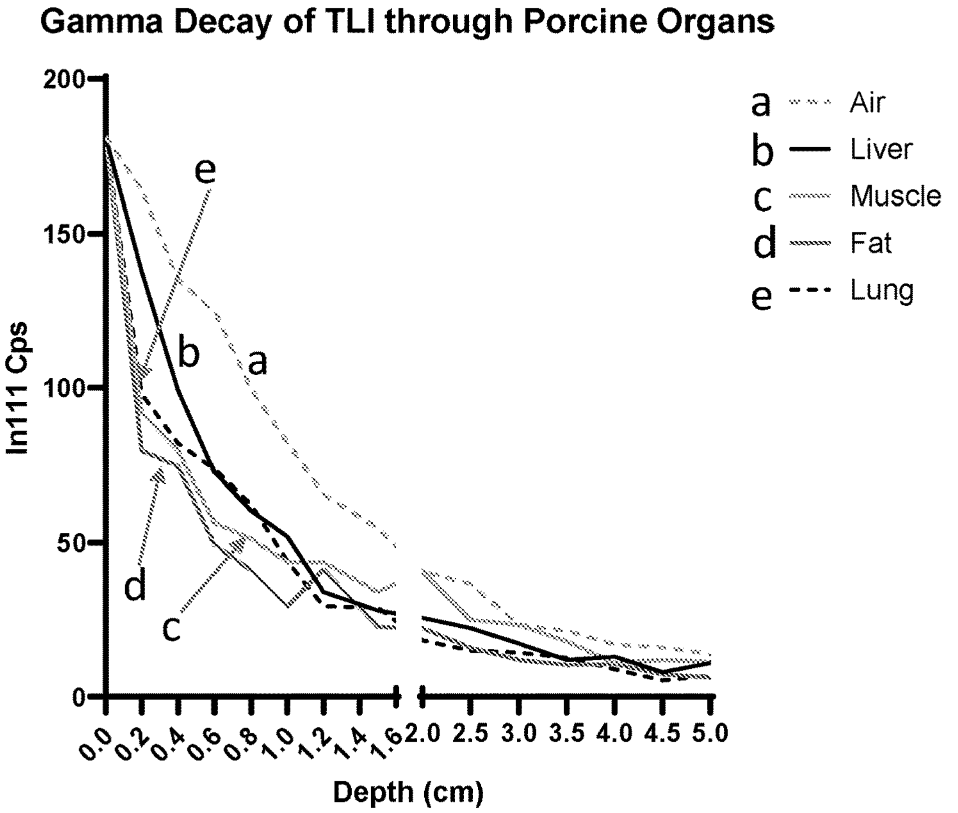
FIGS. 8A-8J.
Figure 8B:
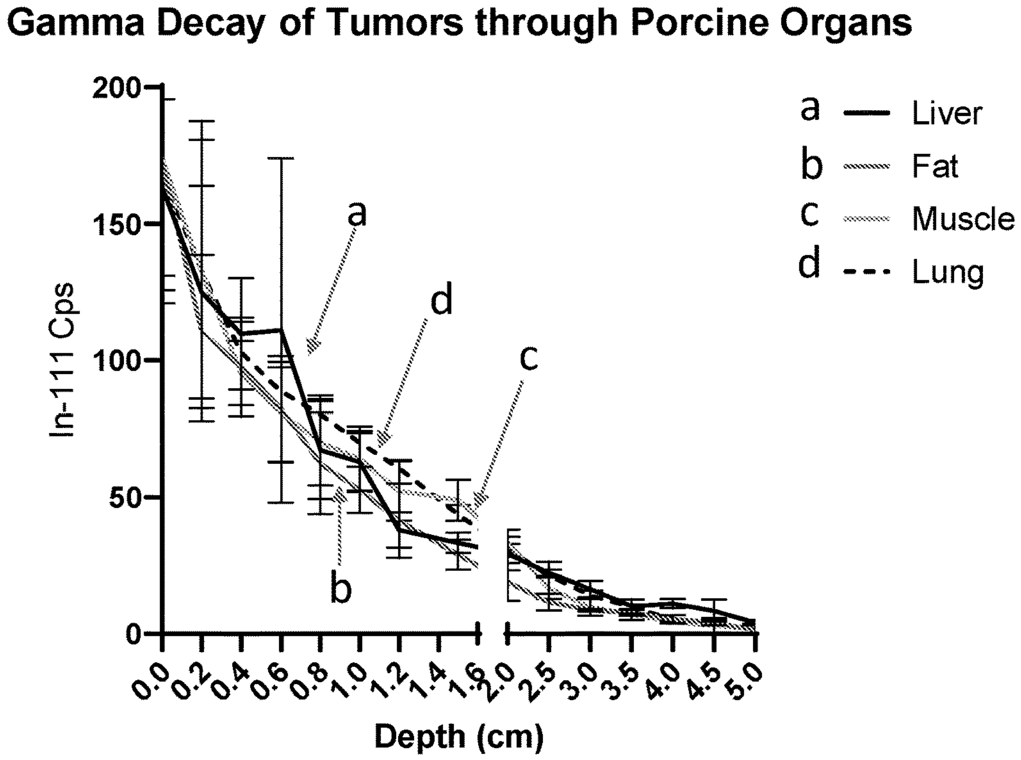

Tumor-like inclusions (TLI) In-111 in gelatin/tris-buffered saline and Polysorbate 20 (TBST)) or ex vivo tumors were plated (n=3), then covered with increasing thicknesses of porcine tissue (liver, muscle, fat, or lung), or no tissue (air). Ex vivo tumors were generated using the previously described orthotopic xenograft mouse model. Animals received tail vein injections of $^{111}$In-αGD2-IRDye800CW 3-6 days prior to tumor isolation. The Neoprobe was used to measure counts per second of indium decay for each TLI/organ at each thickness/tissue (FIGS. 8A and 8B). Gamma decay detection decayed exponentially with increasing intervening space or tissue but remained detectable above background signal through at least 5 cm of tissue.

Figure 8C:
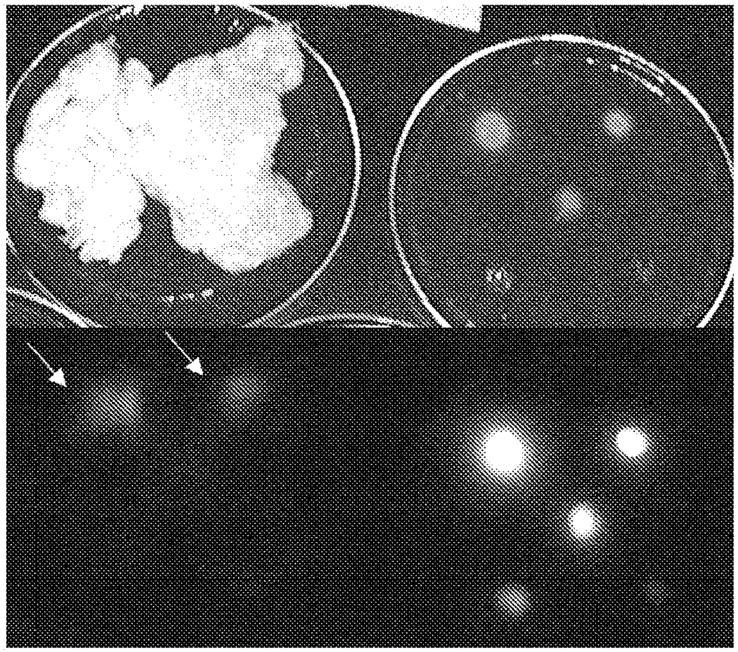
Figure 8D:
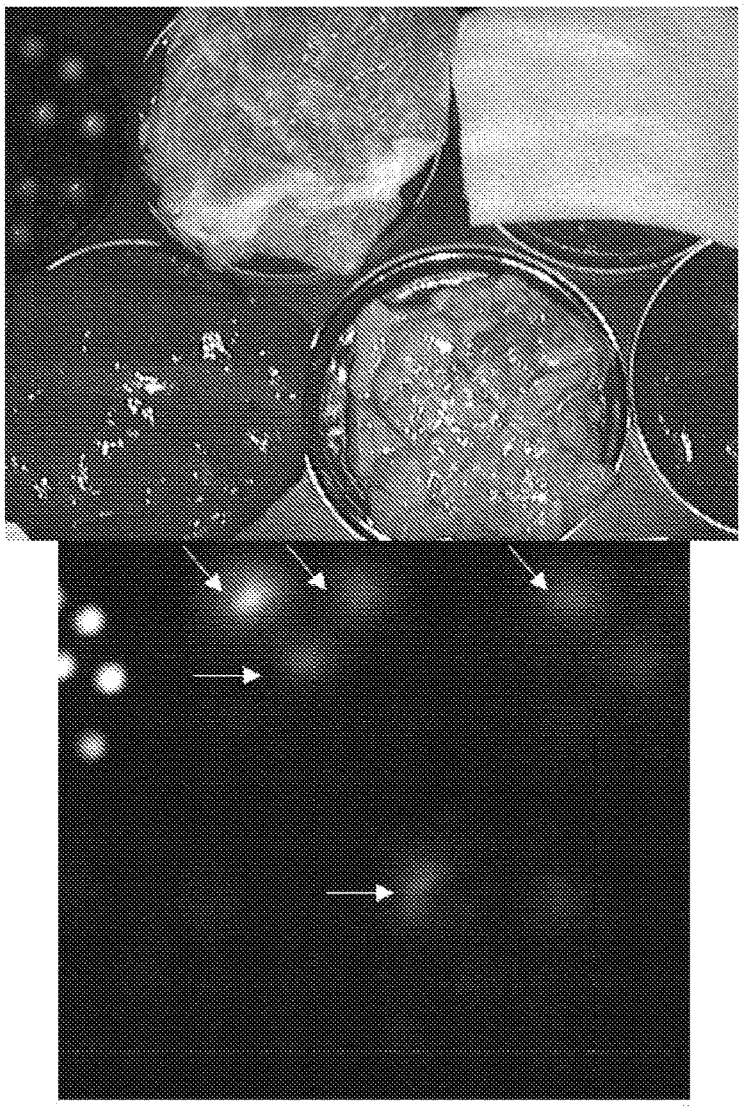
Figure 8E:
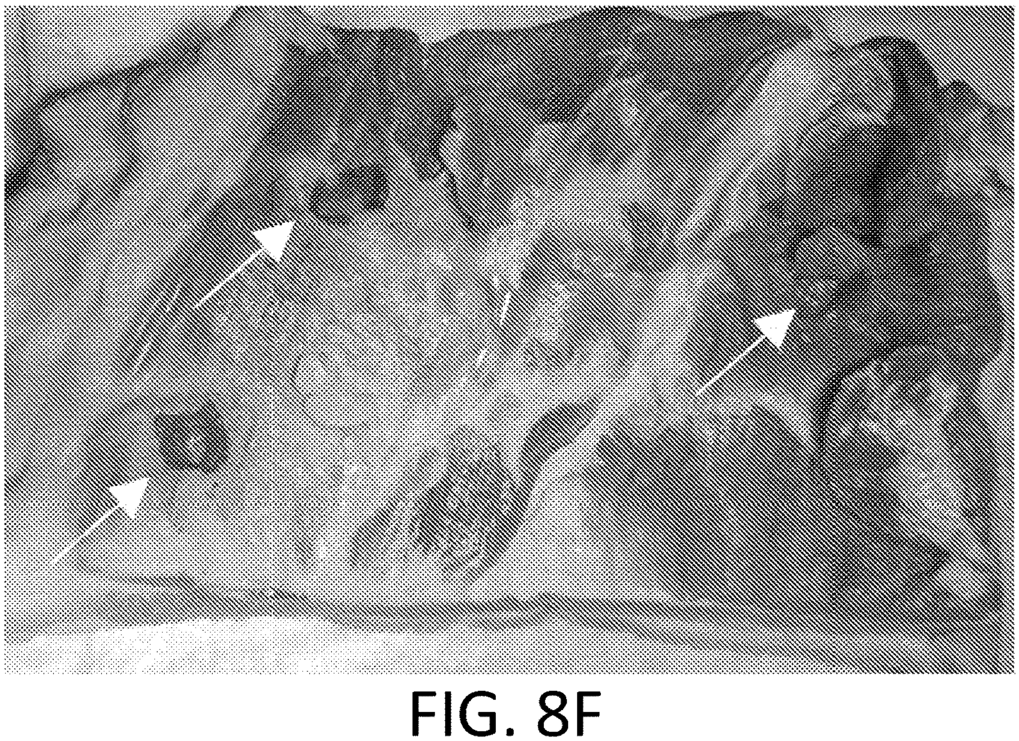
Figure 8F:
Figure 8G:
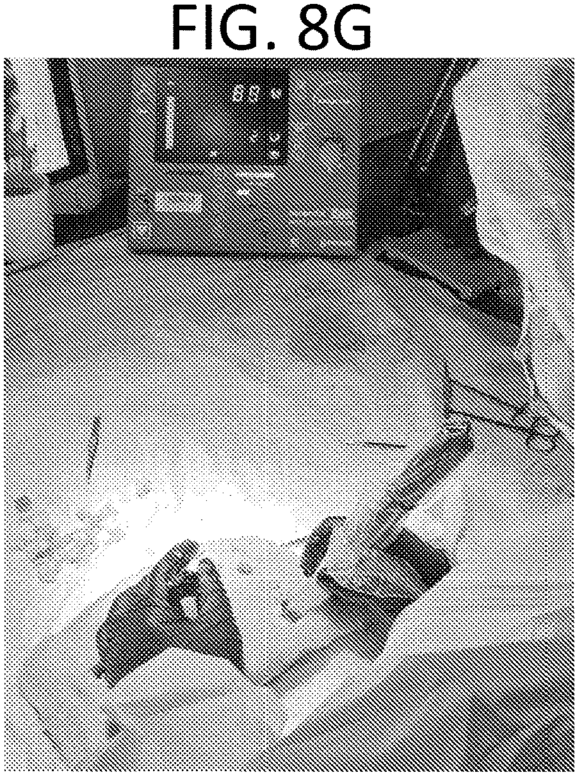
Figure 8H:
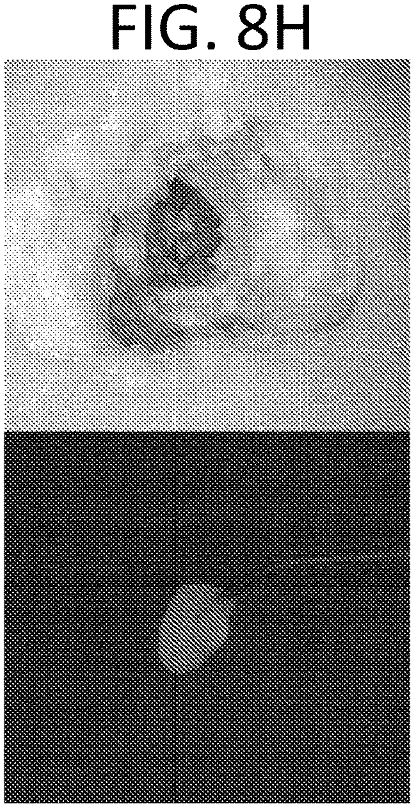

Unconjugated IR-800 was diluted in gelatin/TBST, then plated on hemoglobin-containing gelatin in triplicate. Hemoglobin-containing gelatins or porcine tissues of increasing thicknesses were placed on top and the SPY-PHI was used to identify fluorescence. Brighter dilutions were visible through 4 mm of adipose, muscle, skin (minimally), and lung (minimally) porcine tissue but rarely & minimally through liver (FIGS. 8C and 8D). This indicates accumulated probe will be visible with SPY-PHI through at least up to 4 mm of tissue, with depth dependent on tissue type.

Figure 8I:
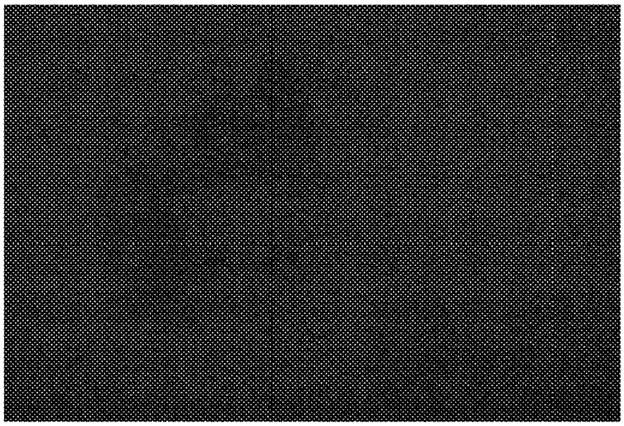
Figure 8J:
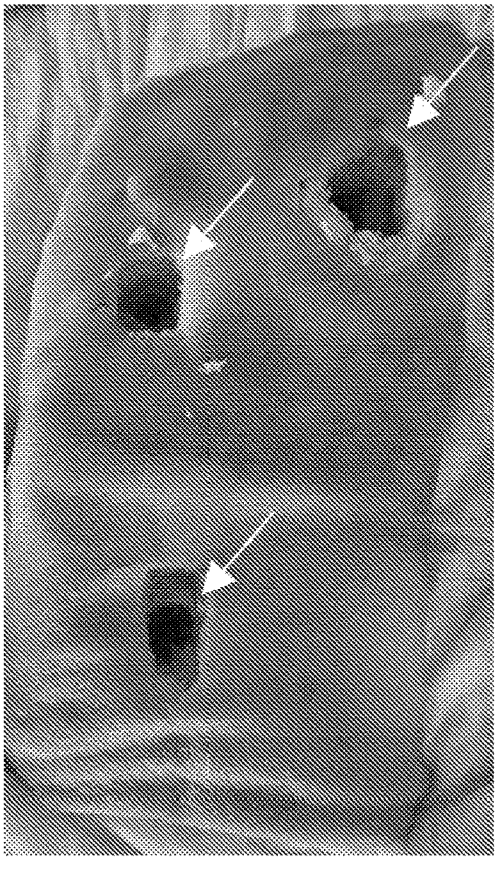

Three ex vivo tumors w/accumulated $^{111}$In-αGD2-IRDye800CW (tail vein injection 4 days prior) were generated using the previously described orthotopic xenograft mouse model. The tumors were buried beneath ~4 cm of porcine body wall (primarily containing skin, muscle, and fascia). The body wall was turned over (now skin side up), and a blinded investigator used the Neoprobe and SPY-PHI camera to dissect through the tissue and find the tumors. The investigator blinded to location of tumors was able to make 3 incisions to find all three buried tumors using the Neoprobe and SPY-PHI camera (FIGS. 8E-8J). No fluorescence is visible after tumor resection (FIG. 8I).

Example 11

References Cited for Examples 1-10

1. Siegel R L, Miller K D, Fuchs H E, Jemal A. Cancer Statistics, 2021. CA Cancer J Clin. 2021; 71(1):7-33. Epub 2021 Jan. 13. doi:10.3322/caac.21654. PubMed PMID: 33433946.
2. Cohn S L, Pearson ADJ, London W B, et al. The International Neuroblastoma Risk Group (INRG) Classification System: An INRG Task Force Report. J Clin Oncol. 2009; 27(2):289-297. doi:10.1200/JCO.2008.16.6785.
3. Gatta G, Botta L, Rossi S, et al. Childhood cancer survival in Europe 1999-2007: results of EUROCARE-5—a population-based study. The Lancet Oncology. 2014; 15(1): 35-47. doi:10.1016/S1470-2045(13)70548-5.
4. Tas M L, Reedijk A M J, Karim-Kos H E, et al. Neuroblastoma between 1990 and 2014 in the Netherlands: Increased incidence and improved survival of high-risk neuroblastoma. European Journal of Cancer. 2020; 124:47-55. doi:10.1016/j.ejca.2019.09.025.
5. Sait S, Modak S. Anti-GD2 immunotherapy for neuroblastoma. Expert Review of Anticancer Therapy. 2017; 17(10):889-904. doi:10.1080/14737140.2017.1364995.
6. Holmes K, Pötschger U, Pearson ADJ, et al. Influence of surgical excision on the survival of patients with stage 4 high-risk neuroblastoma: A report from the HR-NBL1/SIOPEN study. Journal of Clinical Oncology. 2020; 38(25):2902-2915. doi:10.1200/JCO.19.03117.
7. Cañete A, Jovani C, Lopez A, et al. Surgical treatment for neuroblastoma: Complications during 15 years' experience. Journal of Pediatric Surgery. 1998; 33(10):1526-1530. doi:10.1016/S0022-3468(98)90490-0.
8. von Allmen D, Davidoff A M, London W B, et al. Impact of Extent of Resection on Local Control and Survival in Patients From the COG A3973 Study With High-Risk Neuroblastoma. J Clin Oncol. 2017; 35(2):208-216. doi: 10.1200/JCO.2016.67.2642.
9. Wang Z, Wu L C, Chen J Q. Sentinel lymph node biopsy compared with axillary lymph node dissection in early breast cancer: a meta-analysis. Breast Cancer Res Treat. 2011; 129(3):675-689. doi:10.1007/s10549-011-1665-1.
10. Morton D L, Wen D R, Wong J H, et al. Technical Details of Intraoperative Lymphatic Mapping for Early Stage Melanoma. Archives of Surgery. 1992; 127(4):392-399. doi:10.1001/archsurg.1992.01420040034005.
11. Jani A B, Liauw S L, Blend M J. The Role of Indium-111 Radioimmunoscintigraphy in Post-Radical Retropubic Prostatectomy Management of Prostate Cancer Patients. Clin Med Res. 2007; 5(2):123-131. doi:10.3121/cmr.2007.740.
12. Van Oosterom M N, Rietbergen D D D, Welling M M, Van Der Poel H G, Maurer T, Van Leeuwen F W B. Recent advances in nuclear and hybrid detection modalities for image-guided surgery. Expert Review of Medical Devices. 2019; 16(8):711-734. doi:10.1080/17434440.2019.1642104.
13. Commissioner O of the. FDA Approves New Imaging Drug to Help Identify Ovarian Cancer Lesions. FDA. Published Nov. 29, 2021. Accessed Mar. 29, 2023. https://www.fda.gov/news-events/press-announcements/fda-approves-new-imaging-drug-help-identify-ovarian-cancer-lesions
14. Tanyi J L, Randall L M, Chambers S K, et al. A Phase III Study of Pafolacianine Injection (OTL38) for Intraoperative Imaging of Folate Receptor-Positive Ovarian Cancer (Study 006). *J Clin Oncol*. Published online Sep. 7, 2022:JCO.22.00291. doi:10.1200/JCO.22.00291
15. Boogerd L S F, Hoogstins C E S, Schaap D P, et al. Safety and effectiveness of SGM-101, a fluorescent antibody targeting carcinoembryonic antigen, for intraoperative detection of colorectal cancer: a dose-escalation pilot study. The Lancet Gastroenterology & Hepatology. 2018; 3(3):181-191. doi:10.1016/S2468-1253(17)30395-3.
16. Gao R W, Teraphongphom N T, van den Berg N S, et al. Determination of Tumor Margins with Surgical Specimen Mapping Using Near-Infrared Fluorescence. Cancer Research. 2018; 78(17):5144-5154. doi:10.1158/0008-5472.CAN-18-0878.
17. Gangadharan S, Sarkaria I N, Rice D, et al. Multiinstitutional Phase 2 Clinical Trial of Intraoperative Molecular Imaging of Lung Cancer. The Annals of Thoracic Surgery. 2021; 112(4):1150-1159. doi:10.1016/j.athoracsur.2020.09.037.
18. Hekman M C, Rijpkema M, Muselaers C H, et al. Tumor-targeted Dual-modality Imaging to Improve Intraoperative Visualization of Clear Cell Renal Cell Carcinoma: A First in Man Study. *Theranostics*. 2018; 8(8): 2161-2170. doi:10.7150/thno.23335
19. Hekman M C H, Rijpkema M, Bos D L, et al. Detection of Micrometastases Using SPECT/Fluorescence Dual-Modality Imaging in a CEA-Expressing Tumor Model. *J Nucl Med.* 2017; 58(5):706-710. doi:10.2967/jnumed.116.185470
20. Vargas S H, Ghosh S C, Azhdarinia A. New Developments in Dual-Labeled Molecular Imaging Agents. *J Nucl Med.* 2019; 60(4):459-465. doi:10.2967/jnumed.118.213488
21. Straathof K, Flutter B, Wallace R, et al. Antitumor activity without on-target off-tumor toxicity of GD2-chimeric antigen receptor T cells in patients with neuroblastoma. Science Translational Medicine. 2020; 12(571): eabd6169. doi:10.1126/scitranslmed.abd6169.
22. Butch E R, Mead P E, Amador Diaz V, et al. Positron Emission Tomography Detects In Vivo Expression of Disialoganglioside GD2 in Mouse Models of Primary and Metastatic Osteosarcoma. Cancer Research. 2019; 79(12):3112-3124. doi:10.1158/0008-5472.CAN-18-3340.
23. Lammie G, Cheung N, Gerald W, Rosenblum M, Cordoncardo C. GANGLIOSIDE G D (2) EXPRESSION IN THE HUMAN NERVOUS-SYSTEM AND IN NEUROBLASTOMAS—AN IMMUNOHISTOCHEMICAL STUDY. International Journal of Oncology. 1993; 3(5): 909-915. doi:10.3892/ijo.3.5.909.
24. Rinehardt H N, Longo S, Gilbert R, et al. Handheld PET Probe for Pediatric Cancer Surgery. Cancers. 2022; 14(9): 2221. doi:10.3390/cancers14092221.
25. Ovacik M, Lin K. Tutorial on Monoclonal Antibody Pharmacokinetics and Its Considerations in Early Development. Clinical and Translational Science. 2018; 11(6): 540-552. doi:10.1111/cts.12567.
26. Vieira P, Rajewsky K. The bulk of endogenously produced IgG2a is eliminated from the serum of adult C57BL/6 mice with a half-life of 6-8 days. European Journal of Immunology. 1986; 16(7):871-874. doi:10.1002/eji.1830160727.
27. Yu A L, Uttenreuther-Fischer M M, Huang C S, et al. Phase I trial of a human-mouse chimeric anti-disialoganglioside monoclonal antibody ch14.18 in patients with refractory neuroblastoma and osteosarcoma. J Clin Oncol. 1998; 16(6):2169-2180. doi:10.1200/jco.1998.16.6.2169.
28. Croce A C, Bottiroli G. Autofluorescence Spectroscopy and Imaging: A Tool for Biomedical Research and Diagnosis. *Eur J Histochem EJH.* 2014; 58(4):2461. doi:10.4081/ejh.2014.2461
29. Gao R W, Teraphongphom N T, van den Berg N S, et al. Determination of Tumor Margins with Surgical Specimen Mapping Using Near-Infrared Fluorescence. *Cancer Res.* 2018; 78(17):5144-5154. doi:10.1158/0008-5472.CAN-18-0878
30. Nalla A, Buch I, Hesse B. Easy and Efficient 111Indium Labeling of Long-Term Stored DTPA Conjugated Protein. Current Radiopharmaceuticals. 2011; 4(1):1-4.
31. Vavere A L, Butch E R, Dearling J L J, et al. 64Cu-p-NH2-Bn-DOTA-hu14.18K322A, a PET Radiotracer Targeting Neuroblastoma and Melanoma. Journal of Nuclear Medicine. 2012; 53(11):1772-1778. doi:10.2967/jnumed.112.104208.
32. Nguyen F, Guan P, Guerrero D T, et al. Structural Optimization and Enhanced Prodrug-Mediated Delivery Overcomes Camptothecin Resistance in High-Risk Solid Tumors. Cancer Research. 2020; 80(19):4258-4265. doi:10.1158/0008-5472.CAN-20-1344.
33. Nguyen F, Guan P, Guerrero D T, et al. Structural Optimization and Enhanced Prodrug-Mediated Delivery Overcomes Camptothecin Resistance in High-Risk Solid Tumors. *Cancer Res.* 2020; 80(19):4258-4265. doi:10.1158/0008-5472.CAN-20-1344
34. Cheever M A, Allison J P, Ferris A S, et al. The Prioritization of Cancer Antigens: A National Cancer Institute Pilot Project for the Acceleration of Translational Research. Clinical Cancer Research. 2009; 15(17):5323-5337. doi:10.1158/1078-0432.CCR-09-0737.
35. Hernot S, van Manen L, Debie P, Mieog J S D, Vahrmeijer A L. Latest developments in molecular tracers for fluorescence image-guided cancer surgery. The Lancet Oncology. 2019; 20(7):e354-e367. doi:10.1016/S1470-2045(19)30317-1.
36. Vahrmeijer A L, Hutteman M, van der Vorst J R, van de Velde CJH, Frangioni J V. Image-guided cancer surgery using near-infrared fluorescence. Nat Rev Clin Oncol. 2013; 10(9):507-518. doi:10.1038/nrclinonc.2013.123.
37. Rudnick S I, Lou J, Shaller C C, et al. Influence of Affinity and Antigen Internalization on the Uptake and Penetration of Anti-HER2 Antibodies in Solid Tumors. *Cancer Res.* 2011; 71(6):2250-2259. doi:10.1158/0008-5472.CAN-10-2277
38. Houghton J L, Abdel-Atti D, Scholz W W, Lewis J S. Preloading with Unlabeled CA19.9 Targeted Human Monoclonal Antibody Leads to Improved PET Imaging with 89Zr-5B1. *Mol Pharm.* 2017; 14(3):908-915. doi:10.1021/acs.molpharmaceut.6b01130
39. Yu A L, Gilman A L, Ozkaynak M F, et al. Long-Term Follow-up of a Phase III Study of ch14.18 (Dinutuximab)+Cytokine Immunotherapy in Children with High- Risk Neuroblastoma: COG Study ANBL0032. Clinical Cancer Research. 2021; 27(8):2179-2189. doi:10.1158/1078-0432.CCR-20-3909.

40. Wellens L M, Deken M M, Sier C F M, et al. Anti-GD2-IRDye800CW as a targeted probe for fluorescence-guided surgery in neuroblastoma. Sci Rep. 2020; 10(1):17667. doi:10.1038/s41598-020-74464-4.

41. Hernot S, van Manen L, Debie P, Mieog J S D, Vahrmeijer A L. Latest developments in molecular tracers for fluorescence image-guided cancer surgery. *Lancet Oncol.* 2019; 20(7):e354-e367. doi:10.1016/S1470-2045(19)30317-1

42. Vahrmeijer A L, Hutteman M, van der Vorst J R, van de Velde CJH, Frangioni J V. Image-guided cancer surgery using near-infrared fluorescence. *Nat Rev Clin Oncol.* 2013; 10(9):507-518. doi:10.1038/nrclinonc.2013.123

It will be apparent that the precise details of the methods or compositions described may be varied or modified without departing from the spirit of the described aspects of the disclosure. We claim all such modifications and variations that fall within the scope and spirit of the claims below.

The invention claimed is:

1. An antibody-conjugate, comprising:

a monoclonal antibody or antigen binding fragment thereof-conjugated to a near-infrared fluorescent dye and a chelator, wherein:

the monoclonal antibody or antigen binding fragment specifically binds to Ganglioside G2 (GD2) and comprises a heavy chain and a light chain comprising heavy and light chain variable regions set forth as SEQ ID NOs: 3 and 4, respectively; and the antibody-conjugate specifically binds to GD2.

2. The antibody-conjugate of claim 1, comprising the monoclonal antibody.

3. The antibody-conjugate of claim 2, wherein the heavy chain and the light chain comprise SEQ ID NOs: 1 and 2, respectively.

4. The antibody-conjugate of claim 1, comprising the antigen binding fragment.

5. The antibody-conjugate of claim 4, wherein the antigen binding fragment is a Fv, Fab, Fab', $F(ab')_2$, scFV, $scFV_2$, diabody, or minibody fragment.

6. The antibody-conjugate of claim 1, wherein the chelator comprises DTPA, DOTA, NOTA, or DFO, or a polyhistidine-tag.

7. The antibody-conjugate of claim 1, comprising:
about 1-5 fluorescent dye molecules and about 1-3 chelators per monoclonal antibody or antigen binding fragment;
about 1-3 fluorescent dye molecules and about 1-2 chelators per monoclonal antibody or antigen binding fragment; or
about 1.5-3 fluorescent dye molecules and about 0.5-2 chelators per monoclonal antibody or antigen binding fragment.

8. The antibody-conjugate of claim 1, comprising about 2-2.5 fluorescent dye molecules and about 1 to 1.5 chelators per monoclonal antibody or antigen binding fragment.

9. The antibody-conjugate of claim 1, comprising:
a molar ratio of the monoclonal antibody or antigen binding fragment to the DTPA of about 1:1.5 to about 1:2 and a molar ratio of the monoclonal antibody or antigen binding fragment to the fluorescent dye of about 1:1 to about 1:3;
a molar ratio of the monoclonal antibody or antigen binding fragment to the DTPA of about 1:1 to about 1:1.5 and a molar ratio of the monoclonal antibody or antigen binding fragment to the fluorescent dye of about 1:2 to about 1:2.5; or
a molar ratio of the monoclonal antibody or antigen binding fragment to the DTPA of about 1:0.5 to about 1:2 and a molar ratio of the monoclonal antibody or antigen binding fragment to the fluorescent dye of about 1:1.5 to about 1:3.

10. The antibody-conjugate of claim 1, wherein the chelator is DTPA.

11. The antibody-conjugate of claim 1, further comprising a radioisotope chelated by the chelator, wherein the radioisotope comprises Indium-111 ($^{111}$In), Copper-64 ($^{64}$Cu), Zirconium-89 ($^{89}$Zr), or Technetium-99m ($^{99m}$Tc).

12. The antibody conjugate of claim 11, wherein the radioisotope comprises $^{111}$In.

13. The antibody-conjugate of claim 1, wherein the near-infrared fluorescent dye comprises 800CW dye.

14. The antibody-conjugate of claim 1, wherein the monoclonal antibody or antigen binding fragment conjugated to a near-infrared fluorescent dye has chemical structure 1 where R is the monoclonal antibody or antigen binding fragment:

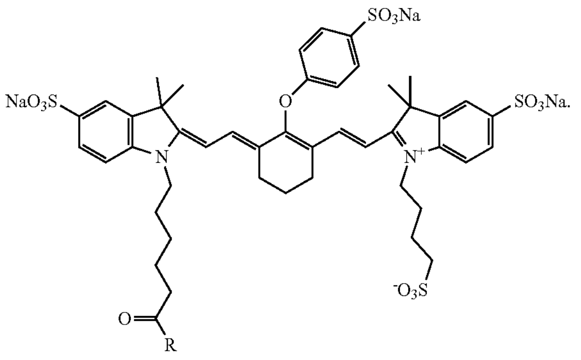

15. The antibody-conjugate of claim 1, wherein the monoclonal antibody or antigen binding fragment is conjugated via covalent bond to the fluorescent dye and the chelator.

16. The antibody-conjugate of claim 1, wherein the monoclonal antibody or antigen binding fragment is conjugated to an additional anti-cancer agent.

17. The antibody-conjugate of claim 16, wherein the additional anti-cancer agent comprises IR700.

18. A method of identifying GD2 positive cancer tissue in a subject, comprising administering to the subject an amount of the antibody-conjugate of claim 1 effective to label the GD2-positive cancer tissue in the subject.

19. A method of treating a GD2 positive cancer tissue in a subject, comprising administering to the subject a therapeutically effective amount of the antibody-conjugate of claim 1.

20. A method of producing the antibody-conjugate of claim 1, comprising:
incubating the monoclonal antibody or antigen binding fragment with a near-infrared fluorescent dye and diethylenetriaminepentaacetic acid (DTPA) under conditions sufficient to conjugate the near-infrared fluorescent dye and the DTPA to the monoclonal antibody or antigen binding fragment, to produce the antibody-conjugate, wherein:
(i) the antibody-conjugate has a molar ratio of monoclonal antibody or antigen binding fragment to DTPA of about 1:1.5 to about 1:2 and the antibody-conjugate has a molar ratio of monoclonal antibody or antigen binding fragment to near-infrared fluorescent dye of about 1:1 to about 1:3;
(ii) the antibody-conjugate has a molar ratio of monoclonal antibody or antigen binding fragment to DTPA of about 1:1 to about 1:1.5 and the antibody-conjugate has a molar ratio of monoclonal antibody or antigen binding fragment to near-infrared fluorescent dye of about 1:2 to about 1:2.5; or
(iii) the antibody-conjugate has a molar ratio of monoclonal antibody or antigen binding fragment to DTPA of about 1:0.5 to about 1:2 and the antibody-conjugate has a molar ratio of monoclonal antibody or antigen binding fragment to near-infrared fluorescent dye of about 1:1.5 to about 1:3.

21. A kit for identifying GD2 positive cancer in a subject, comprising: a container comprising the antibody-conjugate of claim 1 and instructions for using the kit.

22. A method of producing the antibody-conjugate of claim 1, comprising:
(a) incubating the monoclonal antibody or antigen binding fragment with diethylenetriaminepentaacetic acid (DTPA) under conditions sufficient to conjugate the DTPA to the monoclonal antibody or antigen binding fragment, thereby producing a monoclonal antibody or antigen binding fragment conjugated to DTPA;
(b) incubating the monoclonal antibody or antigen binding fragment conjugated to DTPA with an 800CW dye under conditions sufficient to conjugate the 800CW dye to the monoclonal antibody or antigen binding fragment conjugated to DTPA, thereby producing a monoclonal antibody or antigen binding fragment conjugated to DTPA and 800CW dye; and
(c) incubating the monoclonal antibody or antigen binding fragment conjugated to DTPA and the 800CW dye with a radioisotope under conditions sufficient to chelate the radioisotope to the monoclonal antibody or antigen binding fragment conjugated to DTPA and 800CW dye, thereby producing the antibody-conjugate.

* * * * *

```
SEQUENCE LISTING

Sequence total quantity: 4
SEQ ID NO: 1           moltype = AA  length = 443
FEATURE                Location/Qualifiers
source                 1..443
                       mol_type = protein
                       organism = synthetic construct
SEQUENCE: 1
EVQLLQSGPE LEKPGASVMI SCKASGSSFT GYNMNWVRQN IGKSLEWIGA IDPYYGGTSY  60
NQKFKGRATL TVDKSSSTAY MHLKSLTSED SAVYYCVSGM EYWGQGTSVT VSSASTKGPS  120
VFPLAPSSKS TSGGTAALGC LVKDYFPEPV TVSWNSGALT SGVHTFPAVL QSSGLYSLSS  180
VVTVPSSSLG TQTYICNVNH KPSNTKVDKR VEPKSCDKTH TCPPCPAPEL LGGPSVFLFP  240
PKPKDTLMIS RTPEVTCVVV DVSHEDPEVK FNWYVDGVEV HNAKTKPREE QYNSTYRVVS  300
VLTVLHQDWL NGKEYKCKVS NKALPAPIEK TISKAKGQPR EPQVYTLPPS REEMTKNQVS  360
LTCLVKGFYP SDIAVEWESN GQPENNYKTT PPVLDSDGSF FLYSKLTVDK SRWQQGNVFS  420
CSVMHEALHN HYTQKSLSLS PGK                                          443

SEQ ID NO: 2           moltype = AA  length = 220
FEATURE                Location/Qualifiers
source                 1..220
                       mol_type = protein
                       organism = synthetic construct
SEQUENCE: 2
EIVMTQSPAT LSVSPGERAT LSCRSSQSLV HRNGNTYLHW YLQKPGQSPK LLIHKVSNRF  60
SGVPDRFSGS GSGTDFTLKI SRVEAEDLGV YFCSQSTHVP PLTFGAGTKL ELKRTVAAPS  120
VFIFPPSDEQ LKSGTASVVC LLNNFYPREA KVQWKVDNAL QSGNSQESVT EQDSKDSTYS  180
LSSTLTLSKA DYEKHKVYAC EVTHQGLSSP VTKSFNRGEC                        220

SEQ ID NO: 3           moltype = AA  length = 113
FEATURE                Location/Qualifiers
source                 1..113
                       mol_type = protein
                       organism = synthetic construct
SEQUENCE: 3
EVQLLQSGPE LEKPGASVMI SCKASGSSFT GYNMNWVRQN IGKSLEWIGA IDPYYGGTSY  60
NQKFKGRATL TVDKSSSTAY MHLKSLTSED SAVYYCVSGM EYWGQGTSVT VSS         113

SEQ ID NO: 4           moltype = AA  length = 115
FEATURE                Location/Qualifiers
source                 1..115
                       mol_type = protein
                       organism = synthetic construct
SEQUENCE: 4
EIVMTQSPAT LSVSPGERAT LSCRSSQSLV HRNGNTYLHW YLQKPGQSPK LLIHKVSNRF  60
SGVPDRFSGS GSGTDFTLKI SRVEAEDLGV YFCSQSTHVP PLTFGAGTKL ELKRT       115
```